(12) United States Patent
Fuji et al.

(10) Patent No.: US 10,219,791 B2
(45) Date of Patent: *Mar. 5, 2019

(54) MEDICAL DEVICE AND METHOD

(71) Applicant: TERUMO KABUSHIKI KAISHA, Shibuya-ku, Tokyo (JP)

(72) Inventors: Tatsunori Fuji, Ebina (JP); Makoto Jinno, Tokyo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 238 days.

This patent is subject to a terminal disclaimer.

(21) Appl. No.: 14/986,040

(22) Filed: Dec. 31, 2015

(65) Prior Publication Data

US 2017/0189052 A1   Jul. 6, 2017

(51) Int. Cl.
| | |
|---|---|
| *A61B 17/3205* | (2006.01) |
| *A61B 17/00* | (2006.01) |
| *A61B 17/02* | (2006.01) |
| *A61B 17/32* | (2006.01) |
| *A61B 90/00* | (2016.01) |

(52) U.S. Cl.
CPC .... *A61B 17/00008* (2013.01); *A61B 17/0218* (2013.01); *A61B 17/320016* (2013.01); *A61B 17/32056* (2013.01); *A61B 90/361* (2016.02); *A61B 2017/00778* (2013.01); *A61B 2017/00907* (2013.01); *A61B 2017/00969* (2013.01); *A61B 2017/32006* (2013.01)

(58) Field of Classification Search
CPC ........ A61B 17/32053; A61B 17/00008; A61B 2017/00778; A61B 2017/00969; A61B 90/361; A61B 2017/32006; A61B 2017/00907; A61B 17/32056; A61B 17/0128; A61B 17/320016
See application file for complete search history.

(56) References Cited

U.S. PATENT DOCUMENTS

| | | | | |
|---|---|---|---|---|
| 5,667,480 A | * | 9/1997 | Knight | A61B 1/018 128/898 |
| 5,814,059 A | * | 9/1998 | Hart | A61B 17/00008 606/142 |
| 5,836,945 A | * | 11/1998 | Perkins | A61B 17/00008 606/41 |
| 5,938,680 A | * | 8/1999 | Ginn | A61B 17/320016 600/210 |
| 6,740,102 B2 | * | 5/2004 | Hess | A61B 17/00008 600/114 |
| 6,770,071 B2 | * | 8/2004 | Woloszko | A61B 18/1402 606/41 |
| 7,645,289 B2 | * | 1/2010 | Bayer | A61B 17/00008 606/159 |
| 7,981,127 B2 | | 7/2011 | Kasahara et al. | |

(Continued)

OTHER PUBLICATIONS

Souza, D. et al, "The No-Touch Technique of Harvesting the Saphenous Vein for Coronary Artery Bypass Grafting Surgery", Multimedia Manual of Cardiothoracic Surgery, pp. 1-6 (2009).

*Primary Examiner* — Julian W Woo
(74) *Attorney, Agent, or Firm* — Buchanan Ingersoll & Rooney PC

(57) ABSTRACT

A blood vessel dissecting device method involves inserting a dissecting device into a living body, advancing the dissecting device along a vein, and dissecting the vein and tissue bound to the vein from other surrounding tissue.

21 Claims, 53 Drawing Sheets

(56) References Cited

U.S. PATENT DOCUMENTS

| | | | | |
|---|---|---|---|---|
| 10,058,345 | B2* | 8/2018 | Langford | A61B 17/320016 |
| 10,076,351 | B2* | 9/2018 | Fujii | A61B 17/32053 |
| 2007/0276418 | A1* | 11/2007 | Kadykowski | A61B 17/00008 |
| | | | | 606/159 |

* cited by examiner

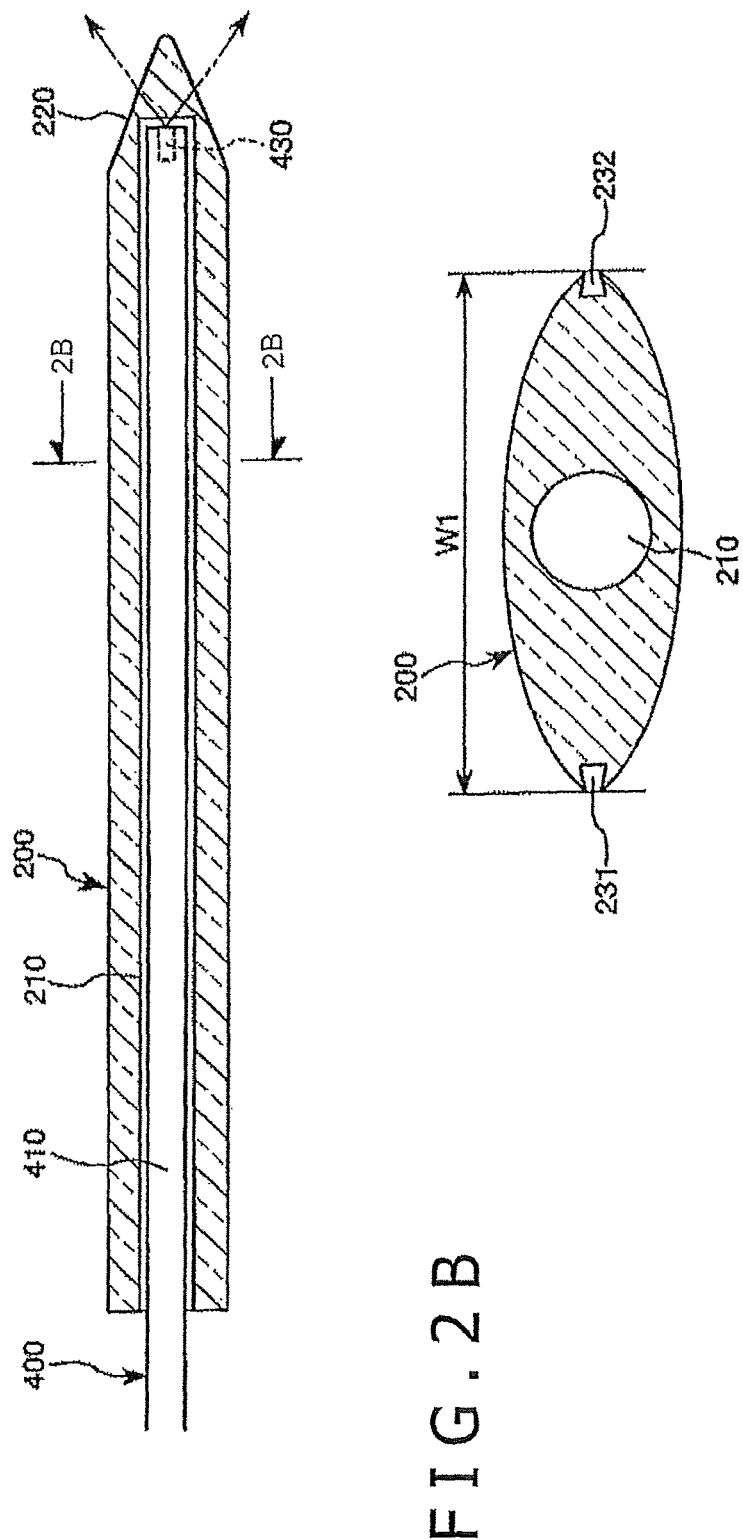

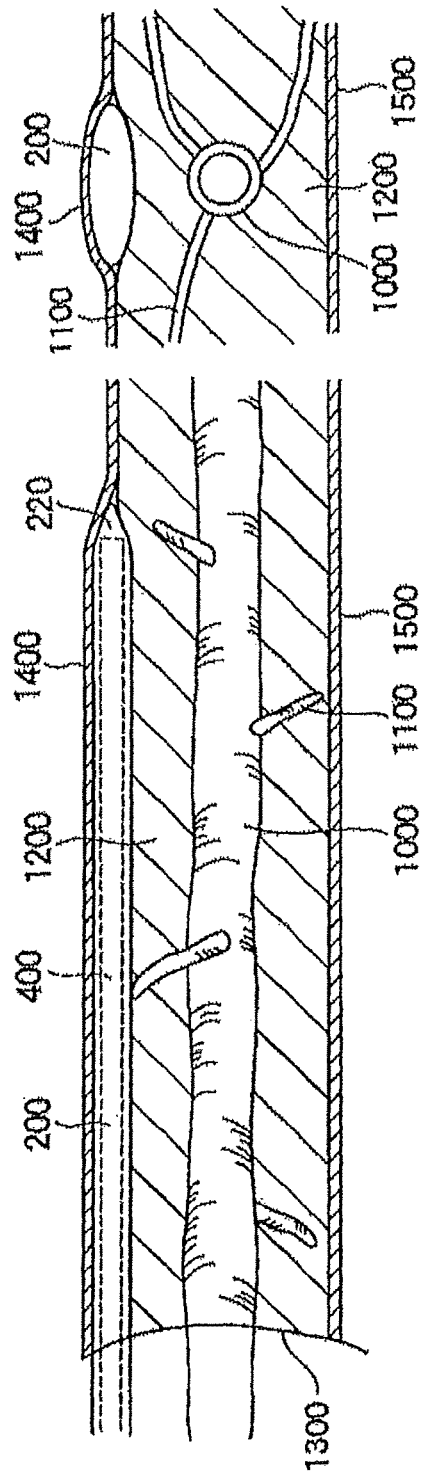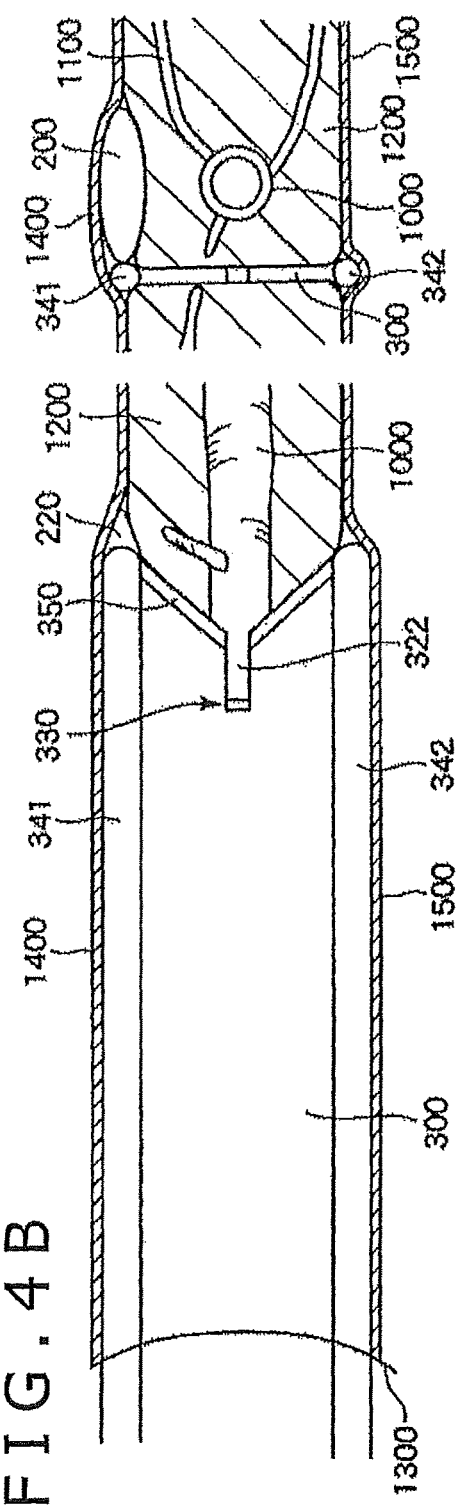

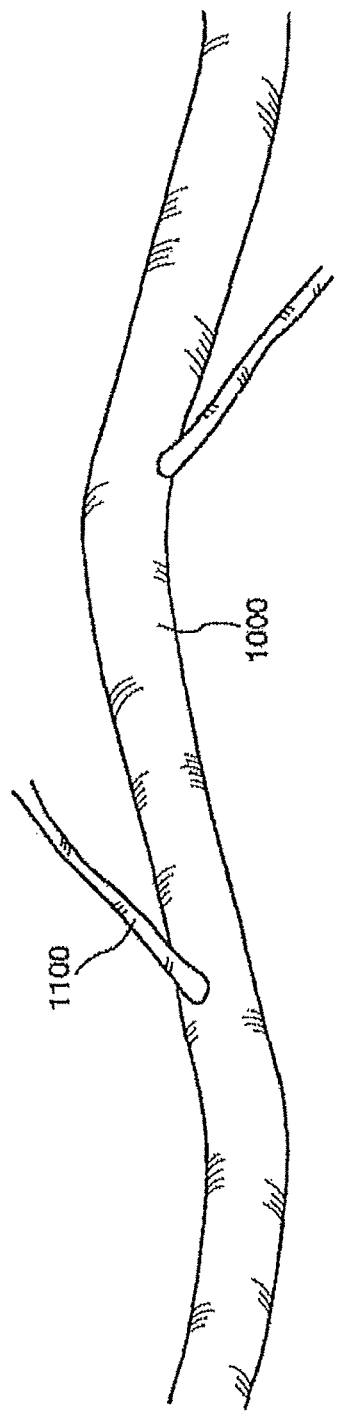
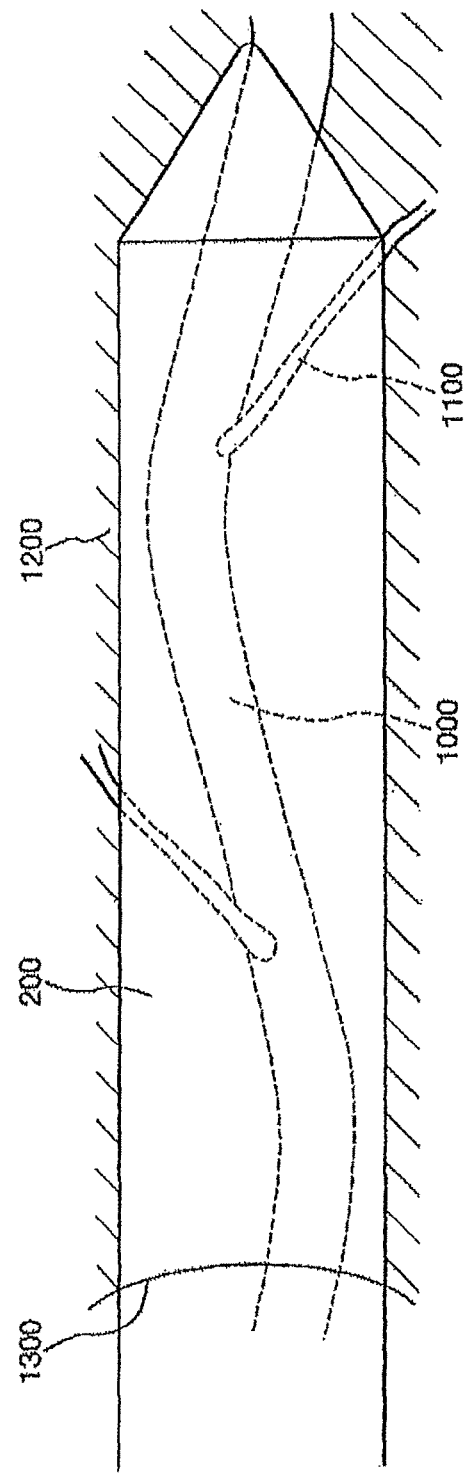
FIG. 15A
FIG. 15B

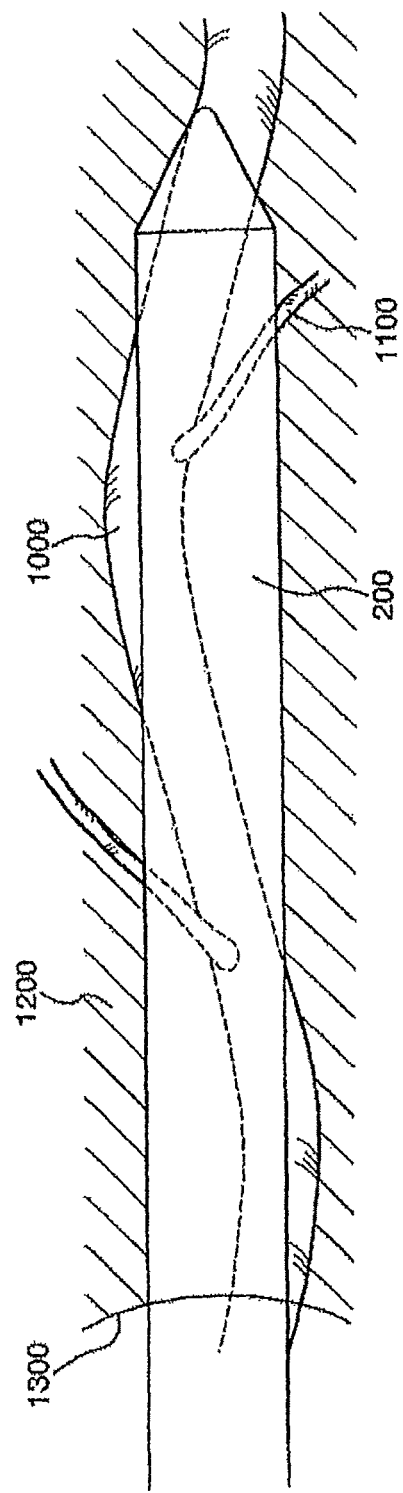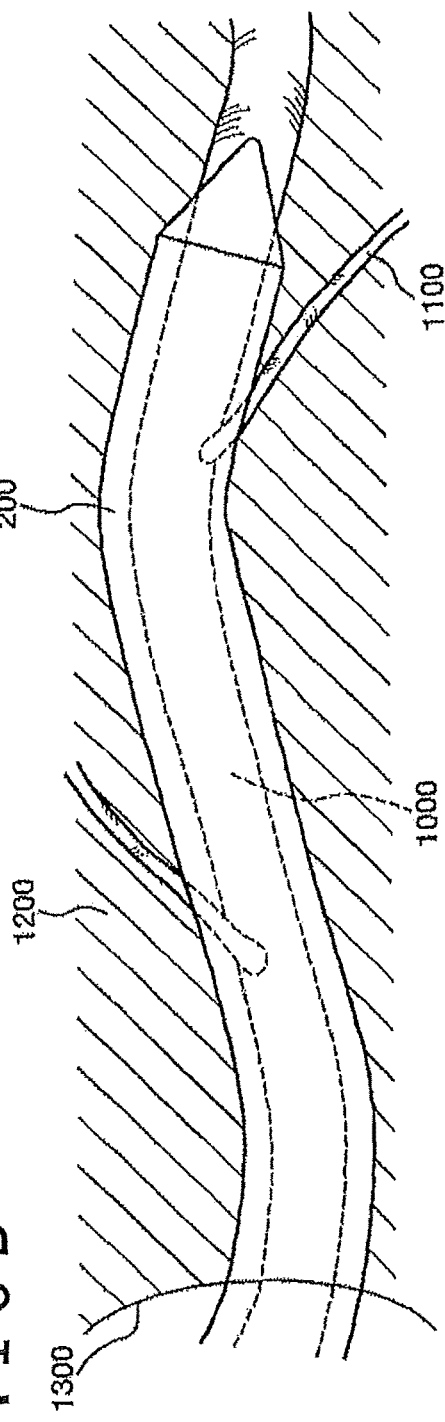
FIG. 16A
FIG. 16B

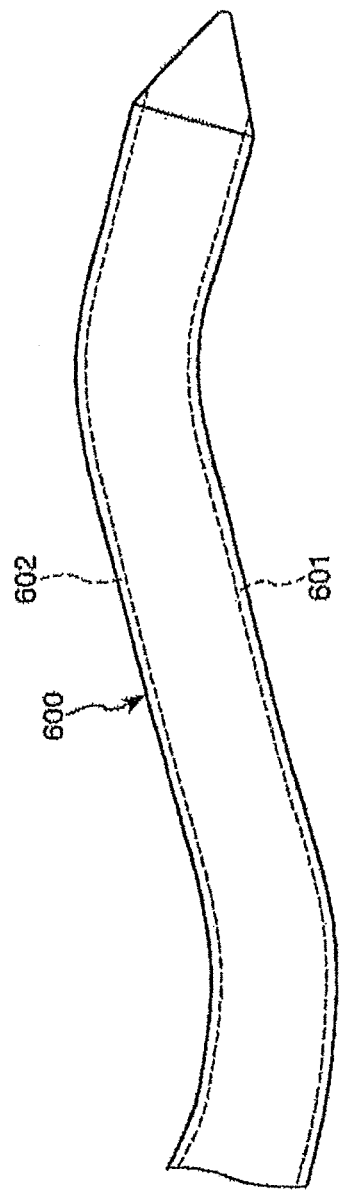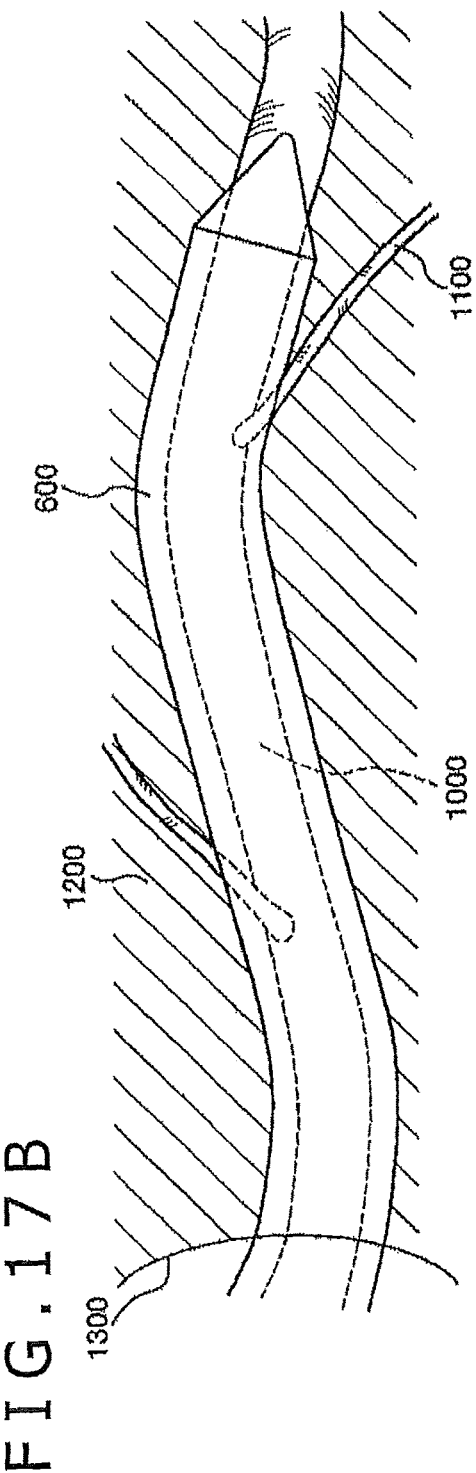
FIG. 17A
FIG. 17B

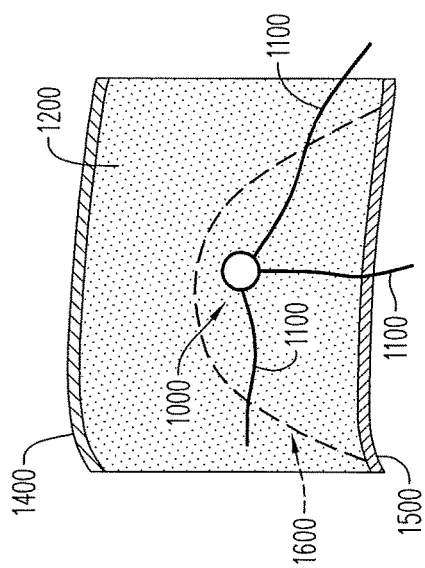
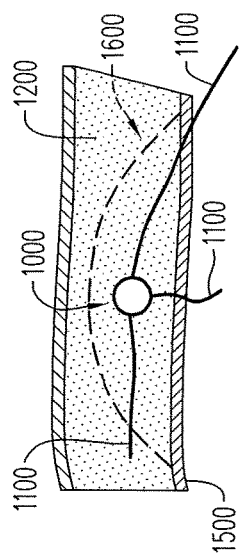
FIG. 21A
FIG. 21B
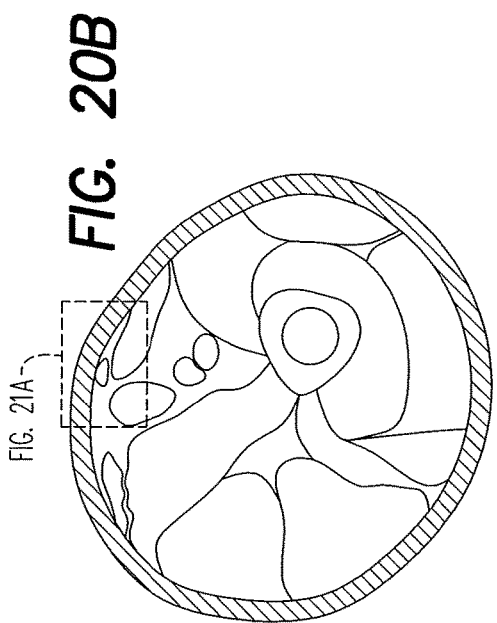
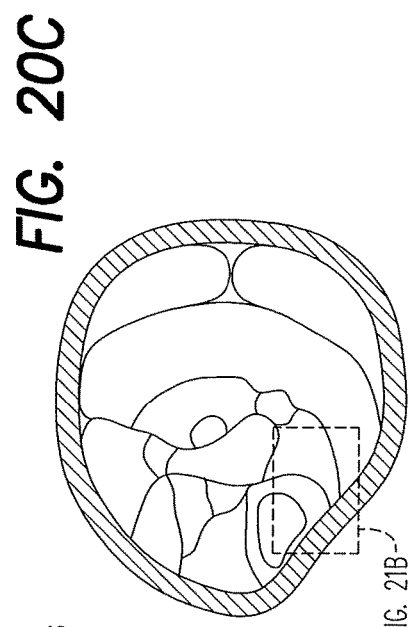
FIG. 20B
FIG. 20C
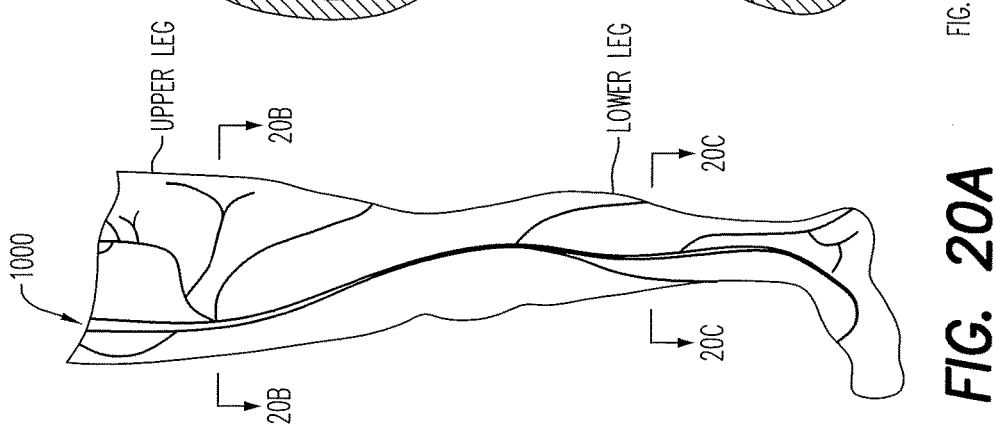
FIG. 20A

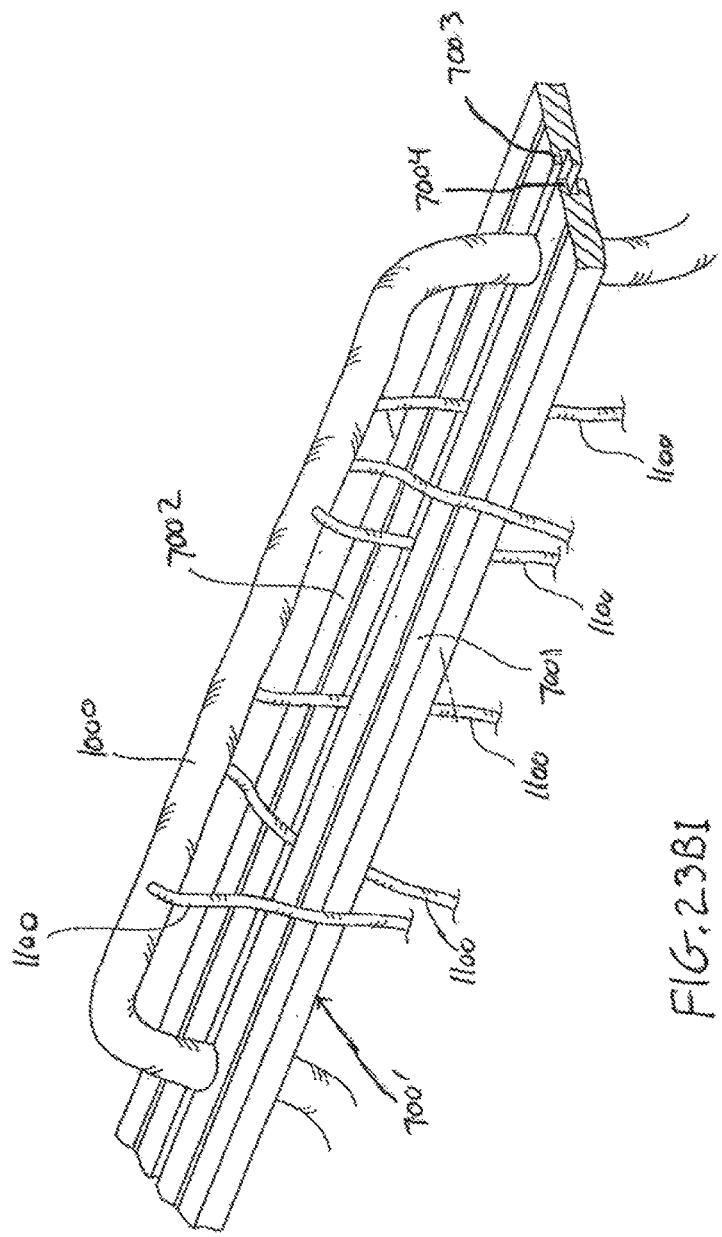

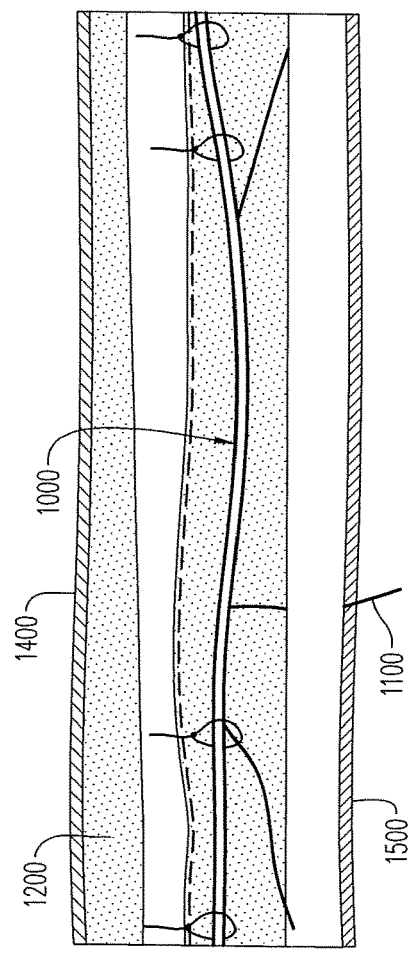
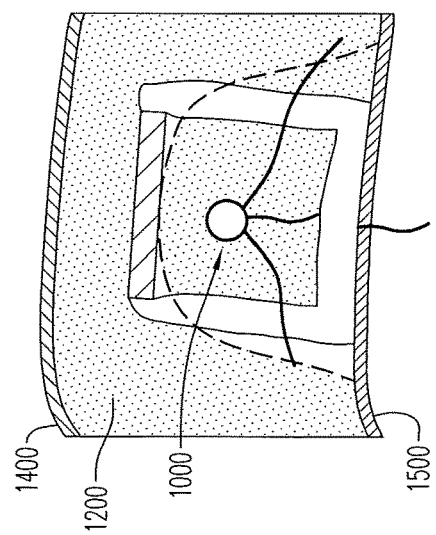
FIG. 24B
FIG. 24A

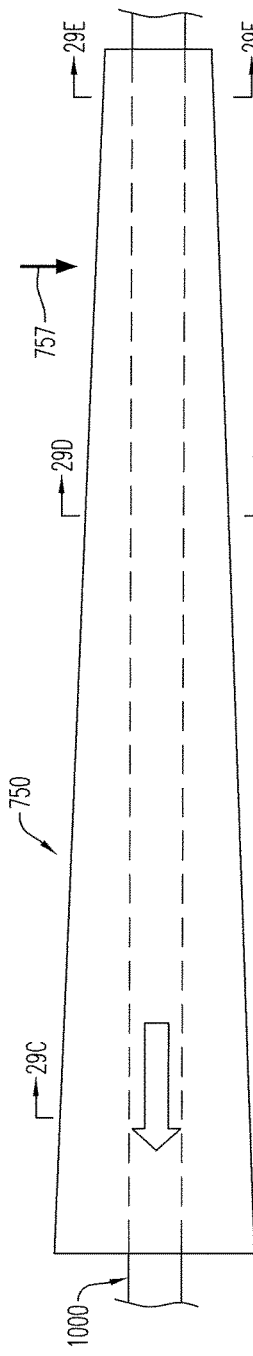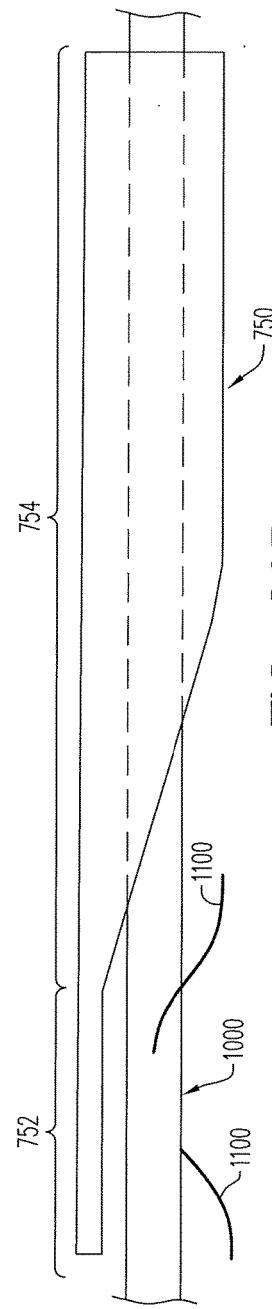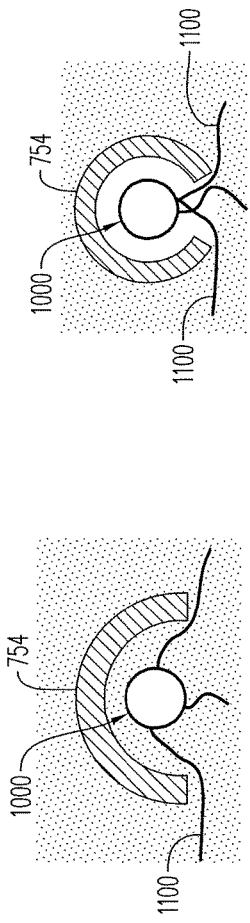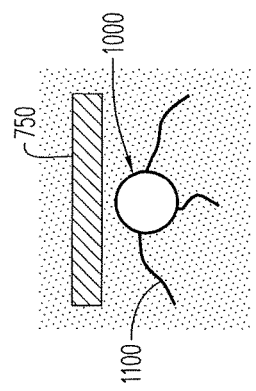

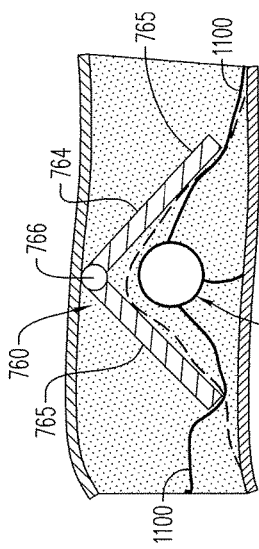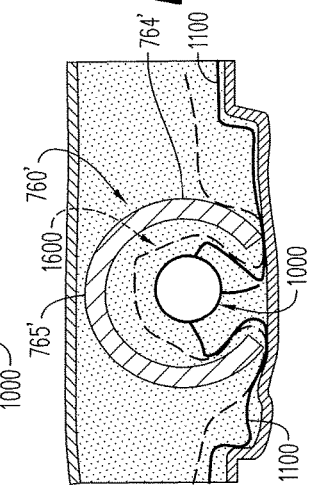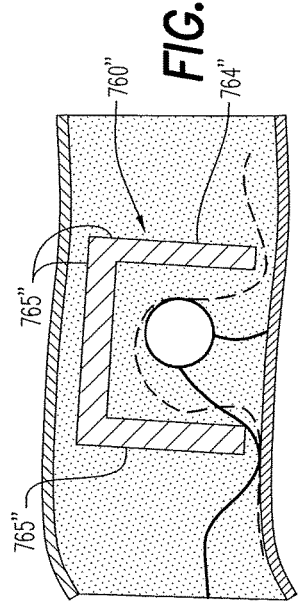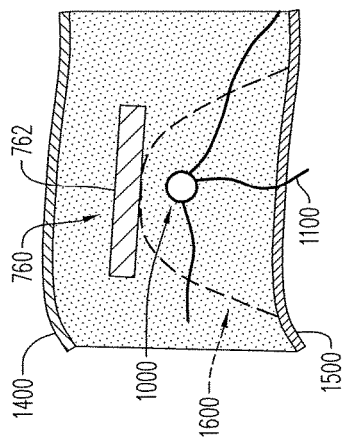

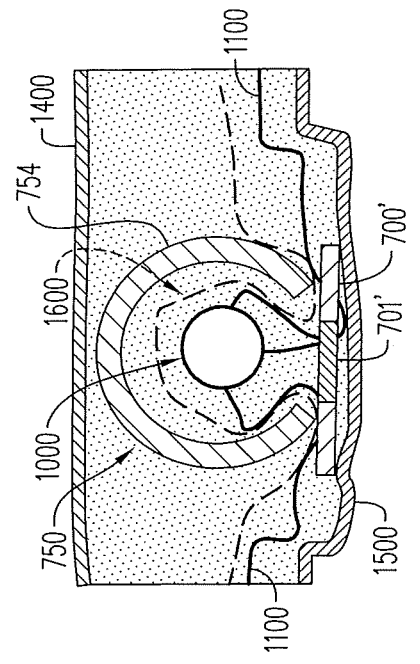
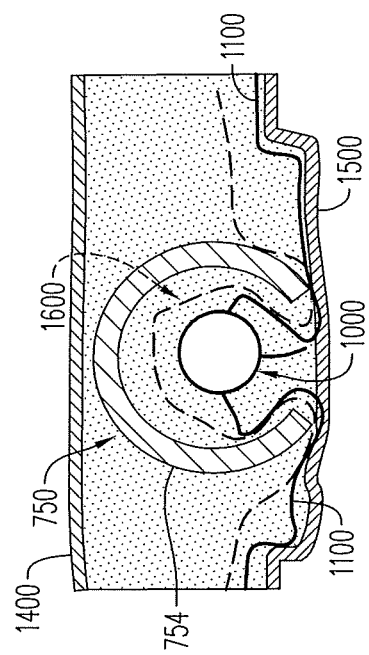

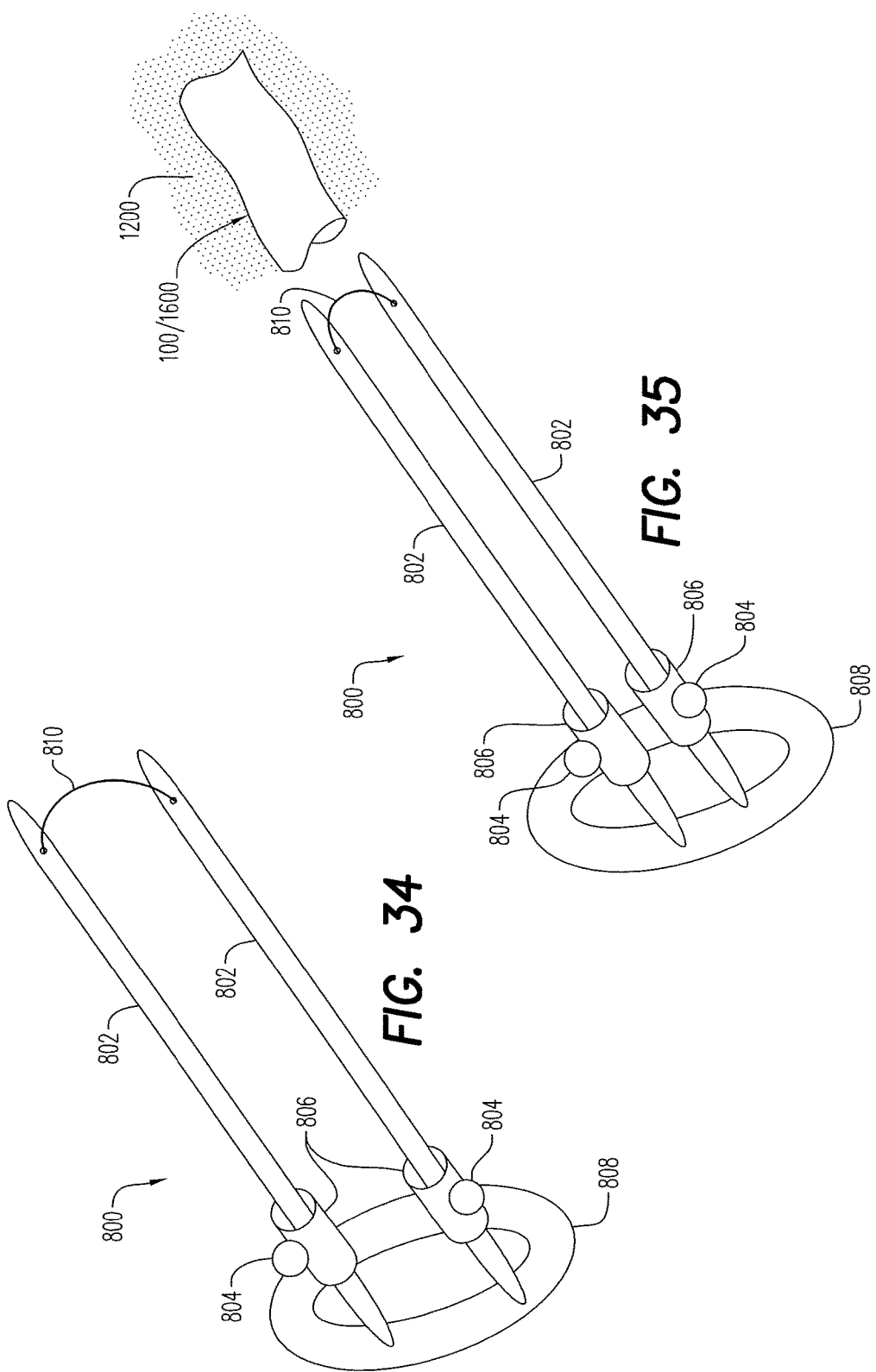

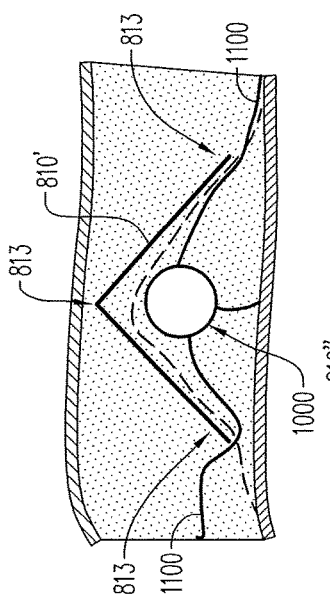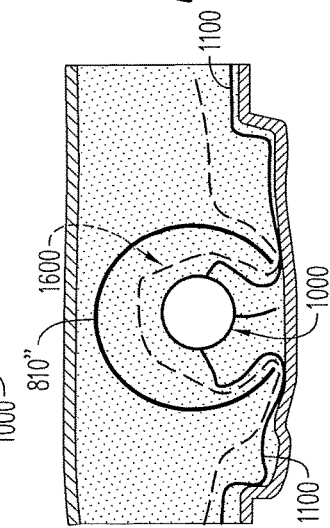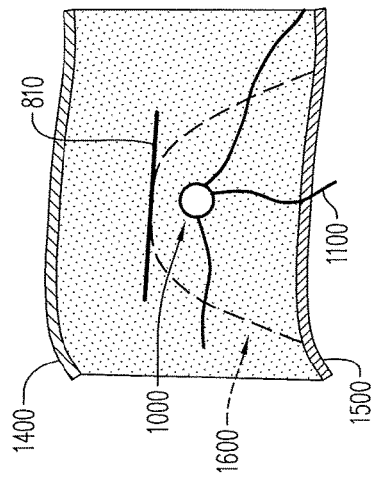

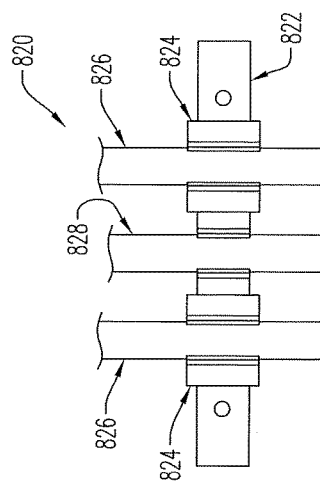
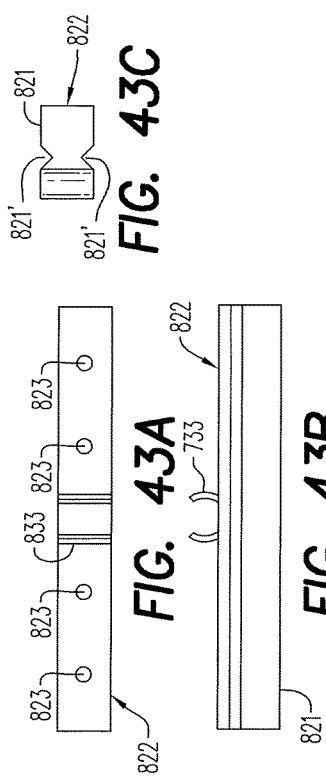
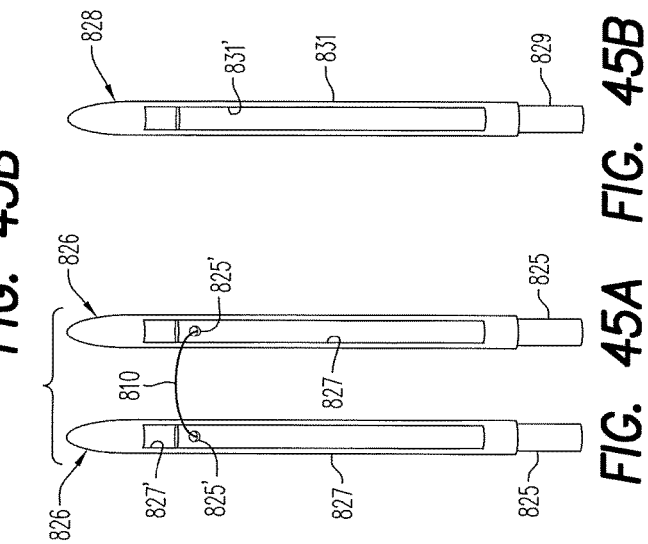

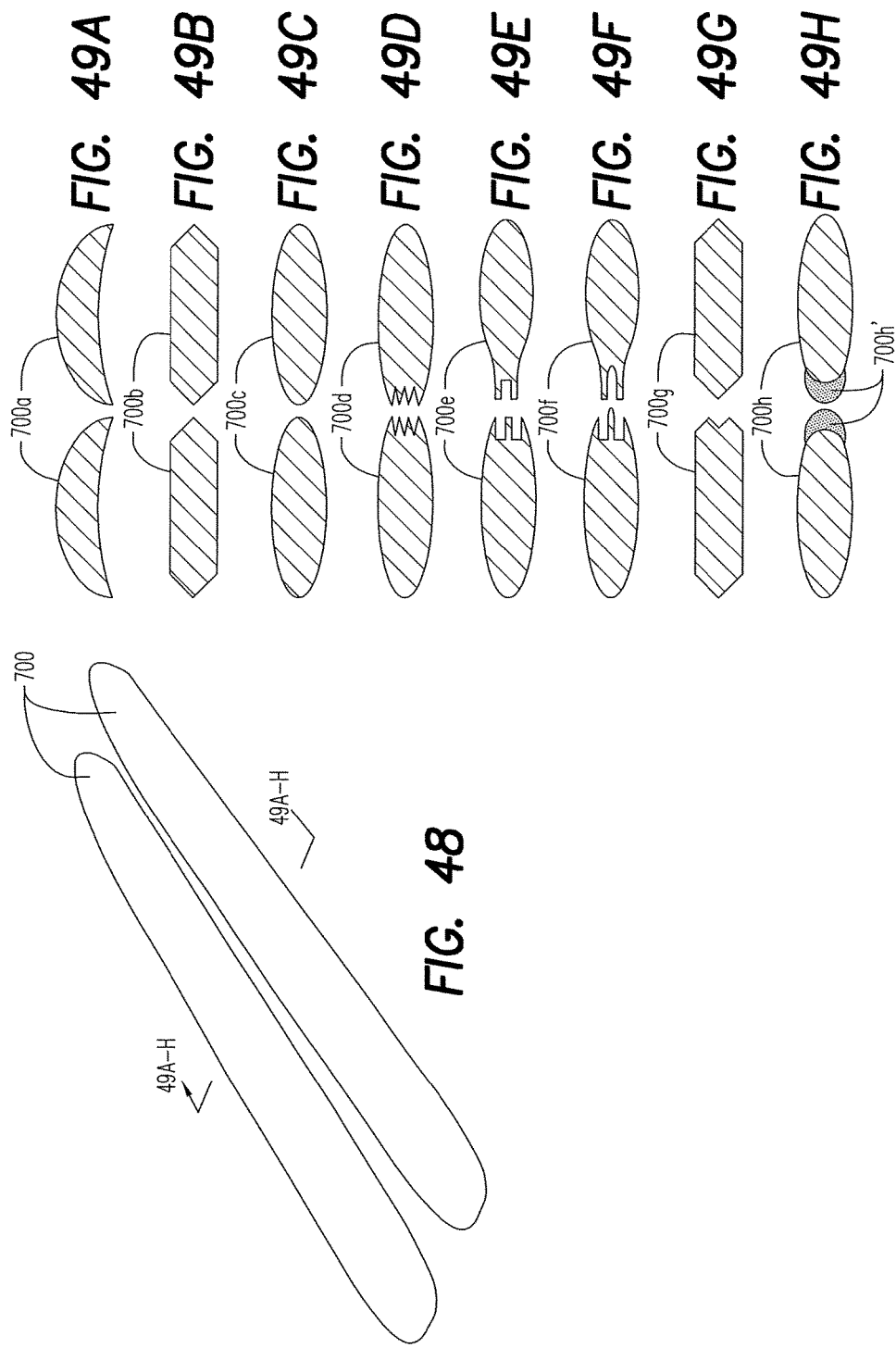

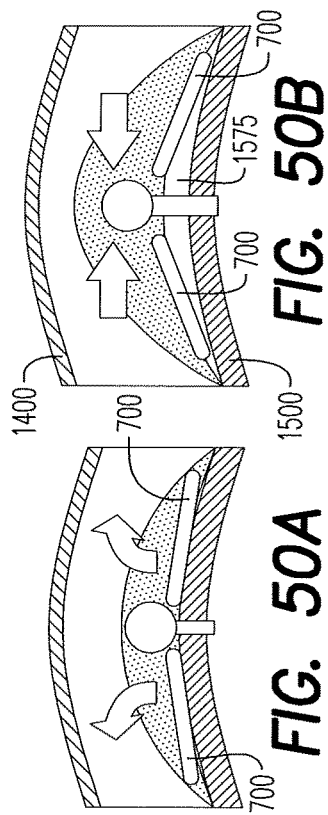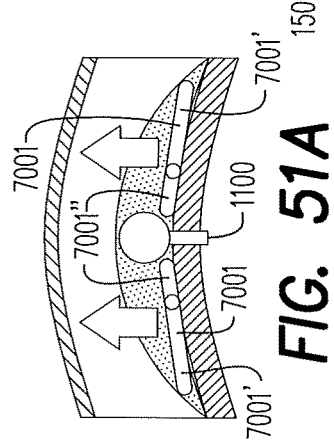

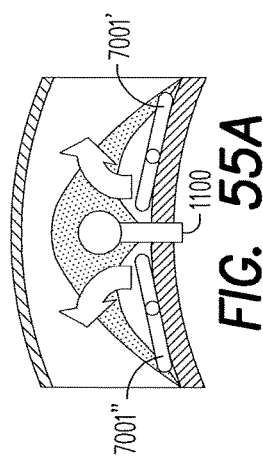
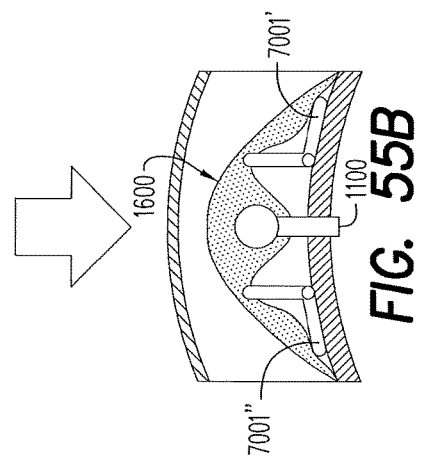
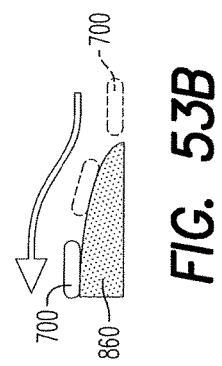
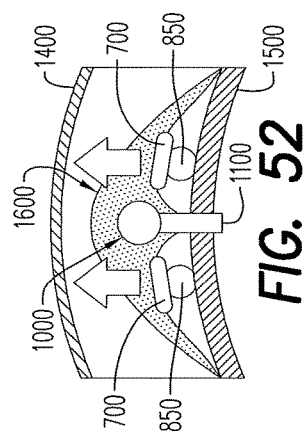
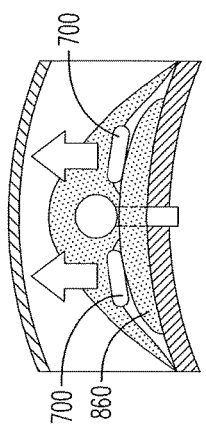
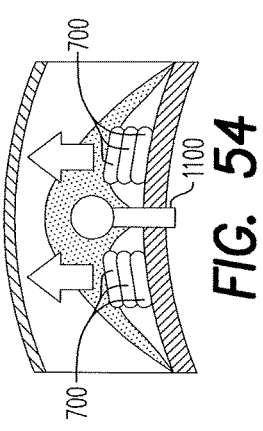

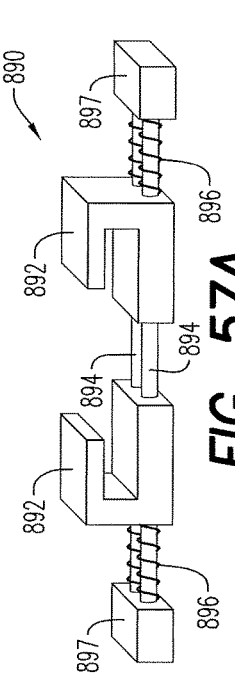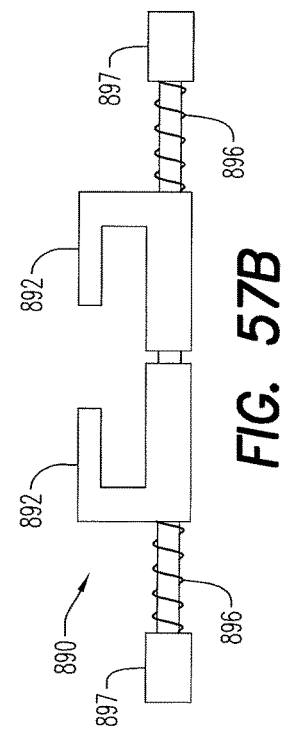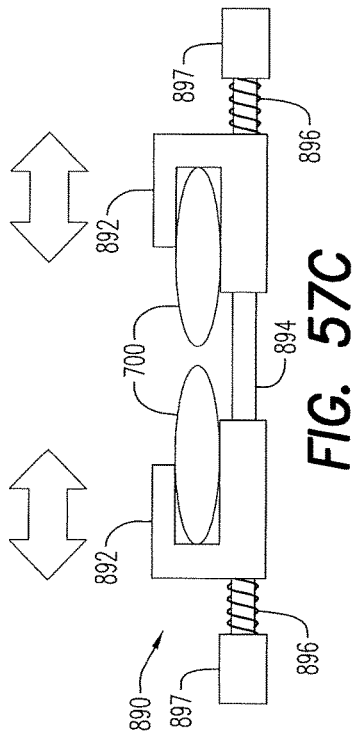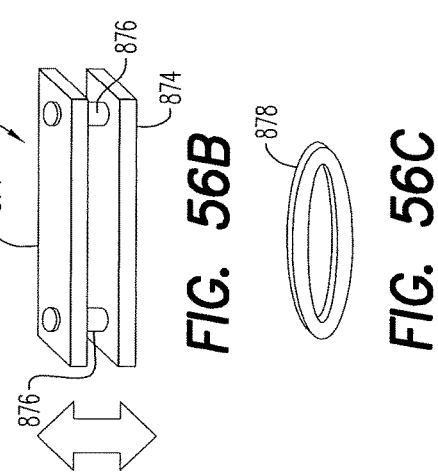

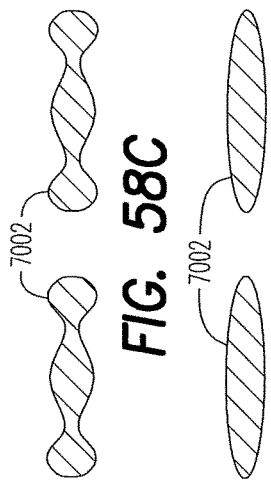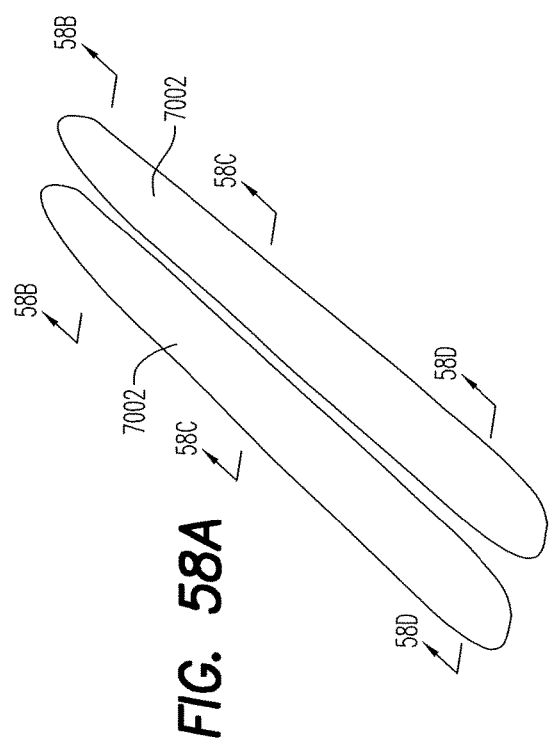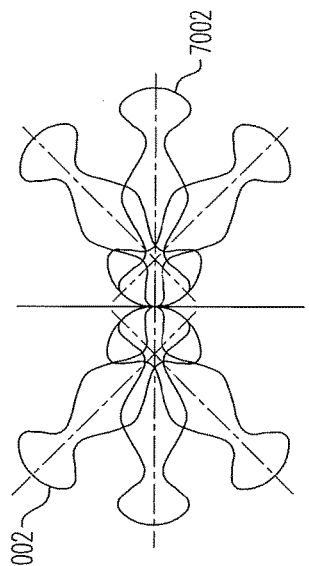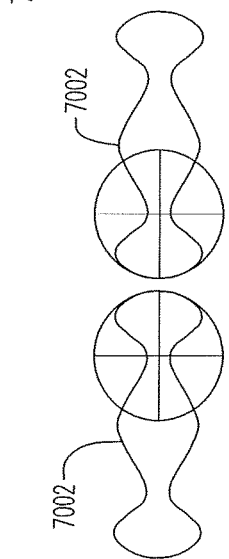

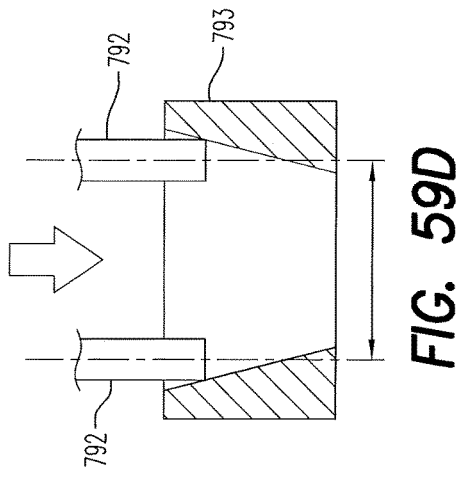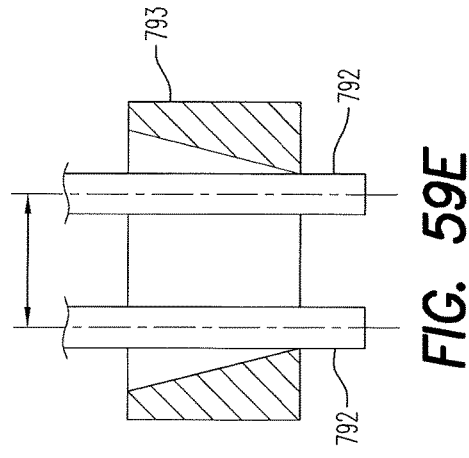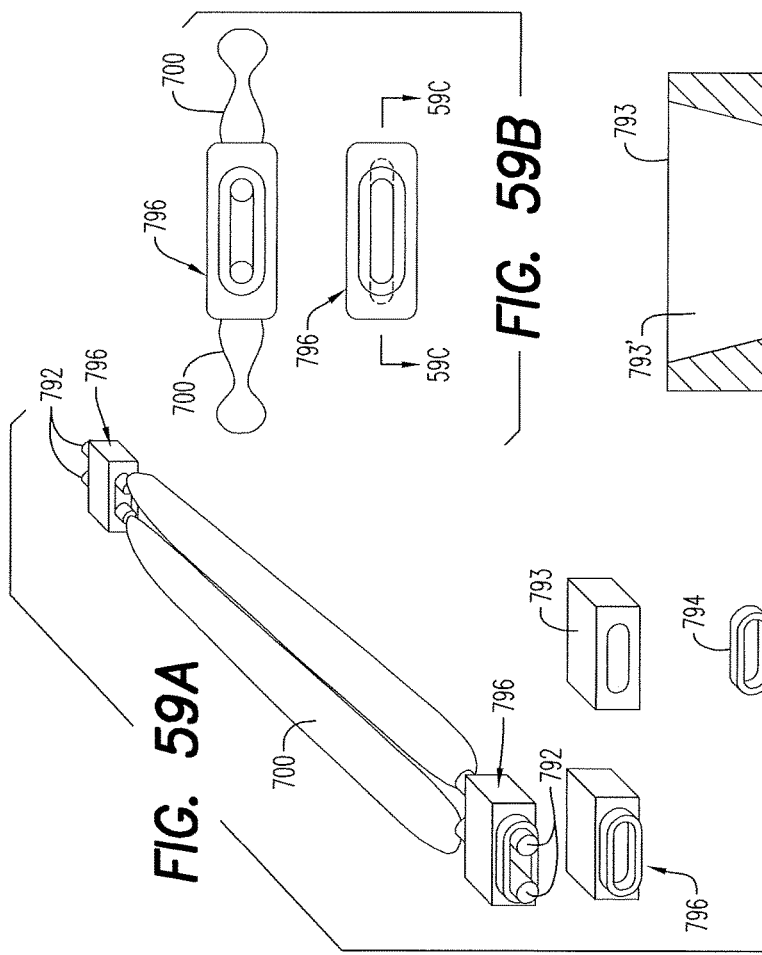

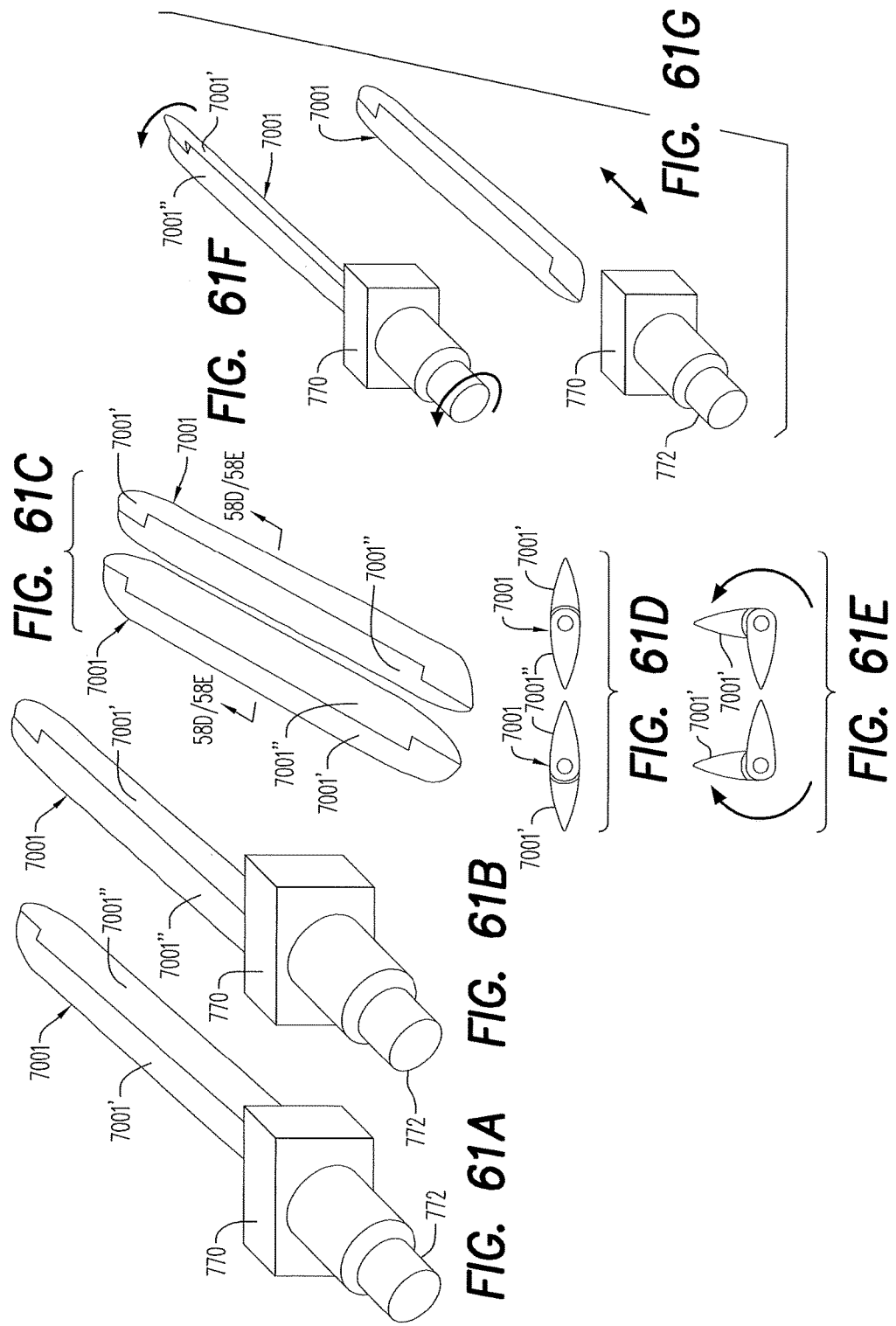

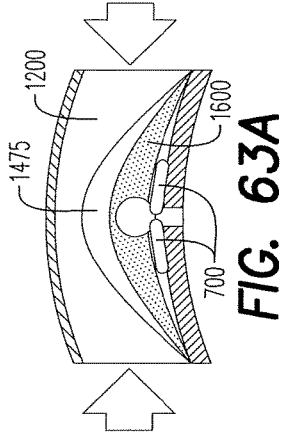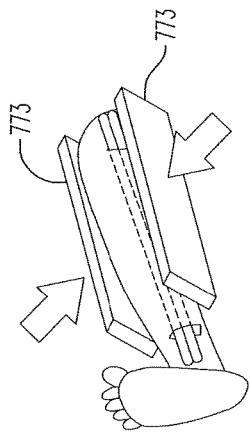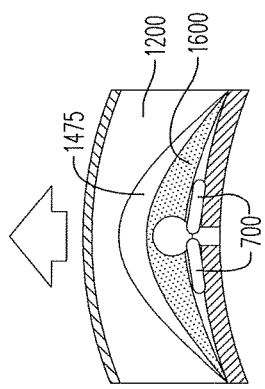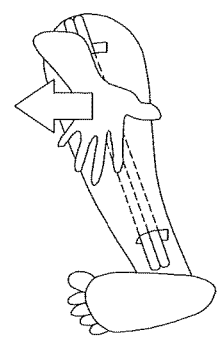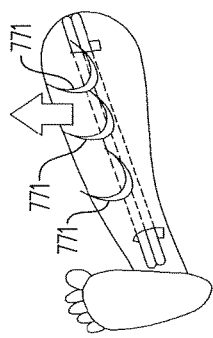

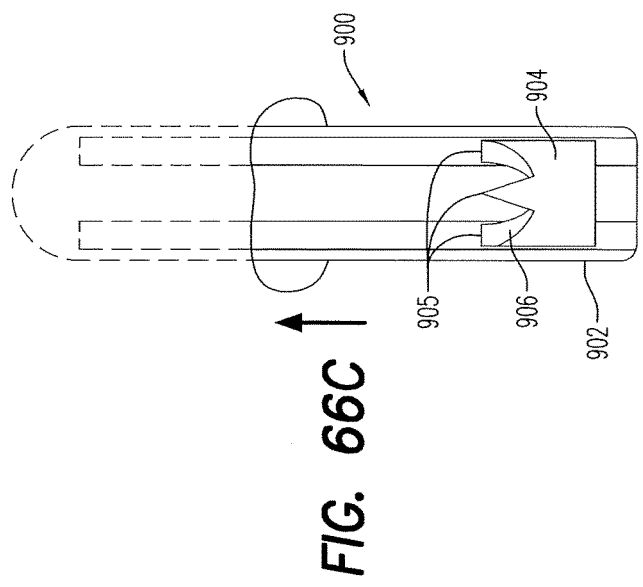
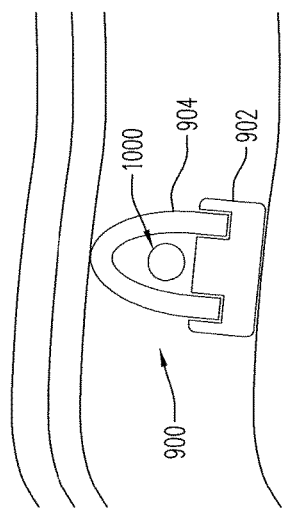
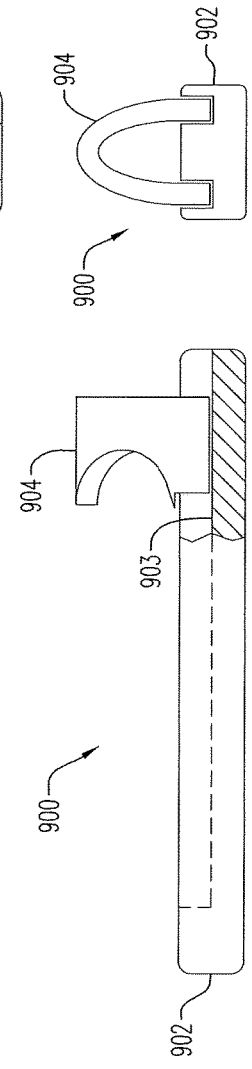
FIG. 66C
FIG. 66D
FIG. 66B
FIG. 66A

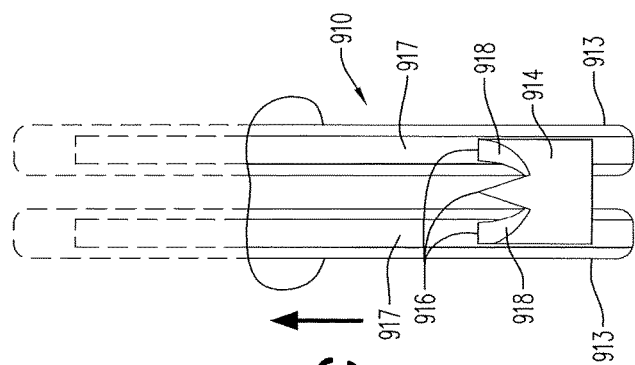
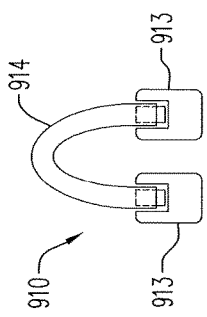
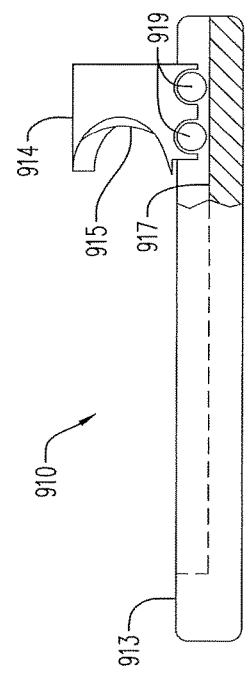
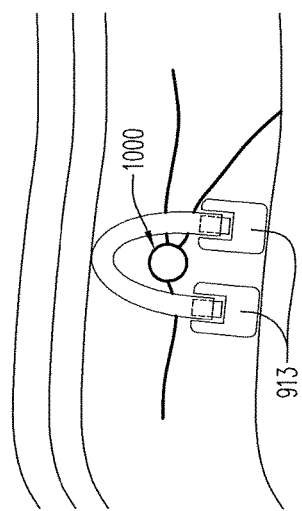
FIG. 67C
FIG. 67D
FIG. 67B
FIG. 67A

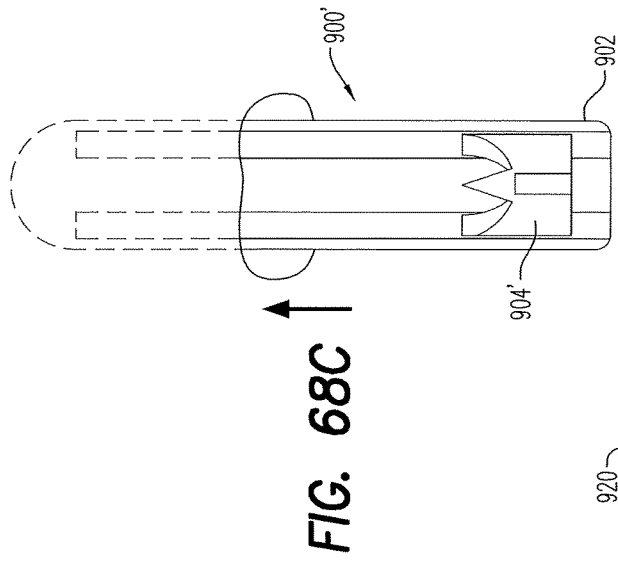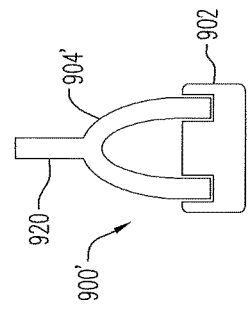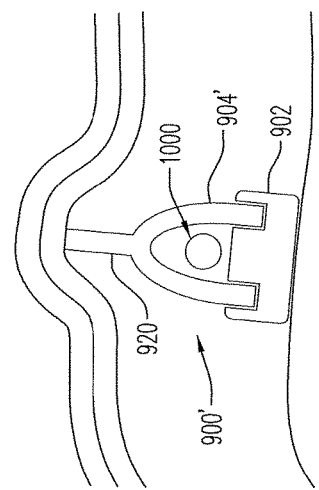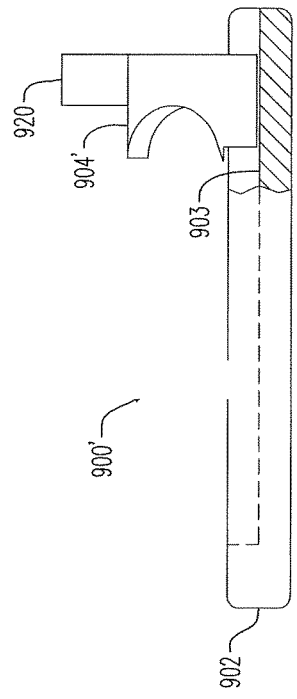

MEDICAL DEVICE AND METHOD

TECHNICAL FIELD

The present disclosure relates to a blood vessel dissecting device and a blood vessel dissecting method.

BACKGROUND DISCUSSION

It is known to use an artery graft represented by internal thoracic artery, gastroepiploic artery and radial artery or a vein graft represented by great saphenous vein as a bypass vessel in performing vascular bypass grafting at the heart (coronary artery bypass grafting: CABG). Besides, at present, it has been reported that artery grafts (particularly, internal thoracic artery) offer higher long-term patency rates than vein grafts. Thus, vein grafts are commonly said to be poor in long-term patency rate. In recent years, however, it has been reported that the long-term patency rate concerning a vein graft is enhanced when the vein graft is harvested in the state of being covered with the surrounding tissue (for example, fat, connective tissue, tissue between a skin layer and a muscle layer, tissue between a skin layer and an interosseous membrane, branch vessels, etc.) and is used as a bypass vessel while remaining covered with the tissue.

Generally speaking, there are two primary techniques for harvesting blood vessels. One technique is referred to as open vein harvesting. This technique involves making an elongated incision along, for example, the patient's limb (leg), and then carrying out the harvesting procedure for removing the blood vessel from the patient's limb. This technique has been found to be somewhat problematic in that it is rather invasive, requiring a rather extensive incision in the patient's limb. Harvesting site complications (e.g., infections) are also not uncommon.

Another technique is referred to as endoscopic vein harvesting. This technique has some advantages over open vein harvesting in that the endoscopic vein harvesting is less invasive and has been found to have a lower incidences of infection. Unfortunately, endoscopic vein harvesting exhibits a lower patency rate because the harvested vein tends to be more damaged.

SUMMARY

The devices and methods disclosed here provide a technique having an improved patency rate similar to the patency rate with the open vein harvesting, but without the harvesting site complications. The technique disclosed here is referred to as a no-touch technique. This technique improves endothelial integrity while reducing injury to the blood vessel (vein). It has also been found that this technique delays arterial atherosclerotic processes, conserves the vasa vasorum and it promotes the nitric oxide synthase activity of endothelial cells According to one aspect, a method for harvesting a vein in a living body comprises: providing an access site permitting access to a vein located inside a living body from outside the living body; exposing at the access site a tissue layer surrounding the vein; inserting a distal end of a flat elongated dissecting device into the living body by way of the access site, with the flat elongated dissecting device possessing a thickness; and moving the flat elongated dissecting device so that a surface of the flat elongated dissecting device contacts the tissue layer surrounding the vein, and continuing to move the flat elongated dissecting device while maintaining the surface of the flat elongated dissecting device in contact with the tissue layer to dissect the tissue layer surrounding the vein from adjacent tissue in a direction of the thickness of the flat elongated dissecting device. The adjacent tissue from which the tissue layer surrounding the vein is dissected differs from the tissue layer surrounding the vein. The method also includes removing from the living body the vein that has been dissected from the adjacent tissue together with the tissue layer surrounding the vein.

Another aspect involves a method for dissecting tissue bound to a vein in a living body from other tissue adjacent the tissue that is bound to the vein. The method involves: creating an access site permitting access, from outside the living body, to the tissue bound to the vein located inside the living body; exposing by way of the access site the tissue that is bound to the vein; inserting a distal end of a flat elongated dissecting device into the living body by way of the access site, the flat elongated dissecting device possessing a thickness; moving the flat elongated dissecting device so that a surface of the flat elongated dissecting device contacts the tissue that is bound to the vein; and continuing to move the flat elongated dissecting device while maintaining the surface of the flat elongated dissecting device in contact with the tissue that is bound to the vein to dissect the tissue that is bound to the vein from the other tissue in a direction of the thickness of the flat elongated dissecting device. The tissue bound to the vein is different from the other tissue.

BRIEF DESCRIPTION OF THE DRAWINGS

FIGS. 2A and 2B illustrate a dissecting device forming a part of the blood vessel dissecting device shown in FIG. 1, wherein FIG. 2A is a longitudinal cross-sectional view and FIG. 2B is a transverse cross-sectional view taken along the section line 2B-2B of FIG. 2A.

FIGS. 3A and 3B illustrate a cutting device forming a part of the blood vessel dissecting device shown in FIG. 1, wherein FIG. 3A is a plan view and FIG. 3B is a cross-sectional view taken along the section line 3B-3B of FIG. 3A.

FIGS. 4A and 4B show views explaining a blood vessel dissecting method carried out using the blood vessel dissecting device shown in FIG. 1.

FIGS. 12A to 12C illustrate a dissecting device forming a part of a blood vessel dissecting device according to a sixth embodiment of the present disclosure, wherein FIG. 12A is a top plan view, FIG. 12B is a side view, and FIG. 12C is a top plan view showing the dissecting device in the state of being used.

FIGS. 13A and 13B illustrate a dissecting device forming a part of a blood vessel dissecting device according to a seventh embodiment of the present disclosure, wherein FIG. 13A is a top plan view and FIG. 13B is a top plan view showing the dissecting device in the state of being used.

FIG. 15A illustrates a great saphenous vein, and FIG. 15B is a plan view of a dissecting device forming a part of a blood vessel dissecting device according to a ninth embodiment of the present disclosure.

FIGS. 16A and 16B are plan views of a dissecting device forming a part of a blood vessel dissecting device according to a tenth embodiment of the present disclosure.

FIGS. 17A and 17B are plan views of a dissecting device forming a part of a blood vessel dissecting device according to an eleventh embodiment of the present disclosure.

FIG. 20A illustrates a leg of a living body and depicts the great saphenous vein 1000 extending from the upper leg to the lower leg, FIGS. 20B and 20C depict cross-sections of the upper leg and the lower leg respectively, including the great saphenous vein, and FIG. 21A and FIG. 21B are enlarged schematic illustrations of the noted portions of FIGS. 20B and 20C respectively.

FIGS. 23A-23C and 23B1 depict a manner of dissecting tissue using the dissecting device shown in FIGS. 22A-22C.

FIGS. 24A and 24B illustrate a result of as dissecting operation.

FIGS. 29A and 29B illustrate a different dissecting device, and FIGS. 29C-29E depict aspects of a dissecting procedure.

FIGS. 30A-30D show modified version of a dissecting device.

FIGS. 31A and 31B show aspects of another dissecting procedure.

FIGS. 34-37 depict a dissecting device according to another embodiment and a manner of using such dissecting device.

FIGS. 42A-42C, 43A-43C, 44A-44C, 45A, 45B and 46 depict another embodiment of a dissecting device.

FIG. 48 illustrate a dissecting device.

FIGS. 49A-49H show cross-sections of different versions of a dissecting device.

FIGS. 50A-50D illustrate aspects of another embodiment of a dissecting device and a dissecting procedure using the dissecting device.

FIGS. 51A-51D illustrate aspects of an additional embodiment of a dissecting device and a dissecting procedure using the dissecting device.

FIG. 52 shows a modified aspect of a dissection procedure.

FIGS. 53A and 53B illustrate another modified aspect of a dissection procedure.

FIG. 54 shows an additional modified aspect of a dissection procedure.

FIGS. 55A and 55B illustrate another modified aspect of a dissection procedure.

FIGS. 56A-56C illustrate features of a dissecting device useful in retaining the side branch in a held state.

FIGS. 57A-57C illustrate features of another dissecting device useful in retaining the side branch in a held state.

FIGS. 58A-58F show features of another dissecting device.

FIGS. 59A-59E illustrate features of a dissecting device useful in the operational procedure shown in FIGS. 50A-50D.

FIGS. 61A-61G illustrate features of a dissecting device useful in the operational procedure shown in FIGS. 51A-51D.

FIGS. 62A-62C show aspects of operational procedures for holding parts of the limb.

FIGS. 63A-63C show aspects of other operational procedures for holding parts of the limb.

FIGS. 66A-66D illustrate features of another embodiment of a dissecting device.

FIGS. 67A-67D illustrate features of an additional embodiment of a dissecting device.

FIGS. 68A-68D illustrate features of a further embodiment of a dissecting device.

DETAILED DESCRIPTION

Examples of a blood vessel dissecting device and a blood vessel dissecting method disclosed here will be described in detail below, referring to the attached drawings.

First Embodiment

FIGS. 1-5B illustrate a blood vessel dissecting device and blood vessel dissecting method carried out using the blood vessel dissecting device according to a first embodiment representing one example of the disclosure here. In the following description, for convenience of explanation, the right side in FIG. 1 will be referred to as "distal" side or end, and the left side in the figure as "proximal" side or end.

Blood Vessel Dissecting Device

Figure 1:
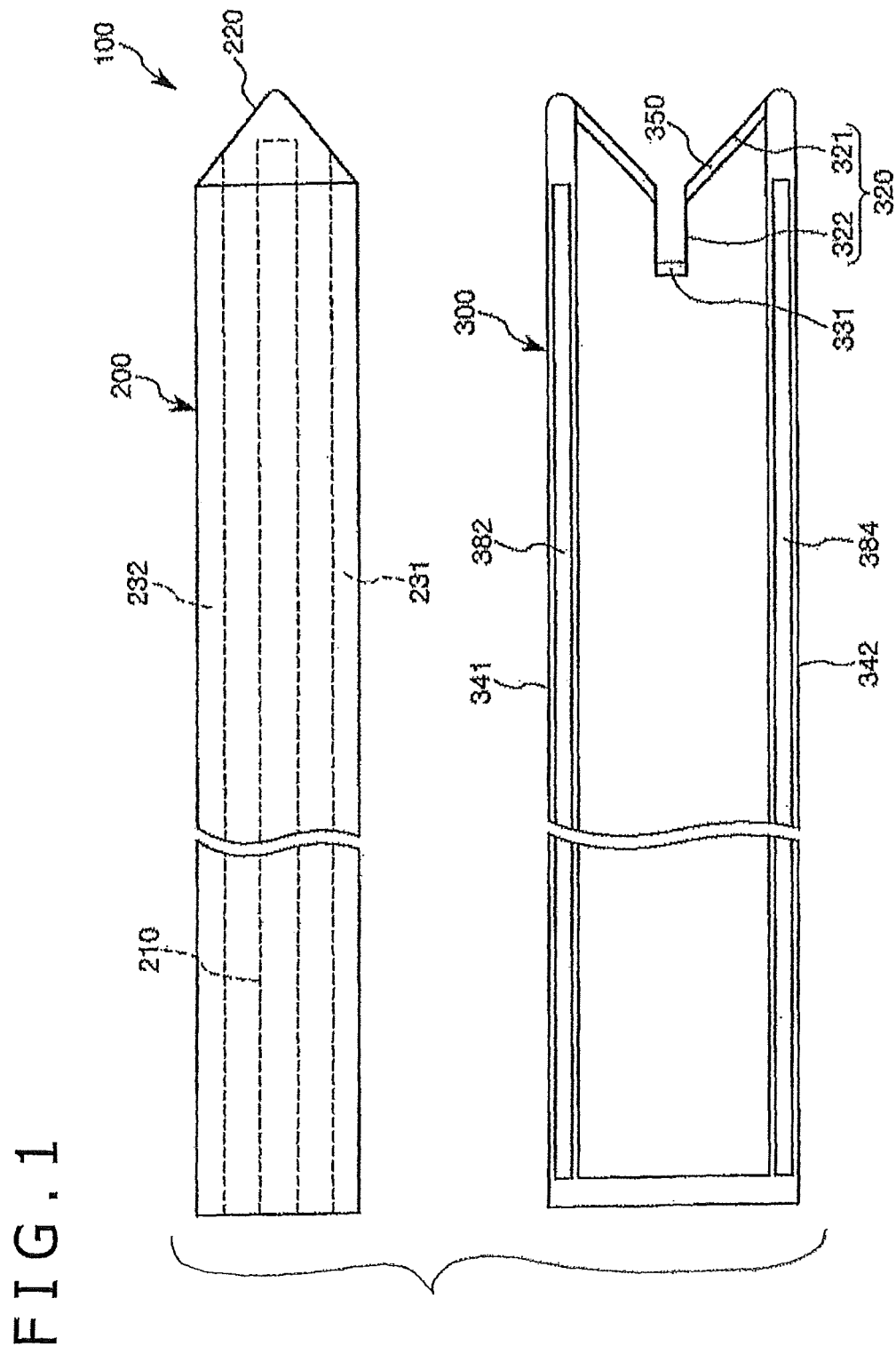
FIG. 1 is a plan view of a blood vessel dissecting device according to a first embodiment of the present disclosure.

A blood vessel dissecting device 100 shown in FIG. 1 is a device used to harvest a blood vessel for use as a bypass vessel in carrying out blood vessel bypass grafting (particularly, coronary artery bypass grafting: CABG). By use of the blood vessel dissecting device 100, a blood vessel can be harvested in the state of being covered with the surrounding tissue (fat, connective tissue, etc.), preferably to the extent that the blood vessel is not exposed to the surface of the surrounding tissue and the blood vessel does not have the lateral surface that is exposed to the external atmosphere. More preferably, to the extent that an outer surface of the blood vessel is not exposed to the surface of the surrounding tissue and the outer surface of the blood vessel does not have the lateral surface that is exposed to the external atmosphere. Note that the blood vessel to be harvested using the blood vessel dissecting device 100 is not particularly limited insofar as it is a blood vessel that can be used as a bypass vessel. Examples of the applicable blood vessel include internal thoracic artery, gastroepiploic artery, radial artery, and great saphenous vein.

It is preferable, however, that the blood vessel to be harvested is the great saphenous vein. As aforementioned, the use of the blood vessel dissecting device 100 facilitates harvesting of a blood vessel in the state in which the blood vessel is covered with the surrounding tissue. When the great saphenous vein is harvested by using the blood vessel dissecting device 100 and is used as a bypass vessel, therefore, it is considered that an enhanced long-term patency rate is obtained after the bypass grafting operation. In view of this, in the following, an example of harvesting a great saphenous vein by use of the blood vessel dissecting device 100 will be described on a representative basis.

As shown in FIG. 1, the blood vessel dissecting device 100 includes a dissecting device 200 and a cutting device 300. Both the dissecting device 200 and the cutting device 300 are devices which are inserted into a living body along the great saphenous vein. The dissecting device 200 and the cutting device 300 will now be described in detail below.

Dissecting Device

The dissecting device 200 has an elongated bar-like shape (bar-shaped) extending substantially straight, and is provided at its distal end with a dissecting section 220 for dissecting tissue. In addition, as shown in FIG. 2B, the dissecting device 200 has a flat shape (flattened shape as seen in vertical cross-section to a central axial direction of the dissecting device) in section. The cross-sectional shape of the dissecting device 200 is not specifically restricted; for example, the cross-sectional shape may be a crushed-circle-like shape (flattened circular shape), such as an oblong and an ellipse, a rectangle rounded at corners, or the like.

The width (the length in the major axis direction of the cross-sectional shape) W1 of the dissecting device 200 is greater than the outside diameter of the blood vessel to be harvested (in this embodiment, the great saphenous vein). To be more specific, the width W1 is preferably about 4 mm to 2 cm greater than the outside diameter of the blood vessel to be harvested. This helps ensure that the possibility of contact between the cutting device 300 and the great saphenous vein can be effectively lowered at the time of inserting the cutting device 300 into the living body along the dissecting device 200, as will be explained in the "blood vessel harvesting method" described later.

In addition, the dissecting device 200 is provided, at both ends of the major axis of the cross-sectional shape thereof, with rails 231 and 232 in the form of linear stretches of recess (or trenches/grooves) which extend in the axial direction of the dissecting device 200. Each of the rails 231 and 232 is used for connection of the dissecting device 200 with the cutting device 300, and functions as a guide section for guiding the cutting device 300. Note that the rails 231 and 232 are not limited to the linear stretches of recess (or trenches/grooves) but may be, for example, linear stretches of projection (or ridges or ribs), insofar as they each enable connection of the dissecting device 200 with the cutting device 300.

As shown in FIG. 2A, the dissecting device 200 is provided with an insertion hole 210 which opens at the proximal end and extends to a distal portion (the dissecting section 220). In this illustrated embodiment, the insertion hole 210 is a blind hole, meaning the insertion hole 210 is closed at its distal end. Into the insertion hole 210 is inserted an imaging device 400. The imaging device 400 is not specifically restricted. For example, the imaging device 400 in this embodiment, as depicted in FIG. 2A, includes an elongated main body section 410, and an illuminating section (not shown) for emitting illumination light and an imaging section 430 for imaging the front side of the dissecting device 200. The illuminating section and the imaging section 430 are disposed at a distal portion of the main body section 410. The imaging section 430 includes, for example, an objective lens system disposed at the distal portion of the main body section 410 and an imaging element (e.g., solid state image sensor such as CMOS image sensor or CCD sensor) disposed opposite to the objective lens system.

The dissecting section 220 is tapered in a narrowing manner toward the distal end of the dissecting device 200. More specifically, the distal end portion of the dissecting section 220 possesses a tapered roughly conical shape so that the length in the minor axis direction and the length in the major axis direction of the cross-sectional shape of the dissecting section 220 are both gradually decreased in a direction toward the distal end. Such a dissecting section 220 is blunt in the thickness direction, and has such a degree of sharpness (bluntness) as to be able to dissect tissues having different properties (for example, fat and skin, fat and fascia, fat and blood vessel, fat and bone, etc.) from each other without cutting branch vessels branched from the great saphenous vein. This helps ensure that a dissecting function can be sufficiently exhibited and the branch vessels are restrained from being damaged or cut by the dissecting section 220. Accordingly, bleeding can be suppressed, and the intended technique can be performed safely and smoothly. Note that the shape of the dissecting section 220 is not particularly limited insofar as it enables dissection of tissues in the thickness direction (minor axis direction) of the tissues. For example, the dissecting section 220 may be in the shape of a duck-bill such that the length in the minor axis direction of the cross-sectional shape of the dissecting section 220 is gradually decreased (tapered) toward the distal end and the cross-sectional shape at the distal end is a line segment along the major axis direction.

The dissecting section 220 is substantially colorless and transparent and is light-transmitting. This helps ensure that when the imaging device 400 is inserted into the insertion hole 210, the front side of the dissecting device 200 can be observed through the dissecting section 220 by the imaging device 400. In other words, the dissecting section 220 has the function as an observation section for observation of the inside of the living body (the great saphenous vein and its surroundings), in addition to the aforementioned function as the dissecting section. Note that the dissecting section 220 is not limited to the colorless transparent property but may be colored in red, blue, green or the like, insofar as it is light-transmitting.

Cutting Device

The cutting device 300, at the time of moving along a great saphenous vein 1000, cuts the fat (inclusive of connective tissue) surrounding the great saphenous vein 1000 and, in addition, cuts and stanches the branch vessels branched from the great saphenous vein 1000.

Figure 3A:
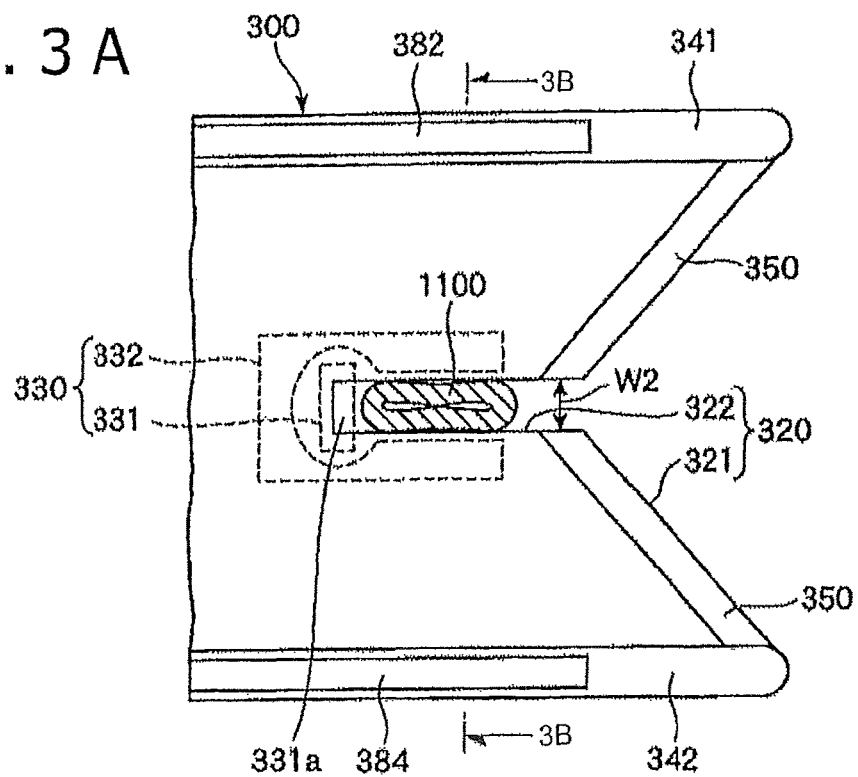

The cutting device 300 is elongated plate-like in shape (plate-shaped). As shown in FIGS. 1 and 3A, the cutting device 300 has a groove portion 320 opening in a distal portion of the cutting device. The groove portion 320 includes: a tapered blood vessel guide groove section (first groove section) 321 having a width gradually decreasing toward the proximal side; and a straight blood vessel treating groove section (second groove section) 322 which is located on the proximal side of the blood vessel guide groove section 321 and is substantially constant in width. The blood vessel guide groove section 321 is a groove section for guiding a branch vessel into the blood vessel treating groove section 322 at the time of pushing the cutting device 300 forward in a living body, and is tapered in shape for the guiding to be smoothly achieved. On the other hand, the blood vessel treating groove section 322 is a groove section for cutting and stanching the branch vessel guided to the blood vessel treating groove section 322 by the blood vessel guide groove section 321. Further, the blood vessel treating groove section 322 is provided with a treating section 330 for cutting and stanching a branch vessel.

As shown in FIG. 3A, the treating section 330 has a bipolar structure including a pair of electrodes 331 and 332 configured to generate an electric field inside the blood vessel treating groove section 322. The electrode 331 is disposed at a proximal end portion of the blood vessel treating groove section 322, while the electrode 332 is disposed on both sides with respect to the width direction of the blood vessel treating groove section 322. With a high-frequency AC voltage impressed between the electrodes 331 and 332, it is possible to heat and cut a branch vessel 1100 guided into the blood vessel treating groove section 322 and to stanch the blood vessel through thermal coagulation. A distal portion (a portion exposed to the blood vessel treating groove section 322) 331a of the electrode 331 is preferably so sharp as to be able to cut the branch vessel 1100. This helps ensure that if thermal coagulation (stanching) of the branch vessel 1100 can at least be achieved by the electric field generated between the electrodes 331 and 332, the branch vessel 1100 can be physically cut by the distal portion 331a of the electrode 331. Accordingly, the assuredness of the treatment by the treating section 330 is enhanced.

The width W2 of the blood vessel treating groove section 322 is not particularly limited but it is preferably narrower than the outside diameter of the branch vessel 1100. This helps ensure that the branch vessel 1100 can be pressed flat inside the blood vessel treating groove section 322 as shown in FIG. 3A, and, consequently, the treatment (cutting and stanching) at the treating section 330 can be performed more reliably.

The cutting device 300 is provided with a cutting edge section (cutting section) 350 for cutting the fat surrounding the great saphenous vein 1000. The cutting edge section 350 is disposed at a distal portion of the cutting device 300; in this embodiment, it is disposed along the blood vessel guide groove section 321. As will be explained also in the "blood vessel harvesting method" described later, the cutting edge section 350 has the function of cutting the fat surrounding the great saphenous vein 1000 at the time of pushing the cutting device 300 forward in the living body. Such a cutting edge section 350 preferably has such a sharpness as to be able to cut the fat without cutting the branch vessel 1100. This helps ensure that cutting of the branch vessel 1100 by the cutting edge section 350 is inhibited, so that bleeding is restrained, and the intended technique can be performed safely and smoothly.

Figure 3B:
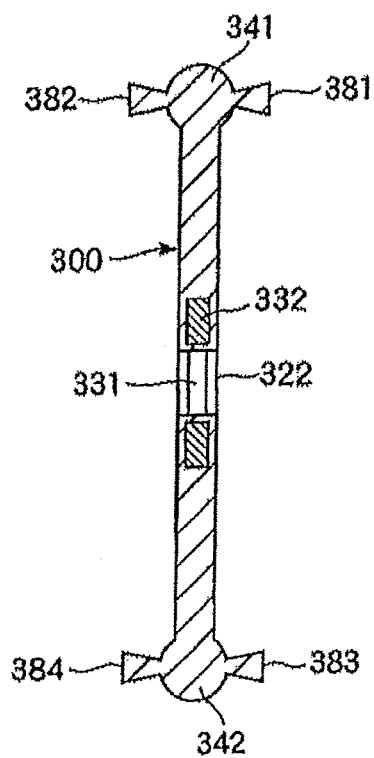

As shown in FIG. 3B, the cutting device 300 has a pair of protection sections 341 and 342 provided on both sides with respect to the cutting device's width direction (the direction orthogonal to its moving direction). The protection sections 341 and 342 each extend along the axial direction of the cutting device 300, and their peripheral surfaces (side surfaces and distal surfaces) are rounded. As will be explained also in the "blood vessel harvesting method" described later, the protection section 341 moves along and between fat and skin while dissecting them from each other, at the time of pushing the cutting device 300 toward the distal side in a living body. Since the fat and the skin having different properties, they are rather easy to dissect from each other, even though a distal end portion of the protection section 341 is rounded, and the dissecting function of dissecting the fat and the skin from each other can be exhibited sufficiently. In addition, the rounding helps ensure that a branch vessel can be restrained from being damaged or cut by the protection section 341, and, further, damage to (cauterization of) the skin due to sliding against (friction with) the protection section 341 can be restrained. Similarly, the protection section 342 moves along and between the fat and the fascia while dissecting them from each other at the time of pushing the cutting device 300 toward the distal side in the living body. Since the fat and the fascia having different properties, they are easy to dissect from each other, even though a distal end portion of the protection section 342 is rounded, and the dissecting function of dissecting the fat and the fascia from each other can be exhibited sufficiently. Besides, the rounding helps ensure that the branch vessel can be restrained from being damaged or cut by the protection section 342, and, further, damage to (cauterization of) the fascia due to sliding against (friction with) the protection section 342 can be restrained.

As shown in FIGS. 3A and 3B, the cutting device 300 has connection sections 381, 382, 383 and 384 configured to connect with the rails 231 and 232 of the dissecting device 200. The connection sections 381 and 382 are provided at the protection section 341, and disposed on mutually opposite surface sides. Similarly, the connection sections 383 and 384 are provided at the protection section 342, and disposed on mutually opposite surface sides. These connection sections 381 to 384 are composed of stretches (lengths) of projection (or ridges or ribs) which extend in the axial direction of the cutting device 300 and correspond to the stretches of recess (trenches) of the rails 231 and 232. Since such connection sections 381 to 384 are provided, unintended detachment of the dissecting device 200 and the cutting device 300 from each other is prevented, so that the intended technique can be carried out more smoothly and accurately. Thus, in this example of the blood vessel dissecting device, both the cutting device 300 and the dissecting device 200 include connection structure configured to connect the cutting device 300 and the dissecting device 200 to each other.

Blood Vessel Harvesting Method

A method of harvesting a blood vessel by use of the blood vessel dissecting device 100 includes: a first step (blood vessel dissecting method) of dissecting the great saphenous vein 1000 in the state of being covered with surrounding fat 1200 by use of the blood vessel dissecting device 100; a second step of ligating the great saphenous vein 1000 and then cutting the great saphenous vein 1000; and a third step of extracting the great saphenous vein 1000 in the state of being covered with the surrounding fat 1200 from the living body.

First Step

First, the position of the great saphenous vein 1000 to be harvested is confirmed, and skin is incised on the basis of the position of the great saphenous vein. Next, the dissecting device 200 with the imaging device 400 inserted in the dissecting device 200 is prepared, and, while observing the inside of the living body by the imaging device 400, the dissecting device 200 is inserted from the incision 1300 into the living body along the great saphenous vein 1000 while keeping the dissecting device 200 spaced from the great saphenous vein 1000. Then, as shown in FIG. 4A, the dissecting device 200 is disposed on the upper side (the skin 1400 side) of the great saphenous vein 1000. In this case, the dissecting device 200 is so disposed that the thickness direction of the dissecting device 200 agrees substantially with the aligning direction in which the dissecting device 200 and the great saphenous vein 1000 are aligned. In this operation, the dissecting device 200 is inserted between the fat 1200 and the skin 1400 (between the tissues having different properties), and the skin 1400 and the fat 1200 are dissected from each other in the thickness direction of the dissecting device 200 (in the aligning direction in which the dissecting device 200 and the great saphenous vein 1000 are aligned). Such an area is an area where dissection can be achieved particularly easily, so that this operation can be carried out more smoothly and accurately. The dissecting device 200 thus dissects tissue in a direction along the longitudinal extent of the vein.

Subsequently, the cutting device 300 is prepared, and the connection section 381 is connected to the rail 231 of the dissecting device 200. Then, the state of the dissecting device 200 is aligned on the upper side of the great saphenous vein 1000, the cutting device 300 is inserted into and moved in the living body while guiding the cutting device 300 with the dissecting device 200 as shown in FIG. 4B. In this case, the cutting device 300 is moved forward while dissecting the skin 1400 from the fat 1200 by the protection section 341, and while dissecting the fascia 1500 from the fat 1200 by the protection section 342. Furthermore, the cutting device 300 cuts the fat 1200 present on the one lateral side of the great saphenous vein 1000 by the cutting edge section 350 in the left-right direction (in the aligning direction in which the cutting device 300 and the great saphenous vein 1000 are aligned), and, concurrently, cuts and stanches the branch vessel 1100 by the treating section 330.

Here, since the width W1 of the dissecting device 200 is greater than the outside diameter of the great saphenous vein 1000 as aforementioned, the cutting device 300 can be pushed forward along the great saphenous vein 1000 while keeping the cutting device 300 laterally spaced from the great saphenous vein 1000, as shown in FIG. 4B, so that the great saphenous vein 1000 can be prevented from being damaged during this operation. In addition, since the protection sections 341 and 342 are rounded, the possibility of damaging the skin 1400 or the fascia 1500 by contact with the cutting device 300 is lowered.

Next, the cutting device 300 is drawn out, and the connection section 382 of the cutting device 300 thus drawn out is connected to the rail 232 of the dissecting device 200.

Figure 5A:
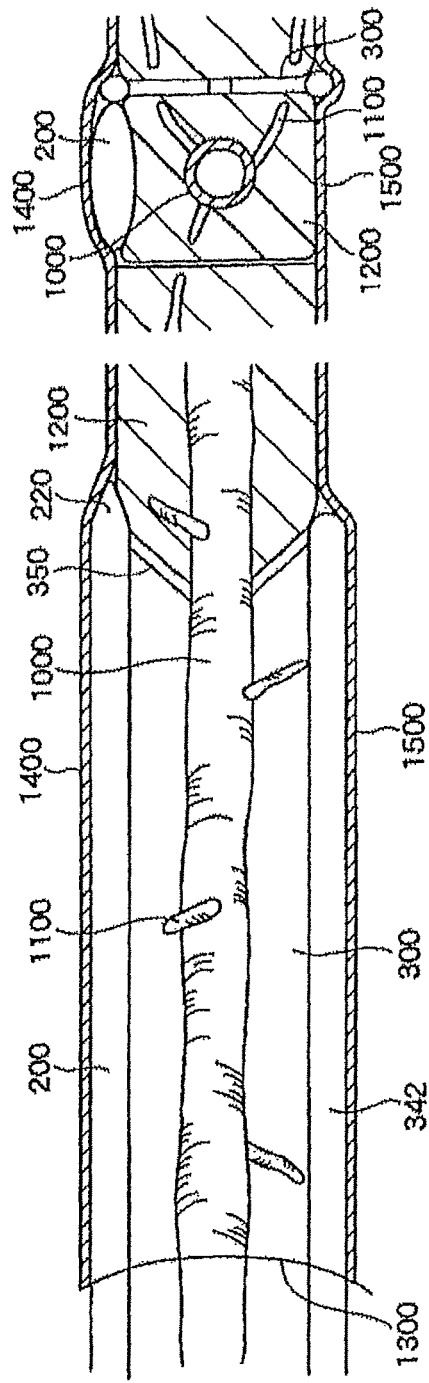
FIGS. 5A and 5B show views explaining the blood vessel dissecting method carried out using the blood vessel dissecting device shown in FIG. 1.

Then, the cutting device 300 is inserted again into the living body while guiding the cutting device 300 with the dissecting device 200, to dispose the cutting device 300 on the other lateral side of the great saphenous vein 1000, as shown in FIG. 5A.

Figure 5B:
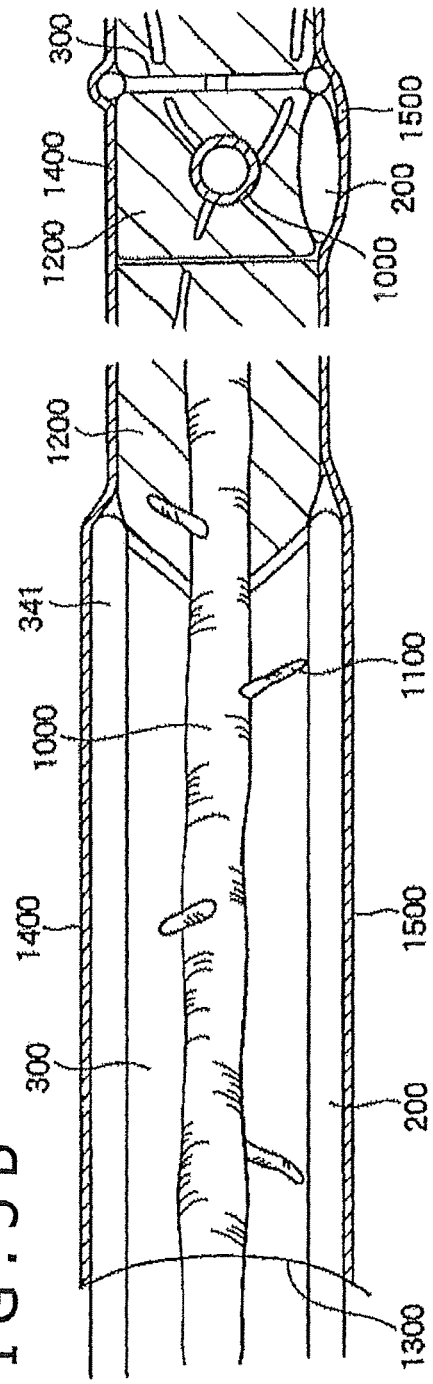

Subsequently, the dissecting device 200 is drawn out, and the rail 232 of the dissecting device 200 thus drawn out is connected to the connection section 384 of the cutting device 300. Then, the dissecting device 200 is inserted again into the living body while guiding the dissecting device 200 with the cutting device 300, to dispose the dissecting device 200 on the lower side (the fascia 1500 side (bone side)) of the great saphenous vein 1000, as shown in FIG. 5B. In this operation, the dissecting device 200 is inserted between the fat 1200 and the fascia 1500 (inserted into the boundary between the tissues having different properties), and the fat 1200 and the fascia 1500 are dissected from each other in the thickness direction of the dissecting device 200. Such an area is an area where dissection can be particularly easily achieved, so that this operation can be carried out more smoothly and accurately.

By the above-mentioned operations, the fat 1200 surrounding the great saphenous vein 1000 is dissected over the entire perimeter of the vein, and the great saphenous vein 1000 is dissected in the state of being covered with the surrounding fat 1200. The thickness of the fat 1200 dissected together with the great saphenous vein 1000 and located in the surroundings of the great saphenous vein 1000 is not particularly limited. It is preferable, however, that the thickness is about 0.1 mm to 10 mm, more preferably about 1 mm to 8 mm, and further preferably about 3 mm to 5 mm.

Second Step

Next, both ends of that part of the great saphenous vein 1000 which is to be harvested are ligated and then cut.

Third Step

Subsequently, the great saphenous vein 1000 is extracted in the state of being covered with the surrounding fat 1200, to the outside of the living body via the incision 1300.

By the first to third steps as above-mentioned, the great saphenous vein 1000 can be harvested while the great saphenous vein is in the state of being covered with the surrounding fat 1200. In such a method, while using the dissecting device 200 for treating a part which is rather easy to dissect so as to reduce such damages as bleeding and while using the cutting device 300 for treating the fat which is difficult to dissect, the great saphenous vein 1000 can be harvested smoothly and with low invasion. In addition, since the first step can be carried out without cutting the great saphenous vein 1000, blood can be kept flowing through the great saphenous vein 1000 for a time as long as possible. Accordingly, the great saphenous vein 1000 is placed in an ischemic state for a shortened period of time, so that the great saphenous vein 1000 can be harvested with less damage.

Here, a great saphenous vein 1000 covered with fat 1200 constitutes a bypass vessel having a superior long-term patency rate, as compared with a great saphenous vein 1000 not covered with fat 1200. The reason is considered as follows. While the great saphenous vein 1000 is used as an artery bypass vessel, arteries are generally higher than veins in the blood pressure (the internal pressure exerted thereon by blood). When a great saphenous vein in an exposed state of being not covered with tissue is used as a bypass vessel, therefore, the great saphenous vein cannot endure the blood pressure and is therefore expanded by the blood pressure, resulting in lowered blood flow. In addition, thickening of blood vessel wall occurs in the process of remodeling (structural alteration) or in the process of recovery from damage to tissue. Such thickening of blood vessel wall is considered to influence the development of arterial sclerosis. From such a cause, the use of a great saphenous vein in the exposed state of being not covered with tissue as a bypass vessel would, in the long run, lead to vascular occlusion.

On the other hand, where the great saphenous vein 1000 is covered with fat 1200, expansion of the great saphenous vein 1000 is restrained by the fat 1200, and bending and the like of the great saphenous vein 1000 are also restrained. Therefore, the lowering in blood flow as above-mentioned can be inhibited. In addition, the covering with the fat 1200 reduces damages to the great saphenous vein 1000, specifically, damages to endotheliocytes, smooth muscles, nutrient vessels (capillary plexus), etc. Therefore, the aforementioned thickening of blood vessel walls can be restrained. For these reasons, the use of the great saphenous vein 1000 covered with the fat 1200 as a bypass vessel enables an excellent long-term patency rate. Especially, in this embodiment, nutrient vessels are left at the blood vessel walls of the great saphenous vein 1000 and in the fat 1200. For this reason, nutrients are supplied to the great saphenous vein 1000 serving as the bypass vessel, even after the bypass grafting. This is considered to be the reason why the aforementioned effect is enhanced.

While this embodiment has been described, the configuration of the blood vessel dissecting device 100 is not limited to the configuration in this embodiment. For example, the rails 231 and 232 may be omitted from the dissecting device 200, and the connection sections 381 to 384 may be omitted from the cutting device 300. In this case, for example, it may be sufficient to insert the cutting device 300 into a living body along the dissecting device 200 which is inserted into the living body earlier. Alternatively, it may be sufficient to insert the dissecting device 200 into a living body along the cutting device 300 which is inserted into the living body earlier.

The cutting device 300 is not specifically restricted insofar as it can cut the fat 1200. For instance, a configuration may be adopted in which the fat 1200 is cut by something like a pair of scissors.

The blood vessel dissecting method is not limited to the procedure adopted in this embodiment. For instance, the order of insertion of the dissecting device 200 and the cutting device 300 is not specifically restricted, and any of left, right, upper and lower portions of the great saphenous vein 1000 may be dissected first. For instance, a procedure may be adopted in which, first, upper and lower sides of the great saphenous vein 1000 are dissected by use of the dissecting device 200, and, then, left and right sides of the great saphenous vein 1000 are dissected by use of the cutting device 300. On the other hand, left and right sides of the great saphenous vein 1000 may first be dissected by use of the cutting device 300, and, then, upper and lower sides of the great saphenous vein 1000 may be dissected by use of the dissecting device 200.

While one dissecting device 200 and one cutting device 300 are used in this embodiment, two dissecting devices 200 and two cutting devices 300 may be used. In this case, for example, a procedure may be adopted wherein, first, a first dissecting device 200 is disposed on the upper side of the great saphenous vein 1000, next a first cutting device 300 is disposed on one of left and right sides of the great saphenous vein 1000, then a second cutting device 300 is disposed on the other of the left and right sides of the great saphenous vein 1000, and a second dissecting device 200 is disposed on the lower side of the great saphenous vein 1000. Such a procedure eliminates the need to draw out the dissecting device 200 and the cutting device 300 in the course of the procedure, so that the aforementioned procedure can be carried out smoothly.

While the dissecting device 200 is inserted between the fat 1200 and the skin 1400 and between the fat 1200 and the fascia 1500 in this embodiment, the insertion position of the dissecting device 200 is not particularly limited. For instance, the dissecting device 200 may be inserted between tissues having different properties, such as between the fat 1200 and a blood vessel (other than the great saphenous vein 1000), between the fat 1200 and a bone, between the fascia 1500 and a bone, or the like. Further, the insertion between tissues having different properties (insertion into the boundary between tissues having different properties, insertion into tissue between tissues having different properties, or the like) is not restrictive; for example, the dissecting device 200 may be inserted into the fat 1200, thereby dissecting the fat 1200.

While fat is cut by the cutting device 300 in this embodiment, the tissue to be cut by the cutting device 300 is not limited to fat. For instance, tissue between a skin-fat boundary and a fat-muscle boundary, tissue between a skin-fat boundary and a fat-interosseous membrane boundary, connective tissue, tissue between a skin layer and a muscle layer, tissue between a skin layer and an interosseous membrane, branch vessels, and the like may also be cut by the cutting device 300.

While the dissecting device 200 is disposed spaced from the great saphenous vein 1000 so as not to contact the great saphenous vein 1000 in this embodiment, the dissecting device 200 may be disposed in contact with the great saphenous vein 1000. In other words, the dissecting device 200 may be inserted between the great saphenous vein 1000 and the fat 1200.

Second Embodiment

Figure 6:
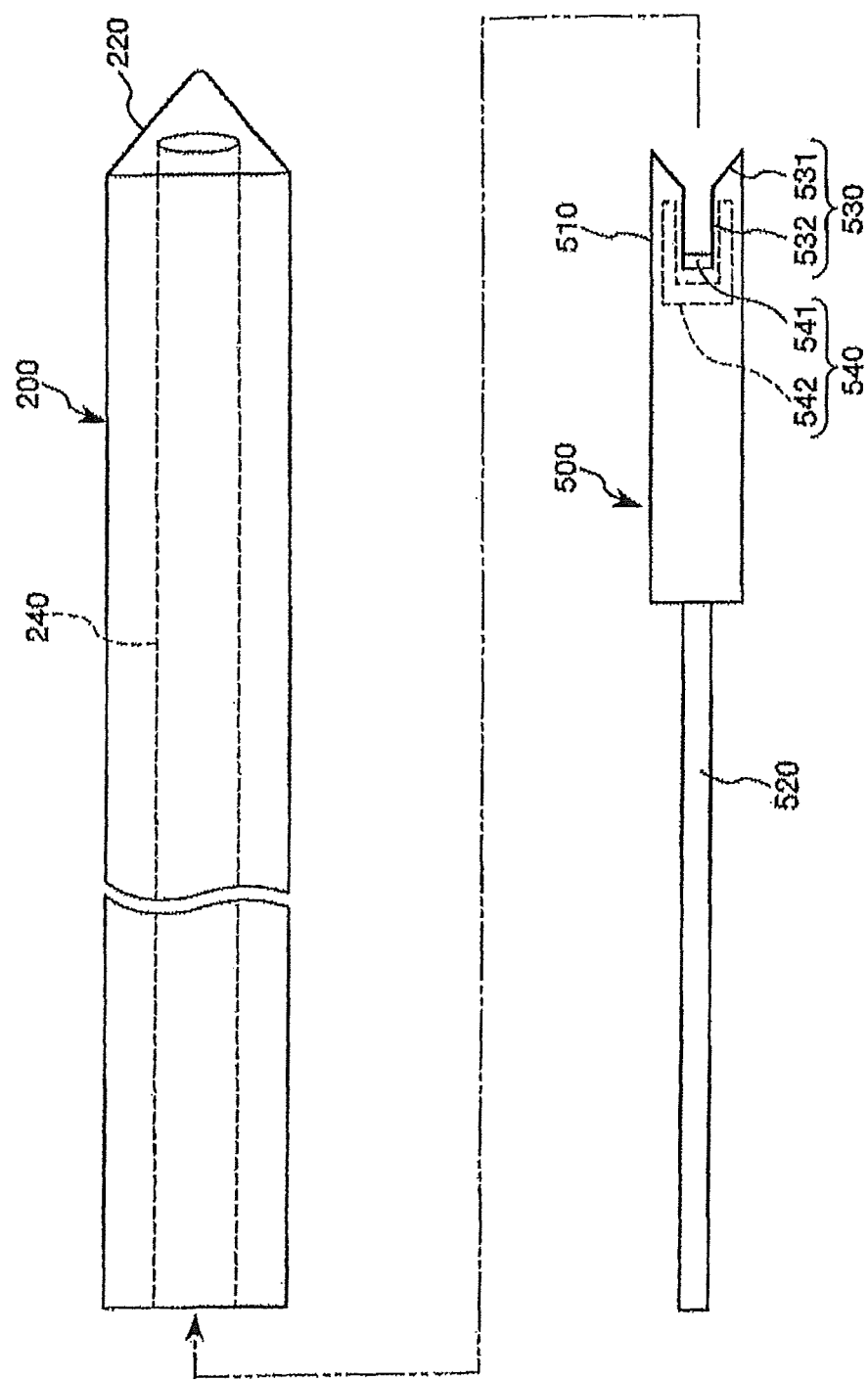
FIG. 6 illustrates a dissecting device and a blood vessel treating device forming a part of a blood vessel dissecting device according to a second embodiment of the present disclosure.
Figure 7A:
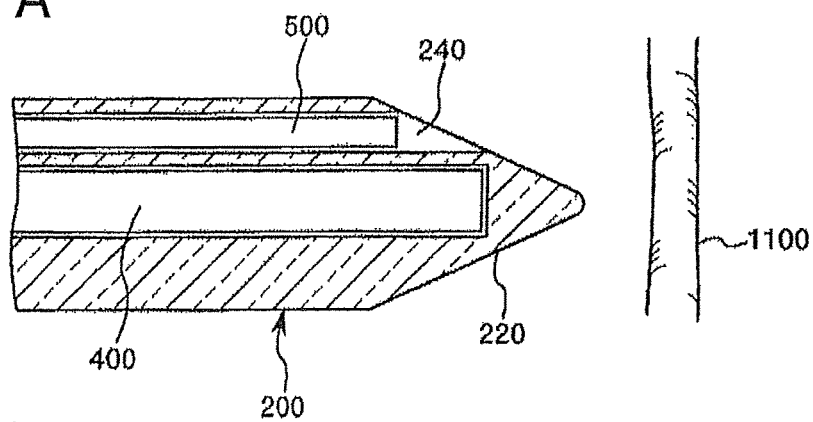
FIGS. 7A to 7C are views explaining a blood vessel dissecting method carried out using the blood vessel dissecting device shown in FIG. 6.
Figure 7B:
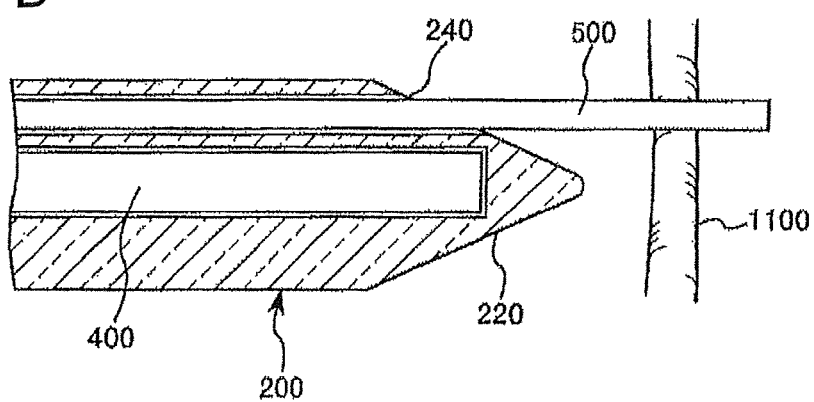
Figure 7C:
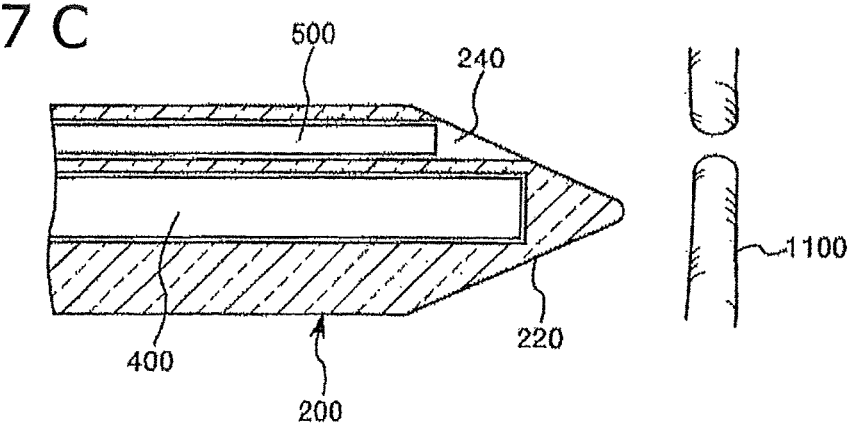

FIGS. 6-7C illustrate a second embodiment of a blood vessel dissecting device and a blood vessel dissecting method representing another example of the disclosure here.

Referring to these figures, the second embodiment will be described below. The following description will primarily describe differences associated with this embodiment relative to the aforementioned embodiment, and a detailed description of features which are the similar to features in the first embodiment will not be repeated.

This embodiment is the same as the first embodiment described above, except mainly that the blood vessel dissecting device in this embodiment further includes a blood vessel treating device used together with the dissecting device.

Blood Vessel Dissecting Device

A blood vessel dissecting device 100 in this embodiment includes a dissecting device 200, a cutting device 300, and a blood vessel treating device 500. Since the cutting device 300 is configured in the same manner as in the cutting device 300 in the first embodiment, the following detailed description will primarily focus on the dissecting device 200 and the blood vessel treating device 500.

Dissecting Device

The dissecting device 200 possesses the same configuration as described above in the first embodiment. In addition, the dissecting device 200 in this embodiment has a passing hole 240 in which the blood vessel treating device 500 is inserted and passed, as shown in FIG. 6. The passing hole 240 opens at the proximal end and a dissecting section 220 of the dissecting device 200. The passing hole 220 is thus a through hole open at both ends. The blood vessel treating device 500 can be inserted into the dissecting device 200 via the proximal-side opening, and can protrude from (distally beyond) the distal end of the dissecting device 200 via the distal-side opening.

Blood Vessel Treating Device

As shown in FIG. 6, the blood vessel treating device 500 includes a plate-shaped main body section 510, and a bar-shaped operating section 520 connected to the proximal end of the main body section 510. The main body section 510 has a groove portion 530 opening at a distal portion of the main body section 510. The groove portion 530 includes a tapered blood vessel guide groove section 531 having a width gradually decreasing toward the distal side, and a straight blood vessel treating groove section 532 which is located on the proximal side of the blood vessel guide groove section 531 and is substantially constant in width. The blood vessel guide groove section 531 is a groove section for guiding a branch vessel 1100 into the blood vessel treating groove section 532. On the other hand, the blood vessel treating groove section 532 is a groove section for cutting and stanching the branch vessel 1100 guided by the blood vessel guide groove section 531. The blood vessel treating groove section 532 is provided with a treating section 540 adapted to cut and stanch a branch vessel. The treating section 540 has a bipolar structure including a pair of electrodes 541 and 542 configured to generate an electric field inside the blood vessel treating groove section 532. The configuration of the treating section 540 is the same as that of the treating section 330 described above in the first section, and, therefore, a detailed description of the treating section 330 is not repeated here.

Blood Vessel Dissecting Method

In a first step, the dissecting device 200 is inserted into a living body. When a branch vessel 1100 appears on the forward side of the dissecting device 200, as depicted in FIG. 7A, the blood vessel treating device 500 is protruded from (extended distally beyond) the distal-side opening of the passing hole 240, as shown in FIG. 7B, and the branch vessel 1100 is cut and stanched by the treating section 540. Then, the blood vessel treating device 500 is retracted into the passing hole 240, as shown in FIG. 7C, and the dissecting device 200 is moved forward again. When such a procedure is followed, cutting of the branch vessel 1100 by the dissecting device 200 can be effectively prevented.

The blood vessel treating device 500 is not specifically restricted so long as it can treat the branch vessel 1100. For instance, the blood vessel treating device 500 may be one with a monopolar structure, such as an electrosurgical knife, or a pair of scissors may be used. In the case where a pair of scissors is used, a ligation device may be used jointly.

By the second embodiment described above, also, the same or equivalent effects to those of the aforementioned first embodiment can be produced.

Third Embodiment

Figure 8:
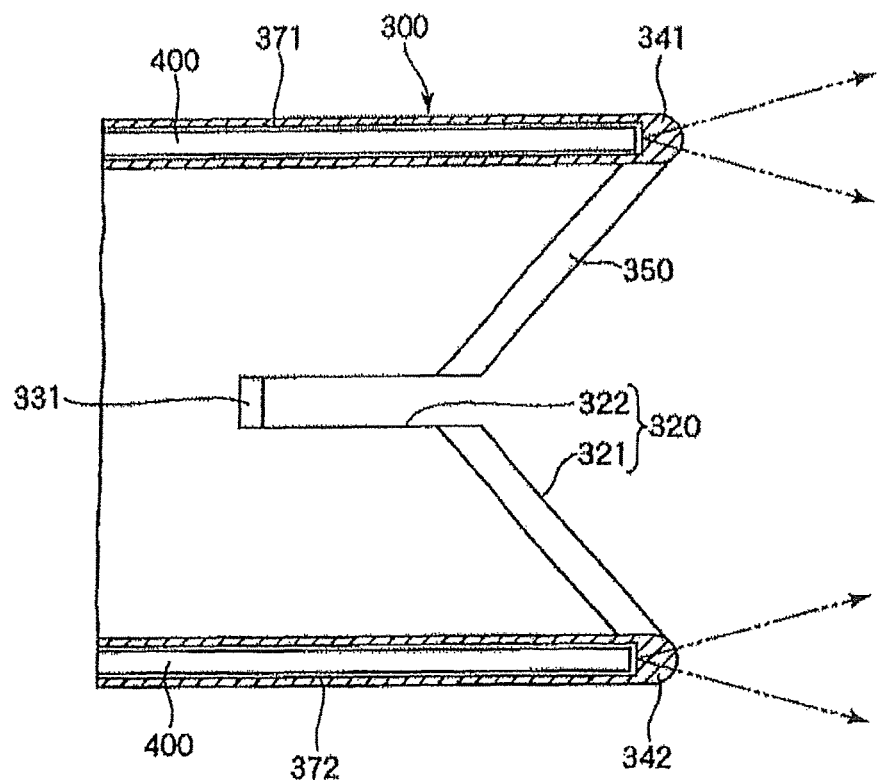
FIG. 8 is a partial cross-sectional view showing a cutting device forming a part of a blood vessel dissecting device according to a third embodiment of the present disclosure.

FIG. 8 illustrates a cutting device forming a part of a blood vessel dissecting device according to a third embodiment of the present disclosure.

Referring to this figure, the third embodiment will be described below. The description below will primarily focus on differences between this third embodiment and the embodiments described above. A detailed description of features and aspects of this third embodiment that are the same as those described above will not be repeated. This embodiment is the same as the first embodiment described above, except mainly that an imaging device can be inserted or provided in a cutting device.

Cutting Device

As shown in FIG. 8, a cutting device 300 in this embodiment has insertion holes 371 and 372 which are formed inside protection sections 341 and 342 and are open at proximal ends. Into the insertion holes 371 and 372 can be inserted imaging devices 400. In addition, at least distal portions of the protection sections 341 and 342 are substantially colorless and transparent and are light-transmitting. With the imaging devices 400 inserted in the insertion holes 371 and 372, therefore, the forward side of the cutting device 300 (particularly, a boundary area between fat 1200 and skin 1400, and a boundary area between fat 1200 and fascia 1500) can be observed by the imaging devices 400 through the protection sections 341 and 342. Consequently, the cutting device 300 can be inserted into a living body smoothly and accurately.

While the distal portions of the protection sections 341 and 342 are substantially colorless and transparent in this embodiment, these portions are not limited to being colorless and transparent insofar as they are light-transmitting; thus, the distal portions may be colored in red, blue, green or the like. While the protection sections 341 and 342 of the cutting device 300 in this embodiment are formed therein with the insertion holes such that two imaging devices 400 can be simultaneously inserted therein, the number of the insertion holes is not limited to two. For example, only one insertion hole may be provided. The layout of the insertion holes is also not particularly limited. In addition, a configuration may be adopted wherein the insertion holes are omitted and, for example, an imaging device 400 can be fixed on the outside of the cutting device 300.

By the third embodiment described above, also, the same or equivalent effects to those of the aforementioned first embodiment can be produced.

Fourth Embodiment

Figure 9A:
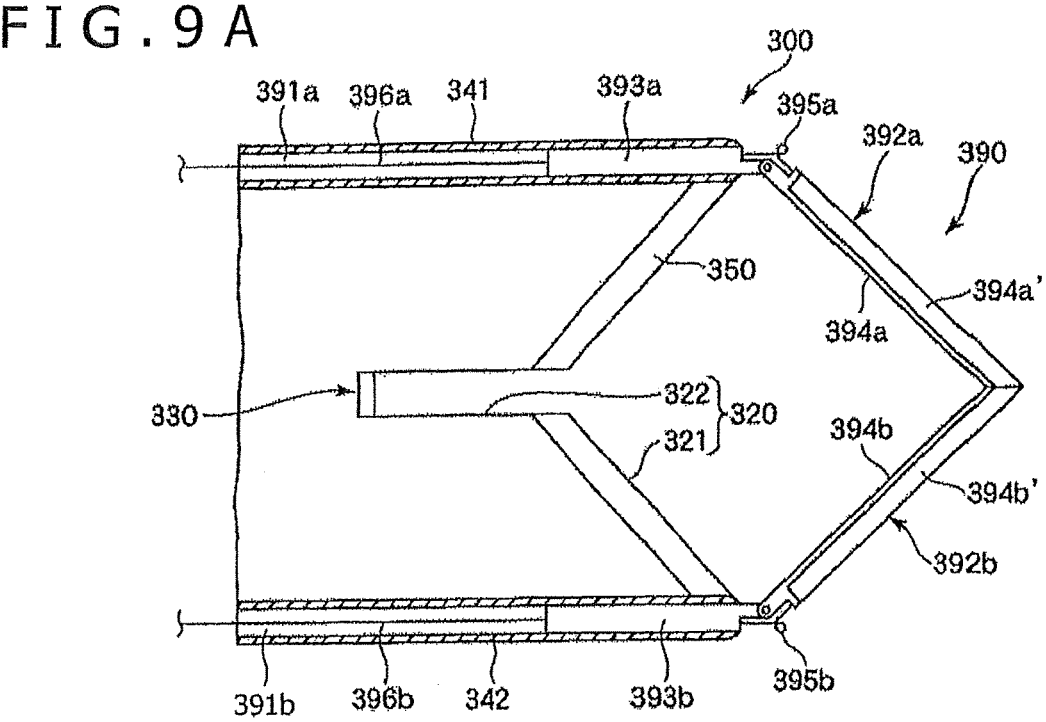
FIGS. 9A and 9B are partial cross-sectional views showing a cutting device forming a part of a blood vessel dissecting device according to a fourth embodiment of the present disclosure.
Figure 9B:
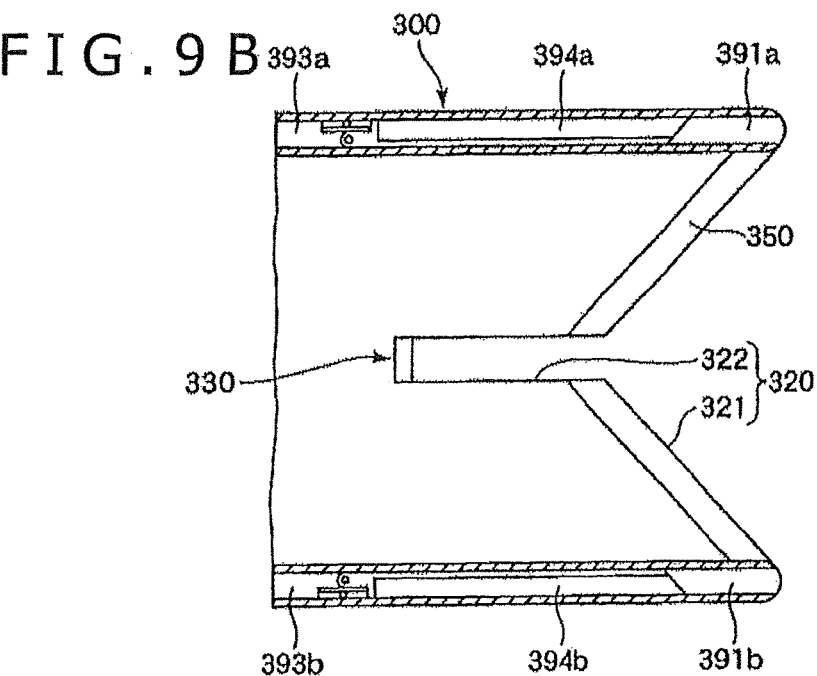

FIGS. 9A and 9B illustrate a cutting device forming a part of a blood vessel dissecting device according to a fourth embodiment of the present disclosure.

Referring to these figures, the fourth embodiment will be described below. The following description will primarily focus on differences between this fourth embodiment and embodiments described above. A detailed description of features and aspects of this fourth embodiment that are the same as those described above will not be repeated.

This embodiment is the same as the first embodiment described above, except mainly for differences in the configuration of cutting device.

Cutting Device

As shown in FIGS. 9A and 9B, a cutting device 300 in this embodiment has an insertion guide section 390 for facilitating the insertion of the cutting device 300 into a living body.

The insertion guide section 390 has accommodation holes 391*a* and 391*b* which are formed along and inside protection sections 341 and 342 and have distal ends opening in the protection sections 341 and 342. Furthermore, the insertion guide section 390 includes a first guide mechanism 392*a* disposed in the accommodation hole 391*a*, and a second guide mechanism 392*b* disposed in the accommodation hole 391*b*. The first guide mechanism 392*a* includes a proximal portion 393*a* disposed slidably in the accommodation hole 391*a*, a distal portion 394*a* located on the distal side of the proximal portion 393a and connected to and turnable relative to the proximal portion 393a, a spring member (biasing section) 395a for biasing the distal portion 394a toward the center axis side with reference to the proximal portion 393a, and a cord (operating section) 396a connected to the proximal portion 393a. Similarly, the second guide mechanism 392b includes a proximal portion 393b disposed slidably in the accommodation hole 391b, a distal portion 394b located on the distal side of the proximal portion 393b and connected to and turnable relative to the proximal portion 393b, a spring member 395b for biasing the distal portion 394b toward the center axis side with reference to the proximal portion 393b, and a cord 396b connected to the proximal portion 393b.

In the insertion guide section 390 as above, when the distal portions 394a and 394b protrude from (extend distally outside of) the accommodation holes 391a and 391b, the distal portions 394a and 394b are tilted toward the center axis side by the biasing forces of the spring members 395a and 395b so that their distal ends come in contact with each other. As a result, the groove section 320 is closed, and a distal portion of the cutting device 300 is deformed into a tapered shape. Accordingly, it becomes easier for the cutting device 300 to be inserted into a living body via an incision 1300. In addition, the distal portions 394a and 394b have cutting edge sections 394a' and 394b' directed toward the forward side when the distal portions 394a and 394b are tilted to the center axis side. This helps ensure easier insertion of the cutting device 300 into the living body through the incision 1300. On the other hand, when the cords 396a and 396b are pulled proximally, the distal portions 394a and 394b are retracted into the accommodation holes 391a and 391b so that the groove section 320 and a treating section 330 appear, as depicted in FIG. 9B.

When the cutting device 300 having the insertion guide section 390 as above is inserted, in the state shown in FIG. 9A, into a living body, the inserting operation can be carried out more smoothly. Thereafter, the cutting device 300 is moved forward within the living body in the state shown in FIG. 9B, whereby cutting of fat 1200 and a treatment (cutting and stanching) of a branch vessel 1100 can be performed in the same manner as in the aforementioned first embodiment.

By the fourth embodiment described above, also, the same or equivalent effects to those of the aforementioned first embodiment can be produced.

Fifth Embodiment

Figure 10A:
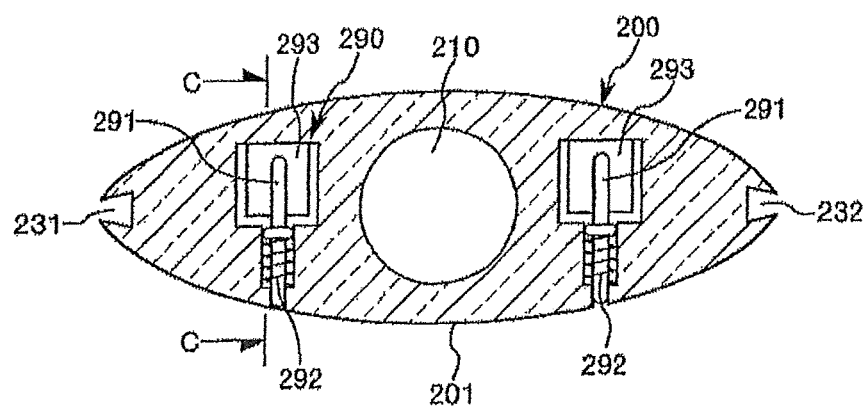
FIGS. 10A to 10C are cross-sectional views showing a dissecting device forming a part of a blood vessel dissecting device according to a fifth embodiment of the present disclosure.
Figure 10B:
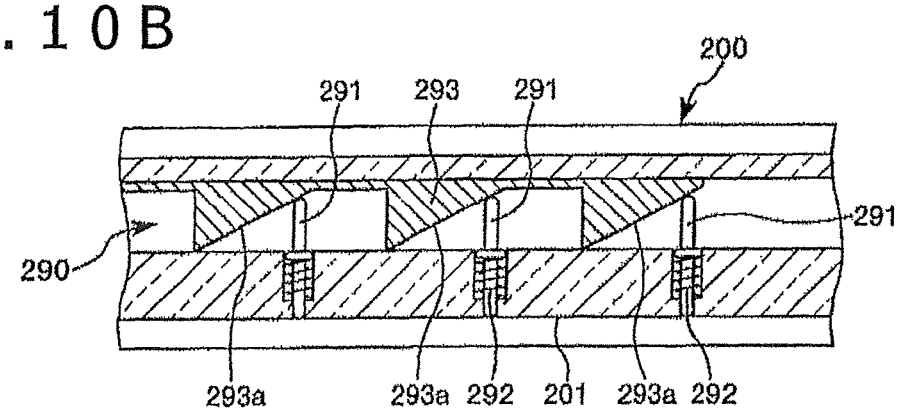
Figure 10C:
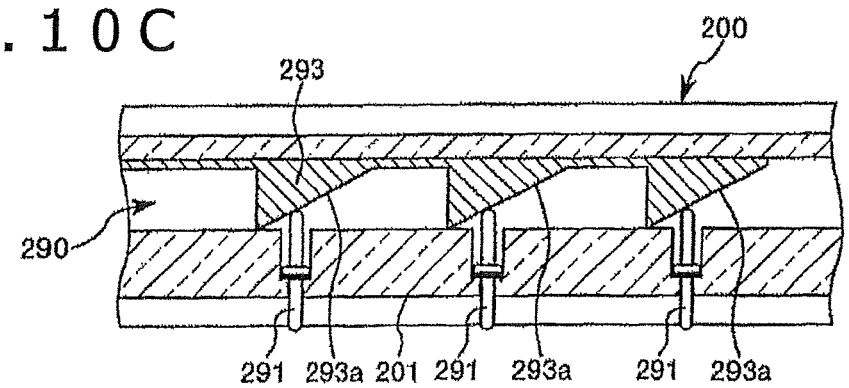
Figure 11:
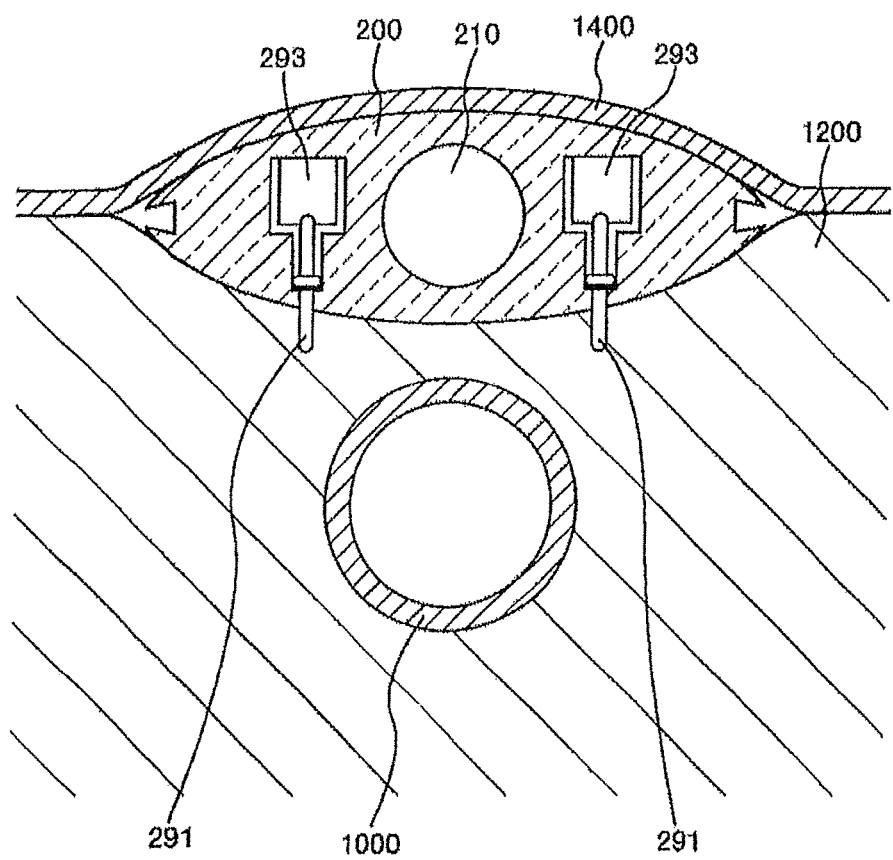
FIG. 11 is a cross-sectional view for explaining an effect of the dissecting device shown in FIGS. 10A to 10C.

FIGS. 10A to 11 illustrate a dissecting device forming a part of a blood vessel dissecting device according to a fifth embodiment of the present disclosure.

Referring to these figures, the fifth embodiment will be described below. In the following, the description will focus primarily on differences between this fifth embodiment and the embodiments described above. A detailed description of features and aspects of this fifth embodiment that are the same as those described above will not be repeated.

This embodiment is the same as the first embodiment described above, except mainly for differences in the configuration of the dissecting device.
Dissecting Device As shown in FIGS. 10A to 10C, a dissecting device 200 in this embodiment has an anchoring mechanism 290 for reducing a slippage (displacement) of the dissecting device 200 in a living body. The anchoring mechanism 290 includes: a projection (anchoring section) 291 disposed and configured to project from and retract into the dissecting device 200; a spring member (biasing section) 292 for biasing the projection 291 toward the inside of the dissecting device 200; and an operating section 293 for operating (depressing) the projection 291. The projections 291 are arranged on both sides with respect to the width direction of the dissecting device 200, and are arranged plural in number in spaced-apart relation in along the axial direction of the dissecting device 200. Each of the projections 291 is biased toward the inside by the spring member 292, and, in the retracted state depicted in FIG. 10B, the projection 291 is retracted in the dissecting device 200. The operating section 293 is disposed inside the dissecting device 200 so as to be slidably moved in the axial direction. The operating section 293 has a contact surface 293a which is inclined against the axial direction and makes contact with the projection 291. When the operating section 293 is slid toward the distal side, the projection 291 is depressed downward by the contact surface 293a, as shown in FIG. 10C, resulting in that the projection 291 protrudes from the surface (lower surface) of the dissecting device 200 to the exterior. When the operating section 293 is slid toward the proximal side starting from this condition, the biasing force of the spring member 292 causes the projection 291 to be again retracted into the dissecting device 200.

The dissecting device 200 having the anchoring mechanism 290 as above helps ensure that when the dissecting device 200 with the projections 291 in the retracted state is inserted into a living body and thereafter the projections 291 protrude to the side of a great saphenous vein 1000, the projections 291 bite into fat 1200, as shown in FIG. 11. As a result, slippage of the dissecting device 200 in relation to the great saphenous vein 1000 can be reduced, so that the dissecting device 200 can be maintained in an appropriate position during the intended technique. Accordingly, it is possible, for example, to guide the cutting device 300 more accurately.

The projections 291 are configured to protrude or project in the thickness direction of the dissecting device 200 from a surface 201 on one side with respect to the thickness direction, but the place and the direction of protrusion of each of the projections 291 are not restricted in this way. In addition, while the projection 291 is used as the anchoring section in this embodiment, the anchoring section is not limited to this; for example, a plate-shaped member may be used in place of the projection. While the projection 291 is protruded and retracted by use of the operating section 293 and the spring member 292 in this embodiment, the configuration for protrusion and retraction of the projection 291 is not restricted to this; for example, a drive source such as a motor may be used to electrically effect protrusion and retraction of the projection 291.

By the fifth embodiment described above, also, the same or equivalent effects to those of the first embodiment described above can be produced.

Sixth Embodiment

Figure 12A:
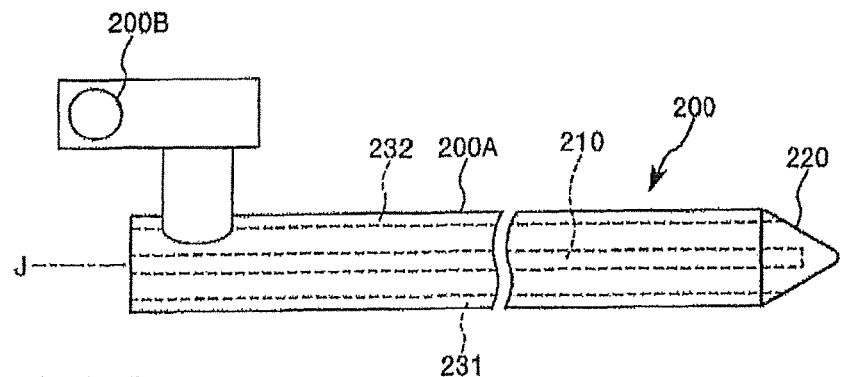
Figure 12B:
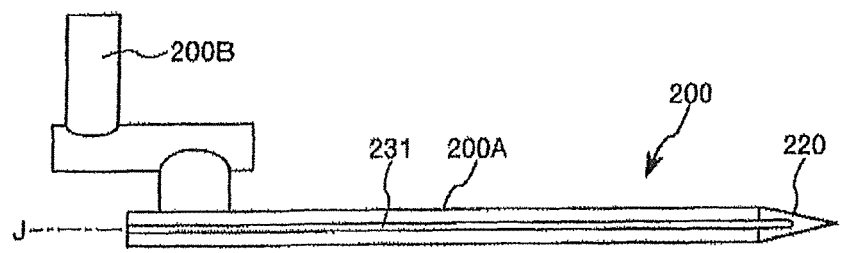
Figure 12C:
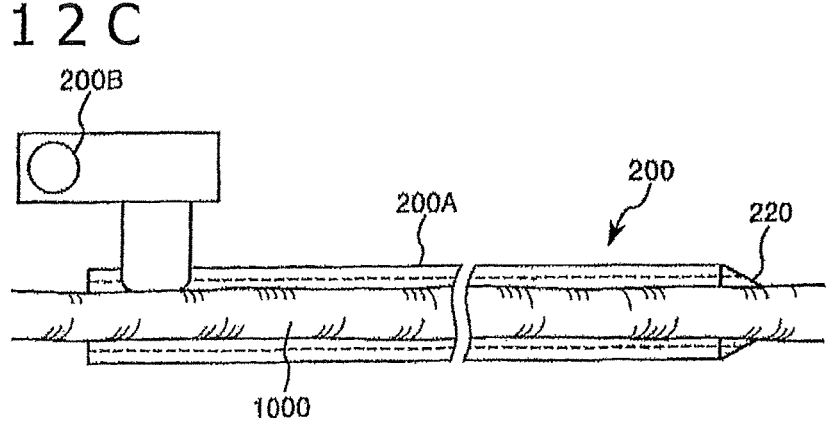

FIGS. 12A to 12C illustrate a dissecting device possessed by a blood vessel dissecting device according to a sixth embodiment of the present disclosure.

Referring to these figures, the sixth embodiment will be described below. In the following, the detailed description will primarily focus on differences between this embodiment and the embodiments described above. A detailed description of features and aspects of this sixth embodiment that are the same as those described above will not be repeated.

This embodiment is the same as the first embodiment described above, except mainly for differences in the configuration of dissecting device.

Dissecting Device

As shown in FIGS. 12A and 12B, a dissecting device 200 in this embodiment includes: an insertion section 200A inserted into a living body; and an operating section (grip section) 200B located on the proximal side of the insertion section 200A and used for operating the insertion section 200A. The operating section 200B is shifted (deviated) in relation to the center axis J of the insertion section 200A, both in the thickness direction and in the width direction. In other words, the operating section 200B is offset from the center axis J of the insertion section 200A, both in the thickness direction and in the width direction.

The dissecting device 200 configured as above helps ensure easier disposition of the dissecting device 200 on the lower side (bone side) of a great saphenous vein 1000. To be more specific, since the operating section 200B is offset from the center axis J of the insertion section 200A, at the time of inserting the dissecting device 200 to the lower side of the great saphenous vein 1000, the operating section 200B does not overlap with (does not make contact with) the great saphenous vein 1000, as shown in FIG. 12C. Therefore, the dissecting device 200 can be more easily disposed along the great saphenous vein 1000.

By the sixth embodiment described above, also, the same or equivalent effects to those of the first embodiment described above can be produced.

Seventh Embodiment

Figure 13A:
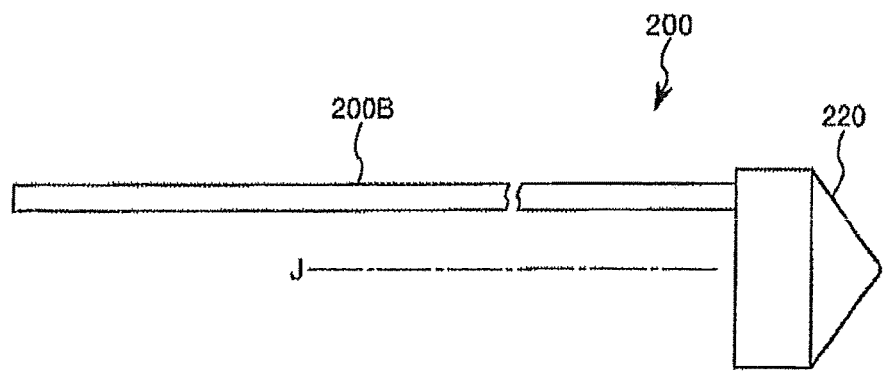
Figure 13B:
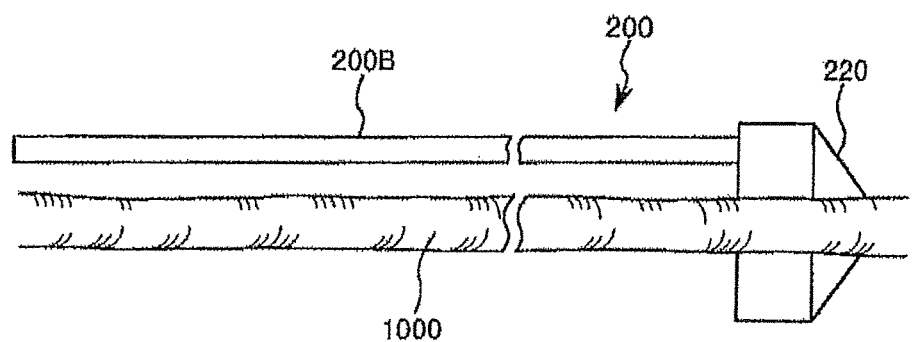

FIGS. 13A and 13B illustrate a dissecting device possessed by a blood vessel dissecting device according to a seventh embodiment of the present disclosure.

Referring to these figures, the seventh embodiment will be described below. The following detailed description will focus primarily on differences between this seventh embodiment and the embodiments described above. A detailed description of features and aspects of this seventh embodiment that are the same as those described above will not be repeated.

This embodiment is the same as the first embodiment described above, except mainly for differences in the configuration of dissecting device.

Dissecting Device

As shown in FIG. 13A, a dissecting device 200 in this embodiment includes: a dissecting section 220; and an operating section 200B located on the proximal side of the dissecting section 220 and used to operate the dissecting section 220. The operating section 200B is disposed so that the operating section 200B is shifted (deviated) in the width direction in relation to the center axis J of the dissecting section 220. The dissecting device 200 configured in this way helps ensure that at the time of disposing the dissecting device 200 on the lower side (bone side) of a great saphenous vein 1000, the great saphenous vein 1000 and the operating section 200B do not overlap with each other, as shown in FIG. 13B. Therefore, it is easier to dispose the dissecting device 200 as desired.

By the seventh embodiment described above, also, the same or equivalent effects to those of the first embodiment described above can be produced.

Eighth Embodiment

Figure 14:
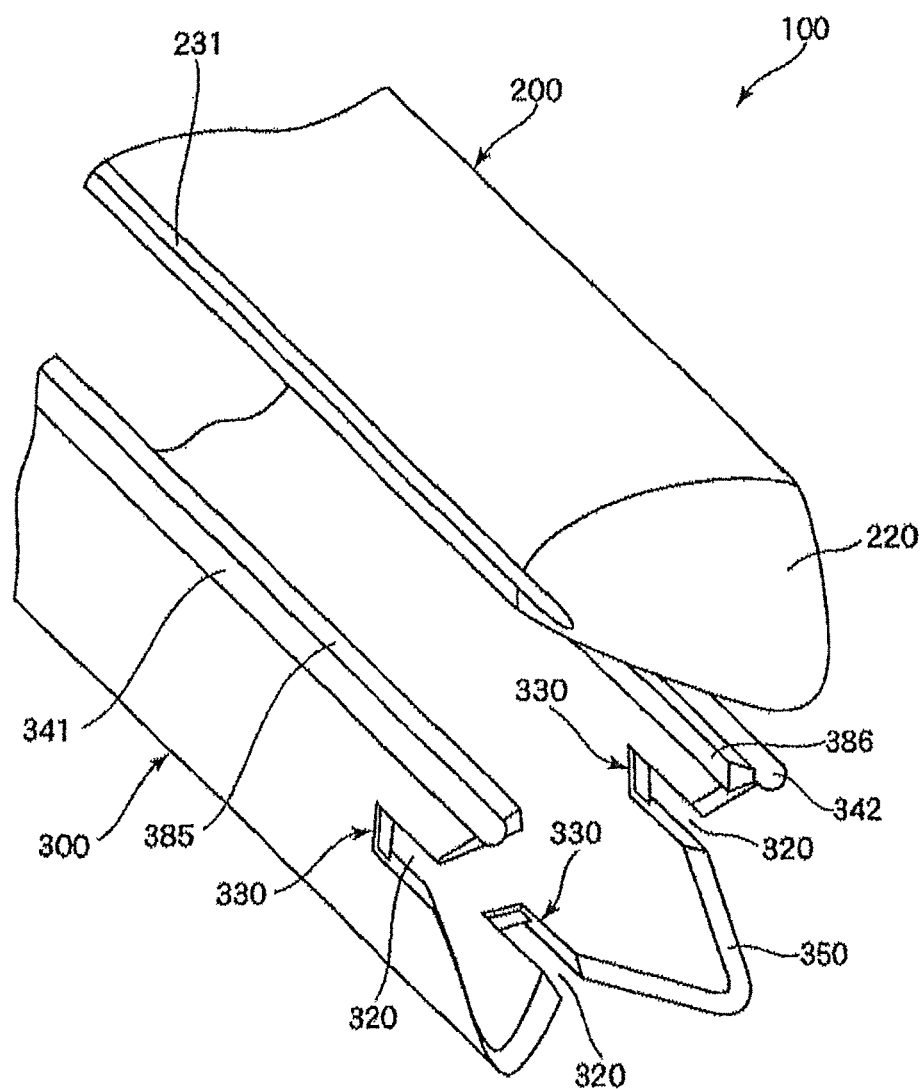
FIG. 14 is a perspective view of a blood vessel dissecting device according to an eighth embodiment of the present disclosure.

FIG. 14 is a perspective view of a blood vessel dissecting device according to an eighth embodiment of the present disclosure.

Referring to this figure, the eighth embodiment will be described below. The following detailed description will focus primarily on differences between this embodiment and the embodiments described above. A detailed description of features and aspects of this eighth embodiment that are the same as those described above will not be repeated.

This embodiment is the same as the aforementioned first embodiment, except mainly for differences in the configuration of cutting device.

Cutting Device

As shown in FIG. 14, a cutting device 300 in this embodiment has a roughly C-shaped cross-section. A protection section 341 is disposed at one end portion with respect to the circumferential direction, and a protection section 342 is disposed at the other end portion with respect to the circumferential direction. The protection section 341 is provided with a connection section 385, in the form of a stretch of projection (or a rib or ridge), for connection with a rail 231 of a dissecting device 200. The protection section 342 is provided with a connection section 386, in the form of a stretch or length of projection (or a rib or ridge), for connection with the rail 232 of the dissecting device 200. In addition, groove sections 320 and treating sections 330 are disposed in pluralities along the circumferential direction. In the illustrated embodiment, the treating section 330 is positioned circumferentially between the groove sections 320.

An example of a manner of use of the cutting device 300 configured in this fashion is as follows. First, the dissecting device 200 is inserted into a living body (on the upper side or lower side of a great saphenous vein 1000). Next, the cutting device 300 is connected to the dissecting device 200, and the cutting device 300 is inserted into the living body while the cutting device 300 is guided by the dissecting device 200. As a result, the great saphenous vein 1000 is dissected over the entire range in the circumferential direction of the vein. This embodiment helps ensure that, for example as compared with the first embodiment, the first step can be carried out in a reduced number of procedures (steps).

By the eighth embodiment described above, also, the same or equivalent effects to those of the first embodiment described above can be produced.

Ninth Embodiment

FIG. 15A illustrates a great saphenous vein, and FIG. 15B is a plan view of a dissecting device forming a part of a blood vessel dissecting device according to a ninth embodiment of the present disclosure.

Referring to these figures, the ninth embodiment will be described below. The following detailed description will focus primarily on differences between this ninth embodiment and the embodiments described above. A detailed description of features and aspects of this ninth embodiment that are the same as those described above will not be repeated.

This embodiment is the same as the first embodiment described above, except mainly for differences in the configuration of dissecting device.

As depicted in FIG. 15B, a great saphenous vein 1000 may not extend straight but may extend tortuously (in a somewhat meandering manner). In view of this, a dissecting device 200 in this embodiment is designed to be sufficiently large in width so that upon insertion into a living body, the dissecting device 200 overlaps the whole area of that portion of the great saphenous vein 1000 which is to be dissected. This helps ensure that, at the time of inserting a cutting device 300 along the dissecting device 200 after insertion of the dissecting device 200 into the living body, contact between the cutting device 300 and the great saphenous vein 1000 can be prevented from occurring. Therefore, damage to the great saphenous vein 1000 can be avoided or prevented. In addition, the dissection of the great saphenous vein 1000 in a state where the vein part to be dissected is entirely covered with fat 1200 can be achieved more reliably.

By the ninth embodiment described above, also, the same or equivalent effects to those of the first embodiment described above can be produced.

Tenth Embodiment

FIGS. 16A and 16B are plan views of a dissecting device forming a part of a blood vessel dissecting device according to a tenth embodiment of the present disclosure.

Referring to these figures, the tenth embodiment will be described below. The following detailed description will focus primarily on differences between this embodiment and the embodiments described above. A detailed description of features and aspects of this tenth embodiment that are the same as those described above will not be repeated.

This embodiment is the same as the first embodiment described above, except mainly for differences in the configuration of dissecting device.

A dissecting device 200 in this embodiment is deformable at least in the width direction of the dissecting device 220, and is configured to retain its deformed state. First, as shown in FIG. 16A, the dissecting device 200 set in a substantially straight form is inserted into a living body along a great saphenous vein 1000 to form an insertion hole, and then the dissecting device 200 is drawn out of the living body. The dissecting device 200 may overlap the whole area of that portion of the great saphenous vein 1000 which is to be dissected before the dissecting device 200 set in the substantially straight form is inserted into the living body along the great saphenous vein 1000 to form the insertion hole, and then the dissecting device 200 is drawn out of the living body. The dissecting device 200 is deformed in conformity with the shape of the great saphenous vein 1000, and thereafter the deformed dissecting device 220 is inserted again into the insertion hole. By this procedure, the dissecting device 200 can be disposed in conformity with the tortuous state of the great saphenous vein 1000, as shown in FIG. 16B. At the time of inserting the cutting device 300 into the living body along the dissecting device 200, therefore, contact between the cutting device 300 and the great saphenous vein 1000 can be prevented from occurring, so that damage to the great saphenous vein 1000 can be avoided or prevented. In addition, the great saphenous vein 1000 can be dissected in a state of being entirely covered substantially evenly with fat 1200. Cutting-away of the fat 1200 in a surplus amount can also be restrained.

The tortuous state of the great saphenous vein 1000 can be grasped on the basis of images obtained, for example, by a diagnosis carried out using MRI (magnetic resonance imaging), CT (computed tomography) scan, ultrasound, infrared rays (near infrared rays), X-rays, an endoscope, or the like.

With the dissecting device 200 secured to the living body (a leg part of the patient), the insertion of the cutting device 300 can be carried out more smoothly. The method for securing the dissecting device 200 to the living body is not particularly limited. For example, there can be adopted a method wherein a fixture capable of being fixed by winding around a leg part is mounted onto the leg part, and the dissecting device 200 is secured to the fixture.

By the tenth embodiment described above, also, the same or equivalent effects to those of the first embodiment described above can be produced.

Eleventh Embodiment

FIGS. 17A and 17B are plan views of a dissecting device possessed by a blood vessel dissecting device according to an eleventh embodiment of the present disclosure.

Referring to these figures, the eleventh embodiment will be described below. The following detailed description will focus primarily on differences between this eleventh embodiment and the embodiments described above. A detailed description of features and aspects of this embodiment that are the same as those described above will not be repeated.

This embodiment is the same as the first embodiment described above, except mainly that the blood vessel dissecting device in this embodiment further includes a guide device.

A blood vessel dissecting device 100 in this embodiment includes a guide device 600 shown in FIG. 17A, in addition to a dissecting device 200 and a cutting device 300. The guide device 600 is designed in conformity to a preliminarily grasped shape of a great saphenous vein 1000. The guide device 600 is provided with rails 601 and 602 for guiding the cutting device 300; on the other hand, rails 231 and 232 are omitted from the dissecting device 200.

In using the blood vessel dissecting device 100 configured in this way, first, the dissecting device 200 is inserted into the living body along the great saphenous vein 1000 to form an insertion hole, and is drawn out of the living body. Next, the guide device 600 is inserted again into the insertion hole. As a result, the guide device 600 can be disposed in conformity with the tortuous state of the great saphenous vein 1000 as shown in FIG. 17B. Therefore, at the time of inserting the cutting device 300 into the living body along the guide device 600, contact between the cutting device 300 and the great saphenous vein 1000 can be prevented from occurring, so that damage to the great saphenous vein 1000 can be avoided or prevented. The great saphenous vein 1000 can be dissected in a state of being entirely covered substantially evenly with fat 1200. In addition, cutting-away of the fat 1200 in a surplus amount can be restrained.

By the eleventh embodiment described above, also, the same or equivalent effects to those of the first embodiment described above can be produced.

Twelfth Embodiment

Figure 18A:
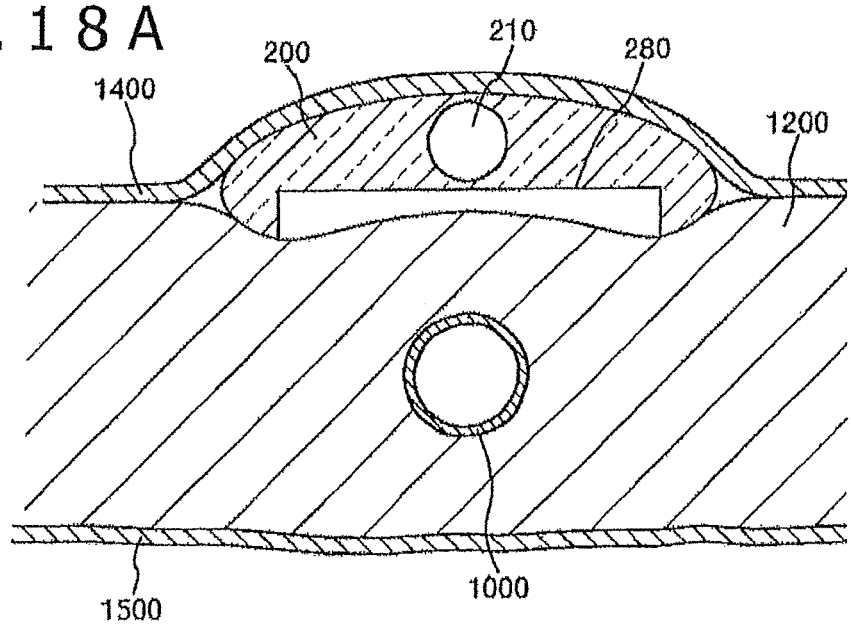
FIGS. 18A and 18B are cross-sectional views of a blood vessel dissecting device according to a twelfth embodiment of the present disclosure.
Figure 18B:
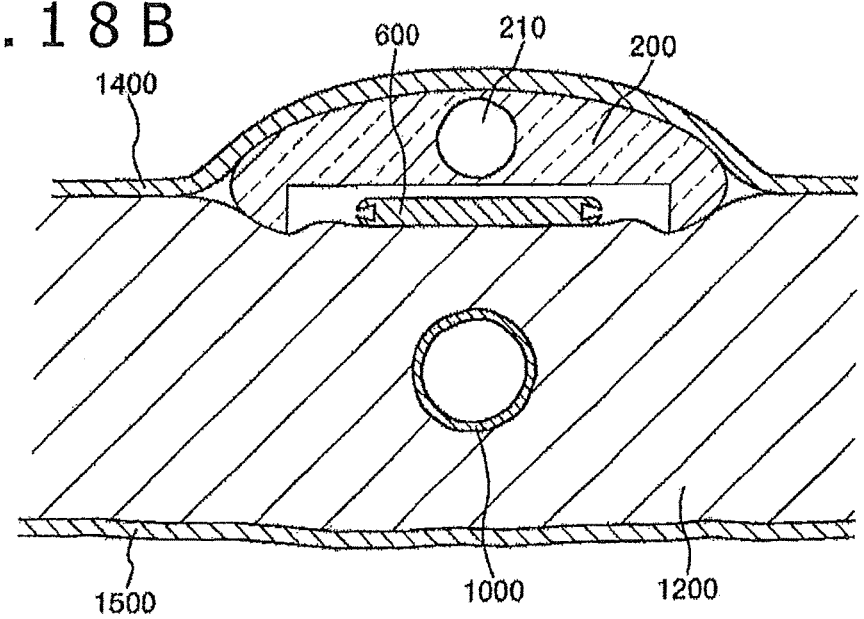

FIGS. 18A and 18B are cross-sectional views showing a blood vessel dissecting device according to a twelfth embodiment of the present disclosure.

Referring to these figures, the twelfth embodiment will be described below. The following detailed description will focus primarily on differences between this twelfth embodiment and the embodiments described above.

This embodiment is the same as the eleventh embodiment described above, except mainly for differences in the configuration of the dissecting device.

As shown in FIG. 18A, a dissecting device 200 in this embodiment is provided with an insertion hole (insertion groove or insertion recess) 280 in which a guide device 600 can be inserted. The insertion hole 280 opens to a surface on one side of the dissecting device 200 (a surface oriented to the side of a great saphenous vein 1000 when the dissecting device 200 is inserted in a living body). In using the blood vessel dissecting device 100 configured in this way, first, the dissecting device 200 is inserted into the living body along the great saphenous vein 1000, as shown in FIG. 18A. Next, as shown in FIG. 18B, the guide device 600 is inserted into the insertion hole 280. By this, the guide device 600 can be rather smoothly disposed in conformity to the tortuous state of the great saphenous vein 1000. Subsequently, the cutting device 300 is inserted into the living body along the guide device 600. This procedure helps ensure that at the time of inserting the cutting device 300, contact between the cutting device 300 and the great saphenous vein 1000 can be prevented from occurring, so that damage to the great saphenous vein 1000 can be avoided or prevented. In addition, the great saphenous vein 1000 can be dissected in a state of being entirely covered substantially evenly with fat 1200. Cutting-away of the fat 1200 in a surplus amount can also be restrained.

By the twelfth embodiment described above, also, the same or equivalent effects to those of the first embodiment described above can be produced.

While the blood vessel dissecting device and the blood vessel dissecting method according to the described aspects of the present disclosure have been described above on the basis of the embodiments illustrated in the drawings, the disclosure is not limited to the embodiments. The configuration of each component can be replaced by any configuration that has a function similar or substantially equivalent to the original. And other structure may be added to the configuration according to the present disclosure. In addition, the embodiments and application examples may be combined in a desired manner.

Figure 19:
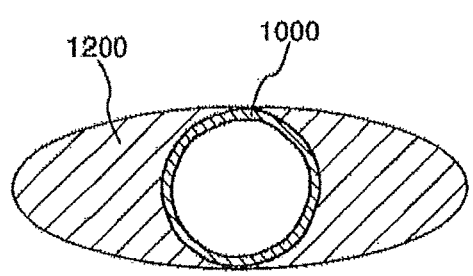
FIG. 19 is a cross-sectional view showing a dissected blood vessel.

The great saphenous vein is dissected in the state of being covered with fat over the entire perimeter of the vein in the aforementioned embodiments, but the great saphenous vein may not necessarily be covered with fat over its entire perimeter. Thus, the great saphenous vein may be dissected in a state where the periphery of the vein is partly covered with fat, or in a state of being not covered with fat. For instance, the great saphenous vein 1000 may be dissected in a state of being covered with flat-shaped fat 1200, as shown in FIG. 19, wherein the fat 1200 present on the upper and lower sides is relatively thin (or the fat 1200 is absent on the upper and lower sides) and wherein the fat 1200 present on the left and right sides is relatively thick. In such a state, the conditions (for example, the presence or absence of damages, shape, twisting, etc.) of the great saphenous vein 1000 can be easily checked and confirmed from above and from below. Consequently, it is possible to use the great saphenous vein 1000 as a bypass vessel or the like after grasping the conditions of the great saphenous vein 1000.

Other Embodiments

Set forth next is a description of various other embodiments of dissecting devices and techniques according to the disclosure here. For purposes of facilitating an understanding of general aspects of the anatomy involved here, FIG. 20A shows a leg of a living body (patient) and depicts the great saphenous vein 1000 extending from the upper leg to the lower leg, FIGS. 20B and 20C depict cross-sections of the upper leg and the lower leg respectively, including the great saphenous vein, and FIG. 21A and schematically depict the noted portions of the upper and lower leg respectively.

As shown in FIGS. 21A and 21B, the great saphenous vein 1000 (hereinafter referred to as the saphenous fascia) extends between the upper and lower leg of a living body (patient), and tissue or a membrane 1600 is bound to this vein 100. This bound tissue or membrane is referred to as saphenous fascia 1600. Physical properties or characteristics of the saphenous fascia 1600 are different from a physical properties or characteristics of the muscular fascia 1500 and the fat tissue 1200 (fat), meaning it is relatively easy to dissect the saphenous fascia 1600 from the fat 1200 and the muscular fascia 1500. The embodiments of the techniques and devices described below and illustrated in the drawing figures represent examples of the techniques and devices disclosed here, and can be used to dissect tissue from other tissue, such as dissecting the saphenous fascia 1600 from the fat 1200. The description below describes a variety of operations and techniques for dissecting a vein/tissue from other adjacent tissue. The description refers specifically to dissecting the saphenous vein 100/saphenous fascia 1600 from adjacent tissue, namely fat and the muscular fascia. But it is to be understood that the dissection (and cutting) operations and methods described below are not limited to dissecting (cutting) only such vein/tissue.

Figure 22A:
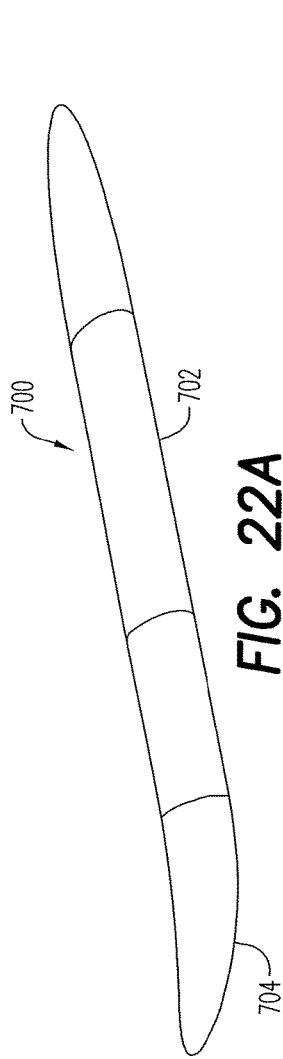
FIGS. 22A-22C illustrate an embodiment of an elongated dissecting device.
Figure 22B:
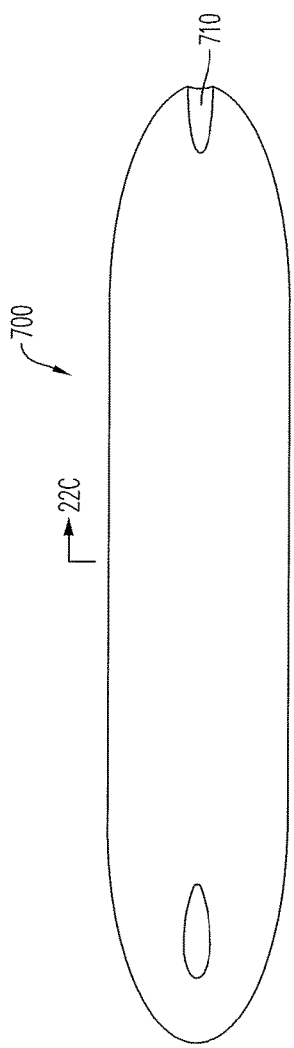

One embodiment of the blood vessel dissecting device includes the combination of a dissecting device and a cutting device. The dissecting device 700 is illustrated in FIGS. 22A and 22B, and can be used in combination with the cutting device 300 illustrated in FIGS. 3A and 3B. The dissecting device 700 shown in FIGS. 22A and 22B is an elongated bar-shaped member comprised of a main body section 702 and a dissecting section 704 for dissecting tissue. As illustrated in FIG. 22A, the dissecting section 704 is at the distal end of the dissecting device 700 and is slightly curved or upturned relative to the main body section 702. The main body section 702 lies in a common plane, whereas the slightly curved dissecting section 704 is located out of that common plane (i.e., the dissecting section 704 curves out of the plane in which the main body section 702 lies). The cross-sectional shape of the dissecting device 700 can be similar to that described above with respect to the dissecting device 200 shown in FIG. 2B, meaning the dissecting device possesses a flat shape (vertically flattened shape as seen in transverse cross-section) in cross-section, though the dissecting device is not limited to the specific flattened shape shown as other shapes (e.g., a crushed-circle-like shape (flattened circular shape), such as an oblong and an ellipse, a rectangle rounded at corners, etc.). The dissecting device 700 possesses a width that is preferably greater than the outside diameter of the blood vessel or vein to be harvested (e.g., the saphenous vein). In this regard, the dissecting device 700 can possess a dimensional relationship relative to the blood vessel similar to that described above with respect to the dissecting device 200.

Figure 22C:
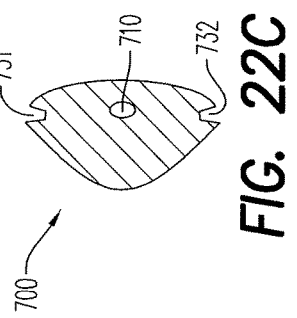

As illustrated in FIG. 22C, the opposite sides or edges of the dissecting device include rails 731, 732 in the form of recesses, grooves or the like. These rails 731, 732 are similar to the rails 231, 232 associated with the above-described embodiment of the dissecting device 200, and are configured as connection mechanisms for connecting cutting devices to the dissecting device 700.

The dissecting device 200 also includes an insertion hole 710 which is open at both ends. The insertion hole 710 is thus a through hole. The insertion hole 710 is configured to receive an imaging device such as the imaging device 400 described above to permit visual imaging inside the living body during use of the dissecting device.

The dissecting section 704 at the distal end of the dissecting device 200 is tapered in a narrowing manner toward the distal end of the dissecting device 700 as seen in FIG. 22B. The dissecting section 704 preferably possesses an appropriate degree of sharpness or bluntness so that the dissecting section 704 is able to dissect tissues having different properties (e.g., fat and skin, fat and fascia, fat and blood vessel, fat and bone, etc.) from each other without cutting branch vessels or side branches from the saphenous vein.

The dissecting device 700 is a flat dissecting device except for the slightly curved or upturned dissecting section 704 at the distal end of the dissecting device 700. The upturned distal end of the dissecting device 700 can reduce damage to the saphenous vein because the upturned distal end of the dissecting device does not strike or dig into the saphenous vein.

Figure 23A:
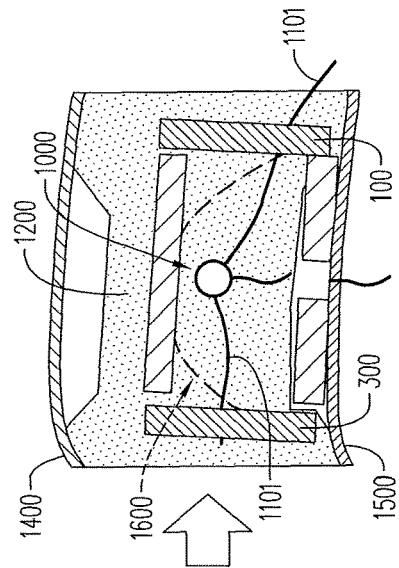
Figure 23B:
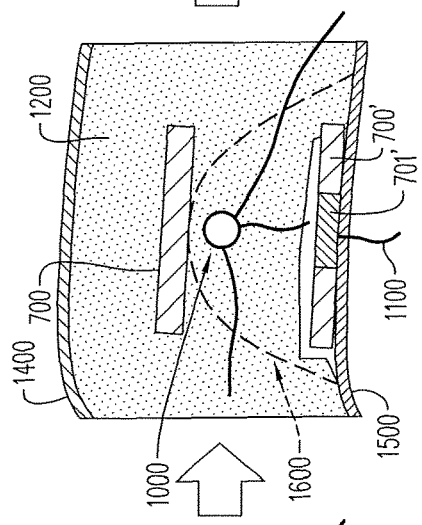
Figure 23C:
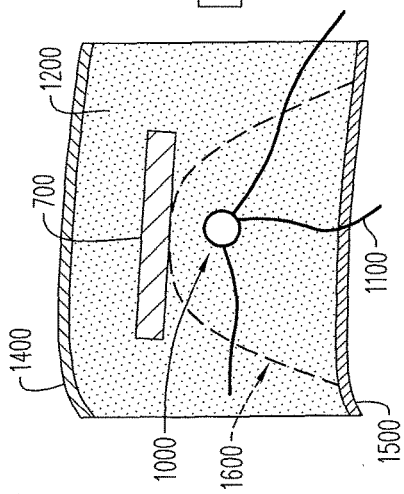

FIGS. 23A-23C illustrates an example of a dissecting technique or method utilizing the dissecting device 700 shown in FIGS. 22A and 22B, together with the cutting device 300 shown above in FIGS. 3A and 3B. First, an incision is made in the leg of the patient (living body) to provide an access site to the vein/saphenous fascia on the vein. Next, the distal end of the dissecting device 700 is inserted into the living body by way of the incision or access site in the leg of the patient. The dissecting device 700 is moved in the living body so that, as illustrated in FIG. 23A, the dissecting device 700 is positioned between the saphenous vein 1000 and the skin 1400. More specifically, the dissecting device 700 is inserted so that the under-surface of the dissecting device 700 (i.e., the surface of the dissecting device 700 facing the saphenous vein 1000) is in contact with the thin layer (the connective tissue) or saphenous fascia 1600 bound to the saphenous vein 1000. The vein 1000 may be visible through the connective tissue from outside of the living body before inserting the distal end of the flat elongated dissecting device. The dissecting device 700 is generally located at the interface between the saphenous fascia 1600 and the fat 1200. The dissecting device 700 is moved within the living body while maintaining this contact between the under-surface of the dissecting device 700 and the fascia layer (the saphenous fascia 1600). In this way, the fascia layer or saphenous fascia is dissected or separated from the adjacent tissue (e.g., fat) in the thickness direction of the dissecting device 700. That is, the fascia layer is separated from the other tissue in the vertical or up-and-down direction in FIGS. 23A-23C.

The dissecting technique or method continues, as illustrated in FIG. 23B, by inserting a second dissecting device 700' between the muscular fascia 1500 and the great saphenous vein 1000. This second dissecting device 700' is similar to the first dissecting device 700, except that the second dissecting device 700' includes a cutting device 701' positioned in the central part of the dissecting device 700' and movable along the length of the dissecting device 700'. FIG. 23B1 illustrates an example of the second dissecting device 700', but with the cutting device 701' omitted. The second dissecting device 700' includes two side-by-side elongated sections 7001, 7002 spaced apart from one another with inwardly facing grooved sides 7003, 7004 that face one another and are configured to receive the cutting device 701'. The second dissecting device 700' is inserted into the living body, for example by way of the same incision used to insert the first dissecting device 700, and is moved along the saphenous vein 1000 along a movement path that crosses a side branch 1100 of the great saphenous vein 1000 as illustrated in FIG. 23B. The side branch 1100 of the vein can be a perforator or a collateral vein. The second dissecting device 700' may be inserted into the living body before the first dissecting device 700 is inserted into the living body.

A cutting device 701' is then inserted into a connecting portion of the second connecting device 700'. The connecting portion can be similar to the rail 731, 732 shown in FIG. 22C, except that the connecting portion is provided on inwardly facing sides or edges of spaced apart portion of the second dissecting device 700'. The cutting device 701' is then moved in the forward direction, relative to the second dissecting device 700', towards the distal end of the second dissecting device 700'. During this movement of the cutting device 701', the cutting device 701' cuts the side branch of the vein (e.g., a perforator or a collateral vein).

The dissecting method continues by inserting a pair of further cutting devices into the living body. This is shown in FIG. 23C where a pair of second cutting devices 300, similar to the cutting devices 300 shown in FIGS. 3A and 3B above, are inserted on opposite sides of the saphenous vein 1000. The second connecting devices 300 are connected to connecting portions on the outer side edges of the first dissecting device 700 and the second dissecting device 700'. Thus, the second dissecting device 700' includes rails on both the inner and the outer side of the second connecting device. The second cutting devices 300 are moved along (relative to) the two dissecting devices 700, 700' towards the distal ends of the dissecting devices 700, 700'. During this movement, the second cutting devices 300 cut or sever the side branches 1101 of the saphenous vein 1000. After the cutting by the second cutting devices 300 is complete, the saphenous vein, together with the surrounding tissue bound to the vein (saphenous fascia 1600) are removed from the living body (limb) of the patient, together with the dissecting devices and cutting devices.

The first and second cutting devices described above and used with the two dissecting devices 700, 700' can be bi-polar type electric devices as described previously. Also, the two dissecting devices 700, 700' can be inserted sequentially one after the other as described above, or generally at the same time.

FIG. 24A illustrates a portion of the living body (limb) in transverse cross-section after removing the cutting devices and the first dissecting device, and FIG. 24B illustrates a portion of the limb in longitudinal cross-section after such removal. FIG. 24B also illustrates, somewhat schematically, loop-shaped members that are used for stanching.

Figure 25C:
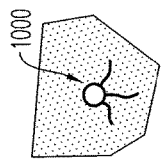
FIGS. 25A-25C depict aspects of a dissecting procedure.
Figure 25B:
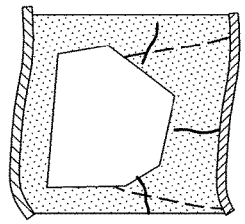
Figure 25A:
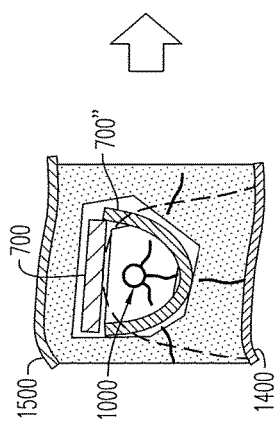

FIGS. 25A-25C, 26A-26C and 27A-27C illustrate different harvested vein shapes. FIG. 25A illustrates a U-shaped dissecting device 700" (cutting device) used together with the dissecting device 700. FIG. 25C illustrates the cross-section of the vein and bound tissue that is ultimately removed from the living body, and FIG. 25B illustrates the living body in transverse cross-section after removal of the vein and bound/surrounding tissue.

Figure 26C:
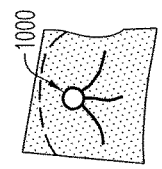
FIGS. 26A-26C illustrate aspects of another dissecting operation.
Figure 26B:
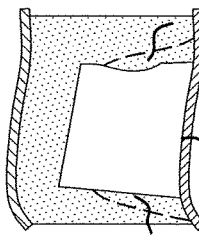
Figure 26A:
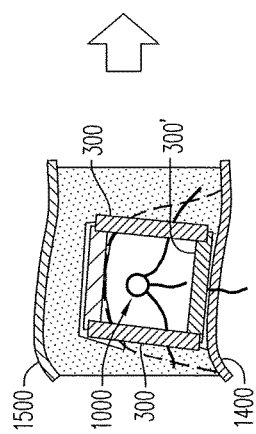

FIG. 26A illustrates an example in which the dissecting device 300 is positioned between the tissue (saphenous fascia) bound to the saphenous vein 1000 and the muscular fascia 1500, a pair of the cutting devices 300 are positioned on opposite sides of the great saphenous vein 1000, and another cutting device 300' similar to the first pair of cutting devices 300 is positioned between the skin 1400 and the vein 1000. FIG. 26C illustrates the saphenous vein 1000 and the surrounding or bound tissue that is removed after the procedure shown in FIG. 26A, and FIG. 26B illustrates the portion of the living body after the removal of the saphenous vein and surrounding tissue.

Figure 27C:
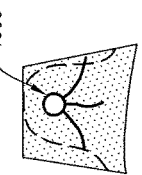
FIGS. 27A-27C show aspects of another dissecting procedure.
Figure 27B:
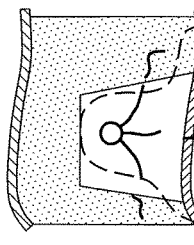
Figure 27A:
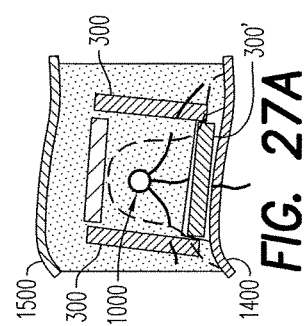

FIG. 27A is similar to FIG. 26A except that the particular configuration of the surrounding tissue that is dissected (cut away) and removed from the living body is slightly different.

FIGS. 25A-25C, FIGS. 26A-26C and FIGS. 27A-27C illustrate that using differently shaped dissecting devices (or cutting devices) together with the positioning and relative location of such devices will alter the shape of the surrounding tissue that is removed with the vein. FIGS. 27A-27C show an embodiment in which the cutting devices and dissecting devices are slightly spaced apart relative to the arrangement of the cutting devices and dissecting devices in FIGS. 26A-26C.

The cutting device illustrated in FIG. 25A can be the same as the cutting device 300 shown in FIG. 14 which possesses the generally U-shaped configuration in transverse cross-section. In the aspect of the method illustrated in FIG. 25A, the cutting device 300 and the dissecting device 700 together form a space that encloses, covers or surrounds the saphenous vein 1000. It is also possible to use other differently shaped or configured dissecting devices and/or cutting devices to vary the configuration of the tissue (i.e., tissue bound to the saphenous vein) that is removed together with the saphenous vein 1000. The methods or operational procedures described above involve steps or operations performed to harvest a vein (e.g., the saphenous vein 1100) from the living body of a patient. It is to be understood that the methods and operational procedures described above are not necessarily limited to dissecting the saphenous vein/saphenous fascia from the adjacent fat tissue or muscular fascia, as the disclosure has general application to dissecting tissue bound to a vein from other adjacent tissue in the living body. The methods or operational procedures involve providing access to the vein and tissue in the living body by making an incision in a patient's leg, thereby exposing the thin layer (e.g., tissue layer or saphenous fascia) that is bound to the vein. The operations or steps carried out above are then performed to dissect or separate the thin layer (e.g., fascia layer or tissue layer) from the other tissue (e.g., fat) as described above.

The methods or procedures described above can be furthered by solidifying the fat 1200 or the saphenous fascia 1600, preferably before inserting any of the dissecting devices and/or cutting devices into the living body. This can be accomplished by utilizing cooling techniques that cool the patient's limb (leg) from which the vein is being harvested. Cooling the leg can be carried out to subject the patient's limb (leg) to a temperature below room temperature that reduces the body temperature to below a typical body temperature of 98.6° F. The leg can be cooled to reduce the temperature of the patient's limb to between 14° F. and 68° F., more preferably between 32° F. and 50° F.

Another possibility to enhance the dissecting operation is to melt the fat tissue, once again before inserting any of the dissecting devices and/or cutting devices into the living body. This melting of the fat can be accomplished by heating the patient's limb (leg) in some way. The heating would be accomplished by subjecting the leg to a temperature above room temperature that raises the temperature of the patient's limb (leg) to a temperature above the typical body temperature of 98.6° F. The leg can be heated to increase the temperature of the patient's limb to between 122° F. and 176° F., more preferably between 131° F. and 167° F.

Figure 28A:
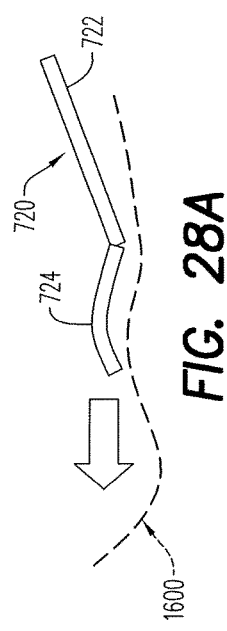
FIGS. 28A-28C show a modified version of a dissecting device.
Figure 28B:
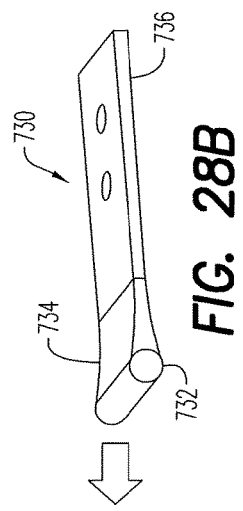
Figure 28C:
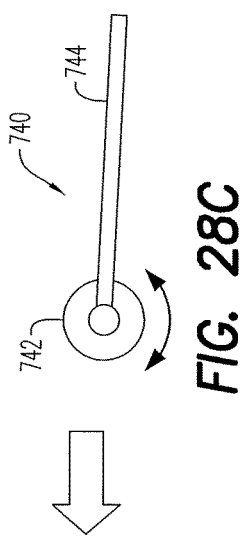

FIGS. 28A-28C illustrates additional modifications to the dissecting devices described above. FIG. 28A illustrates a modification that is intended to facilitate advancement of the dissecting device through the interface between the two tissues being dissected, the saphenous fascia and fat tissue in this example. The dissecting device 720 includes a proximally located relatively hard section or part 722 and a distally located relatively soft section or part 724. The relatively hard part 722 allows a force applied to the dissecting device 720 to be transmitted in a way that advances the dissecting device 720 in the living body in the forward direction indicated by the arrow, while the relatively soft part 724 is able to flex or bend while moving in the living body to help navigate along the saphenous fascia-fat tissue interface. The saphenous fascia 1600 possesses different characteristics relative to the fat tissue and is thus relatively easily separated from the fat tissue 1200. The relatively soft part 724 of the dissecting device 720 is thus able to be advanced along and generally conform (follow) the saphenous fascia-fat tissue interface in a way that facilitates separation or dissection without puncturing or otherwise damaging the two types of tissues.

FIG. 28B illustrates a modified form of the dissecting device 730 that includes a plate-shaped main body portion 736 and a distal end that is rounded, representing a portion of a circle. The edge shape of the distal end of the dissecting device 730 is thus blunted or softened in a way that is not so likely to break or otherwise damage the saphenous fascia and/or fat tissue. The rounded distal end of the dissecting section 730 can have an edge that is wider than a mesh size (void size) of the fat septum (fat particles), and can have an edge that is softer than the saphenous fascia and fat septum. The edge being wider than the mesh size of the fat septum and being softer than the saphenous fascia and fat septum help facilitate relatively easy movement along the saphenous fascia without entering between the fat septums. As the dissecting device enters between the fat septums, the dissecting member may not be able to move to a destination to lose landmarks. The phrase "wider edge" as used above refers to a diameter of the rounded distal end 732. The dissecting device 730 also includes a tapering portion 734 that tapers from the plate-shaped main body portion 736 to the rounded distal end 732.

FIG. 28C illustrates a further embodiment of the dissecting device in which the dissecting device 744 includes a freely rotatable roller 742 mounted at the distal end of the main body portion 744. This roller portion 742 helps reduce the sheer stress on the tissue at the saphenous fascia-fat tissue interface because the roller is able to rotate during the forward movement (indicated by the arrow in FIG. 28C) as the dissecting device 740 is pushed. An alternative to the roller would be to apply a sheer stress-reducing coating such as polytetrafluoroethylene (PTFE) on the distal end portion of the dissecting device. Such a coating could be applied, for example, to the rounded distal end of the dissecting device shown in FIG. 28B.

Another aspect of the disclosure here involves utilizing a dissecting device configured to inhibit or prevent movement or deviation of the vein (and the dissecting device) during the dissecting operation or procedure. FIGS. 29A-29E illustrates one embodiment of such a dissecting device. The dissecting device 750 shown in FIGS. 29A-29E includes an elongated member that, as seen in the top view of FIG. 29A, narrows from the proximal end (i.e., the right hand side in FIG. 29A) toward the distal end (i.e., the left-end in FIG. 29A). In the illustrated embodiment, the taper is continuous and gradual from the distal-most end of the dissecting device to the proximal-most end of the dissecting device.

FIG. 29B illustrates the dissecting device 750 in side view, and shows that the dissecting device vary from a straight portion at the distal end of the dissecting device to an enclosing or covering portion 754 that is not plate-shaped. As seen in the cross-sections of FIGS. 29C-29E, the straight portion at the distal end is flat or plate-shaped, and the covering portion 754 is radially curved. The radially curved covering portion generally encloses or surrounds the saphenous vein 1000. The drawing figures illustrate that the dissecting device 750 transitions from the straight portion to the cross-section of the covering portion shown in FIG. 29E. That is, the cross-sectional shape of the dissecting device 750 gradually transitions, beginning at the straight portion/covering portion interface, from the flat plate-shaped to the curved shape. In addition, the covering portion 754 exhibits a gradually increasing circumferential extent towards the proximal end of the dissecting device 750. Thus, as seen in FIG. 29D, the dissecting device is an approximate half-circle extending over a circumferential extent of about 180° to the cross-section shown in FIG. 29E in which the circumferential extent of the covering portion is greater, preferably about 300°. Thus, the circumferential extent at the cross-section shown in FIG. 29E is more than 1.5 times the circumferential extent at the cross-section shown in FIG. 29D. Also, the distance between the edges of the dissecting device as seen in the cross-section of FIG. 29E (a vertical cross-section to a central axis of the dissecting device) is preferably between about 3.0 cm and 7.0 cm, more preferably between about 4.0 cm and 6.0 cm.

The dissecting device 750 illustrated in FIGS. 29A-29E can be used in the following manner. An operational procedure begins by making an incision in the limb (e.g., leg) of the living body of the patient to create an access site to the vein (e.g. saphenous vein 1000). The distal end of the dissecting device 750 is then inserted into the living body by way of the incision, and the dissecting device 750 is moved along the vein 1000. When the dissecting device 750 is positioned relative to the vein 1000 in the manner such as illustrated in FIGS. 29A and 29B, the straight flat portion 752 of the dissecting device 750 is located between the vein 1000 and the skin as shown in FIG. 29C. At this time, the covering portion 754 of the dissecting device 750 is positioned relative to the vein 1000 in the manner shown in FIGS. 29D and 29E. As illustrated in FIG. 29D, the circumferential free ends of the dissecting device 750, as seen in transverse cross-section, contact the side branches or side vessels of the vein to hold the vein in position. Farther towards the proximal-most end of the dissecting device 750, the dissecting device has a much greater circumferential extent and thus tends to squeeze the side vessels of the vein 1000 towards one another in a way that constrains or holds the vein. The vein is thus held in a way that inhibits movement of the vein during subsequent cutting operations.

In this particular embodiment just described, the covering portion 754 is fixed in shape or configuration. It is possible to implement a modified construction in which the shape or configuration of the covering portion 754 changes or can be varied/adjusted.

For example, FIGS. 30A and 30B illustrate a dissecting device 760 that includes a flat straight portion 762 at the distal end similar to the flat straight portion 752 in the embodiment described above, together with an adjustable or changeable covering portion 764. In this illustrated embodiment, the shape-adjustable covering portion 764 is comprised of a pair of legs 765, 765 connected to one another at a hinge pin 766. The hinge pin allows the legs 765, 765 to be moved relative to one another. With this embodiment, the dissecting device 760 can be inserted into the living body by way of the incision, and after insertion so that the covering portion 764 overlies the vein 1000, the two legs 765, 765 are rotated to a position such as illustrated in FIG. 30B so that the legs 765, 765 hold the vein 1000 by way of the side branches 1100. Changing the legs 765, 765 to the position shown in FIG. 30B can help harvest a significant amount of fat with the dissecting device. Thereafter, the dissecting device 760 is moved.

FIG. 30C illustrates another version of the dissecting device 760' in which the covering portion 764' is shape-adjustable. Here, the covering portion 764' is comprised of an elongated member 765 that is configured to be bent into a curved shape. The dissecting device 765 shown in FIG. 30C includes the same flat straight distal end portion 762 shown in FIG. 30A. This embodiment of the dissecting device 760' is used in the manner similar to the dissecting device 760 described above in which the dissecting device 760 is inserted into the living body and moved to a position along the vein 1000, and is then changed to the curved shape shown in FIG. 30C. When in the configuration shown in FIG. 30C, the covering portion 764' applies a force to the side branches 1100 of the vein or surrounding the tissue of the vein tending to hold the vein 1000 in place. In this embodiment, like the embodiment shown in FIG. 30B, the thin layer bound to the vein 1000 (i.e., the saphenous fascia 1600 bound to the vein 1000) is contacted by the covering portion 764'.

FIG. 30D illustrates another shape-adjustable version of the dissecting device 760" in which the covering portion 764" is comprised of three legs 765", 765". The adjacent legs can be connected to one another by hinge pins similar to the hinge pins shown in FIG. 30B. In this embodiment shown in FIG. 30D, the hinge pins would be located at the corners of the covering portion 764" in the configuration shown in FIG. 30D. The dissecting device 760' shown in FIG. 30D also includes, at the distal end portion, a flat straight portion similar to the flat straight portion 762 shown in FIG. 30A. The use of the embodiment of the dissecting device illustrated in FIG. 30D is similar to that described above with respect to the embodiment depicted in FIGS. 29A-29E.

FIGS. 31A-31B illustrates one manner of using the dissecting device 750 illustrated in FIGS. 29A-29E, together with cutting devices. First, the flat straight distal end portion of the dissecting device 750 is inserted into the living body by way of the incision, and the dissecting device is moved in the forward direction along the vein 1000 until the dissecting device is positioned at the desired place for dissecting the tissue and harvesting the vein 1000. At this position, illustrated in FIG. 31A, the free ends of the curved covering portion 754 contact and press against the vein 1000 (the side branches 1100) thus holding the vein 1000 in place to inhibit movement. Next, as illustrated in FIG. 31B, a flat dissecting device like the flat dissecting 700' shown in FIG. 23B is inserted to a position illustrated in FIG. 31B in which the flat dissecting device is positioned between the vein 1000 and the muscular fascia 1500. The flat dissecting device is then moved to a position near the side branch 1100.

Next, a cutting device (first cutting device) like the cutting device 701' shown in FIG. 23B is inserted into the flat elongated dissecting device 700' so that the cutting device engages the connecting portion of the flat dissecting device 701'. The first cutting device is advanced along the flat dissecting device 701' toward the distal end of the flat dissecting device to thereby cut the side branch of the vein.

Next, the cutting device (first cutting device) is removed from the dissecting device 750, and two second cutting devices, which can be similar to the cutting devices 300 shown in FIGS. 3A and 3B, are inserted into the loving body on opposite sides of the vein 1000 (saphenous fascia 1600). Each of the second cutting devices 300 is inserted into a respective connecting portion at the side of the flat dissecting device 700' in a manner similar to that described above.

That is, the dissecting device 700' can include rails or grooves on the outwardly facing outer surfaces of the dissecting device 750 similar to the rails or grooves 231, 232 shown in FIGS. 2A and 2B. The second cutting devices 300 are then moved in the forward direction toward the end of the flat dissecting device 700' to thereby cut the side branches of the vein 1000. This insertion and movement of the second cutting device to cut the side branches 1100 can be carried out at the same time. Alternatively, one of the second cutting devices 300 can be inserted into the connecting portion on one side of the flat dissecting device 700' and then advanced in the forward direction to cut one of the side branches, and then the other second cutting device 300 can be inserted into the connecting portion at the other side of the flat dissecting device 700' and moved forward to cut the other side branch. Thereafter, the flat dissecting device 700' and the two second cutting devices 300 are removed followed by removable of the dissected/harvested vein 1000 with the severed side branches 1100.

Figure 32A:
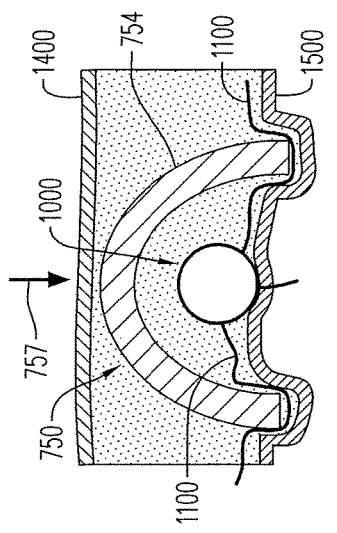
FIGS. 32A and 32B show aspects of another dissecting procedure.
Figure 32B:
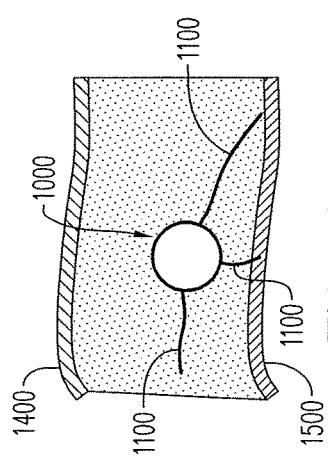

With respect to the dissecting device 750 illustrated in FIGS. 29A-29E, it is possible during use of this dissecting device to apply pressure from outside the living body and to apply such pressure to the proximal portion of the dissecting device 750, such as at the location identified by the arrow 757 in FIG. 29A. This application of an external force from outside the living body can help hold the vein and inhibit or prevent the vein from moving. FIGS. 32A and 32B illustrate the effect of such a pressing operation. FIG. 32A shows the portion of a limb of a living body before insertion of the dissecting device 750, while FIG. 32B illustrates the same portion of the limb of the living body after the dissecting device is inserted and after a force is applied as indicated by the arrow 757 in FIG. 32B. The applied force causes the vein (the side branches 1100) to be bent or folded as shown in FIG. 32B, thus holding the vein in place and inhibiting the vein from moving.

Figure 33:
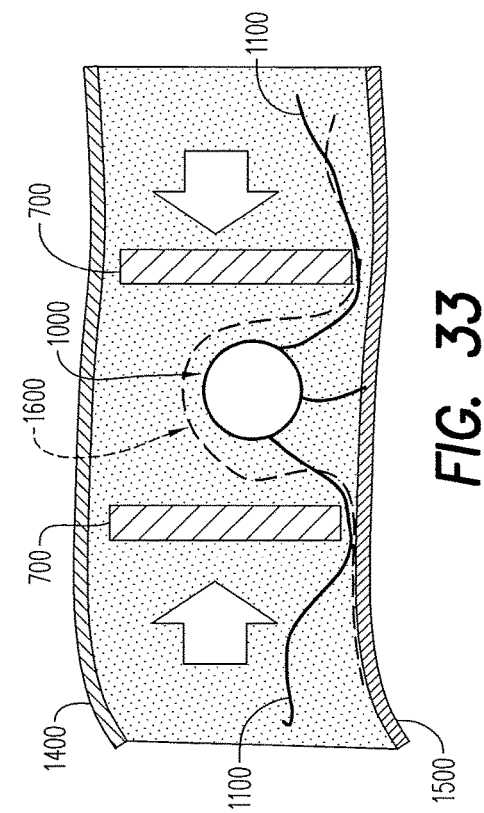
FIG. 33 illustrates an aspect of another dissecting procedure.

FIG. 33 illustrates another way of applying a holding force to hold the vein 1000 in place and inhibit movement of the vein. This method involves utilizing two flat dissecting devices which can be similar to the flat dissecting devices 700 illustrated in FIGS. 22A and 22B. As an alternative, it is also possible to use the flat dissecting devices 200 illustrated in FIGS. 2A and 2B. This method involves inserting the two flat dissecting devices 700 into the limb (leg) of the living body (patient) by way of the incision, and moving the flat dissecting devices 700 along the vein 1000 on opposite sides of the vein 1000. Pressing the two flat dissecting devices 700 towards one another as schematically illustrated in FIG. 33 by way of the arrows results in the vein 1000 being held in place to inhibit movement of the vein. This applied force can also fold the side branches 1100 somewhat while the dissecting devices 700 also contact the tissue bound to the vein (saphenous fascia). Once the vein is held by the two dissecting devices 700, it is possible to introduce a dissecting device like the dissecting device 700' described above and illustrated in FIG. 31B, followed by insertion and movement of the cutting device 701' to cut the side branch.

With respect to the various aspects of the disclosure described above and illustrated in FIGS. 29A-29E, FIGS. 30A-30D, 31A, 31B, 32A, 32B and 33, it is possible to solidify the fat or saphenous fascia before inserting the dissecting device or to melt the fat before inserting the dissecting device as described above. It is also possible to implement with these various embodiments the additional aspects described above and illustrated in FIG. 28A-28C.

Set forth next is a description of alternative embodiments of a dissecting device for dissecting tissue. In these embodiments, the dissecting device includes a wire configured to dissect one tissue (e.g., saphenous fascia) from other tissue (fat). Referring to FIG. 34, the dissecting device 800 includes a pair of rods or elongated members 802 mounted in respective rod holders (holders) 806. The rods 802 can be hollow tubes. In the illustrated embodiment, the two rods 802 are parallel to one another. The holders 806 are both mounted on a rod holder guide 808. Each of the holders 806 is preferably individually movable relative to the rod holder guide 808 through suitable operation of a dial (lever) 804. By operating the dial 804 of each holder 806, the holders 806 are movable relative to the guide 808, making it possible to adjust the position of the holder 806, and thus the rod or elongated member 802, along the guide 808 to thereby adjust the spacing or distance between the two rods or elongated members 802. Operating the dial 804 again (e.g., tightening the dial) fixes the position of the holder 806, and thus the rod or elongated member 802, along the guide 808 to thereby fix the position of the two rods or elongated members 802.

A wire 810 spans or extends between the two rods 802 near the distal ends of the rods 802 as illustrated in FIG. 34. The wire preferably passes through respective holes or slits near the distal end of each of the rods 802 and extend into the hollow interior of each of the rods 802. There is a suitable length of the wire 810 inside each of the rods 802 to accommodate movement of the rods 802 away from one another.

In the illustrated embodiment, the distal ends of the rods 802 are preferably tapered to a pointed or sharp end as illustrated in FIG. 34. This allows the rods to be introduced into the living body by way of an incision while permitting relatively easy insertion and movement in the living body.

The movable mounting of the holders 806 on the guide 808 is schematically illustrated in FIG. 34. Any suitable arrangement can be utilized for adjusting the position of the holders 806 along the guide 808. For example, each of the holders 806 can include a tubular mount encircling the guide 808. The dial (lever) 804 can pass through a hole in such tubular mount and press against the outer peripheral surface of the guide 808. Loosening the dial 804 allows the holder 806 to be moved along the guide 808. Once again tightening the dial 804 causes the dial to frictionally engage the outer peripheral surface of the guide 808 and thereby fix the position of the holder 806 relative to the guide 808.

Figure 36:
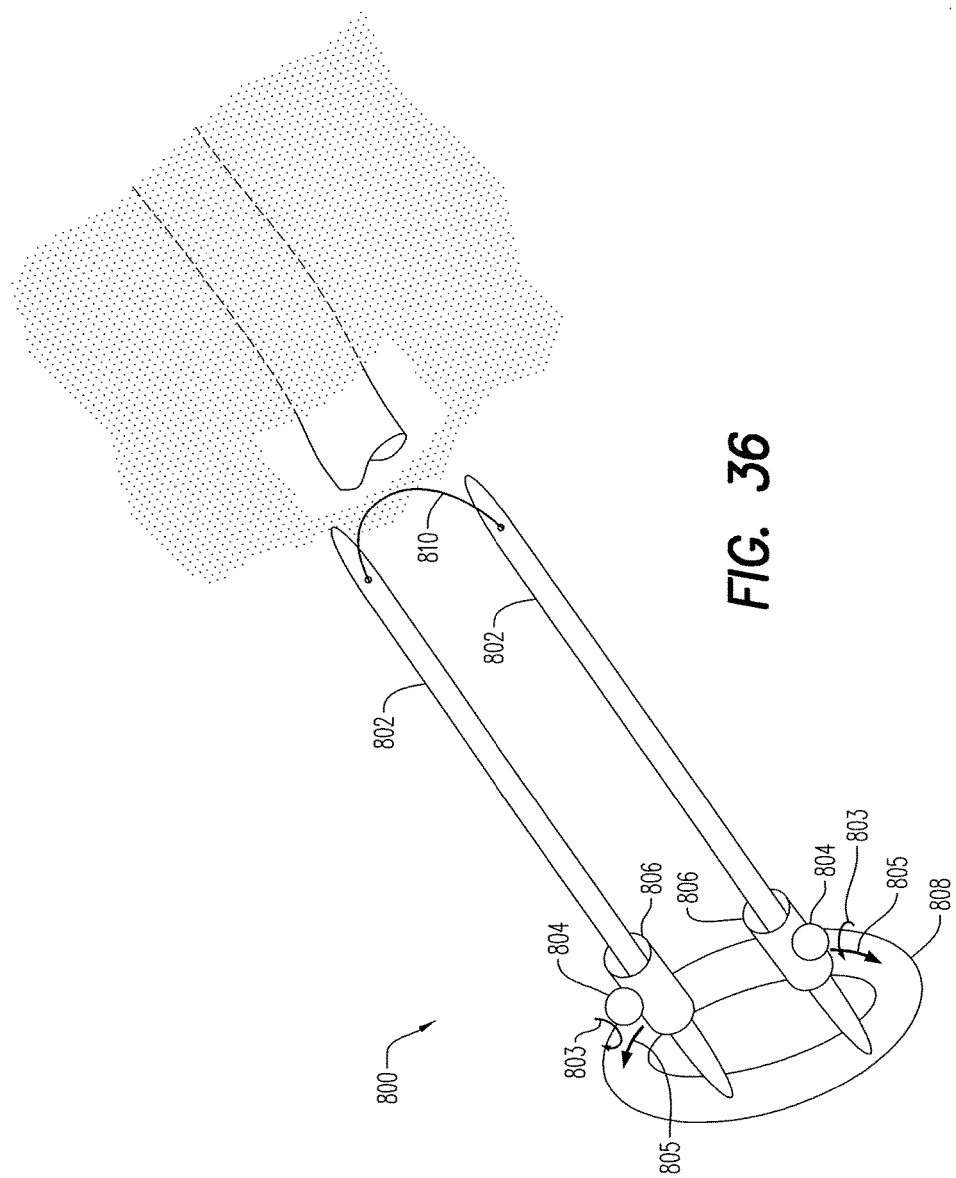
Figure 37:
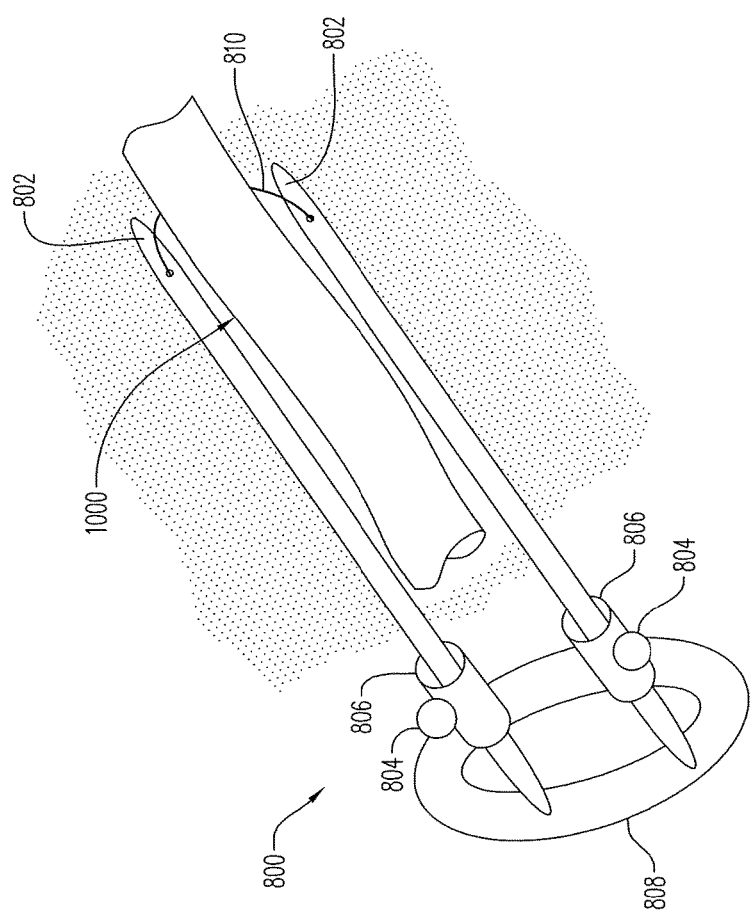

FIGS. 35-37 illustrate operational aspects of a method or procedure utilizing the dissecting device 800 shown in FIG. 34. Initially, as illustrated in FIG. 35, after an incision is made in the limb (e.g., leg) of the living body (patient), the distal ends of the rods 802 are positioned adjacent the saphenous vein 1000 or saphenous fascia 1600. The purpose for this is to adjust the spacing between the rods 802 so that they are positioned at the desired place relative to the desired dissection that is to be performed. For example, to dissect the saphenous vein 1000 and the saphenous fascia 1600 bound to the saphenous vein from the adjacent fat 1200, the dissecting device 800 would be positioned generally as illustrated in FIG. 35 so that the rods 802 are located at the interface between the saphenous fascia 1600 and the fat 1200. The dial 804 on one or both of the holders 806 is then loosened to adjust the position of the rod(s) 802 along the guide 808 so that the distal ends of the rods 802 are spaced apart by a distance which positions the distal ands of the rods 802 at the interface between the saphenous fascia 1600 and the fat 1200.

FIG. 36 illustrates the adjustment of the spacing between the rods 802 so that they are positioned at the desired relative position for dissecting. FIG. 36 illustrates the loosening (represented by the arrows 803) of the dial 804 and the subsequent movement (represented by the arrows 805) of the holders 806 along the guide 808 to move the rods 802 away from one another to the desired spacing. Next, as illustrated in FIG. 37, the rods 802 are inserted into the limb (leg) of the living body by way of the previously made incision in the limb, and are moved along the vein 1000. As the rods 802 and the wire 810 are moved along the vein in the forward or distal direction, the wire performs dissection (e.g., dissection of the saphenous fascia from the surrounding tissue or fat). The dissecting device 800 can be inserted into the limb of the living body along any of the sides of the vein 1000/fascia 1600. For example, the rods 802 and the wire 810 can be inserted between the saphenous fascia 1600 and the fat 1200, between the saphenous fascia 1600 and the skin 1400, or on opposite lateral sides of the vein 1000. The dissecting device 800 can be moved forward and backward in the distal and proximal directions in the living body to ensure that the tissue bound to the vein is appropriately dissected from the surrounding tissue.

The embodiment of the dissecting device 800 described above can include rods 802 that are fixed relative to the respective holders 806. But it is also possible to implement a configuration in which the rods 802 are axially adjustable along their longitudinal extent relative to the holders 806. For example, the rods 802 can be slidably positioned in the respective holder 806, and adjustable by way of a set screw that threadably engages a through hole in the holder 806. The set screw would be adjustable between one position in which the set screw bears against the outer surface of the rod 802 to fix the position of the rod 802 relative to the holder 806, and another position in which the set screw is spaced from (i.e., not in engagement with) the outer periphery of the rod 802 to permit the rod 802 to move relative to the holder 806.

Another alternative would be to utilize rods 802 comprised of two telescoping tubes, one positioned inside the other. With this possibility, a set screw could threadably engage a through hole in the outer tube to engage the outer periphery of the inner tube. Moving the set screw out of contacting engagement with the outer periphery of the inner tube would allow the inner tube to be axially moved or adjusted to change the length/position of the rod 802.

FIGS. 38-41 illustrate a variation on the dissecting 800 illustrated in FIGS. 34-37. The embodiment of the dissecting device 800' shown in FIGS. 38-41 is similar to the earlier embodiment shown in FIGS. 34-37, except for the following points. First, the embodiment shown in FIGS. 38-41 includes a third rod 802 mounted in a rod holder 806 that is adjustably mounted on the guide 808 in a manner similar to that described above with respect to the other holders 806. The third rod is centrally positioned relative to the other two rods (outer rods). In addition, each of the rods or elongated members 802 is comprised of an outer tube provided with a slit or slot 803 and an inner tube slidably received inside the outer tube. According to one possibility, one length of wire 810 extends between the distal ends of both the central rod 802 and the right-most rod 802 in FIG. 38, while another length of wire 810 extends between the distal ends of both the central rod 802 and the left-most rod 802 in FIG. 38. One end of each wire length is fixed relative to one of the rods, while the opposite end of the wire length is positioned in the interior of the other rod in a manner that allows the wires to move relative to the other rod to accommodate movement between the rods when the spacing between the rods is varied. Alternatively, a length of wire can be fixed to the distal end of the central rod 802 while freely passing through a hole in the inner tube in the other two rods 802. The wire 810 can be fixed to the distal end portion of the inner tube of each of the outer rods while being so that as the inner tube is moved towards the distal end of the outer tube, the wire is advanced in the forward or distal direction. The outer rods 802 have a spiral spring (set screw) 807 that connects with the wire so that the wire is always taught during the cutting operation.

Each of the rods 802 also includes an adjustment mechanism, such as a set screw 807, to allow the inner tube to be adjusted relative to the outer tube, and to then fix the position of the inner tube relative to the outer tube. This adjustment mechanism could be a set screw that threadably engages a through-hole in the outer tube and bears against the outer surface of the inner tube.

Figure 38:
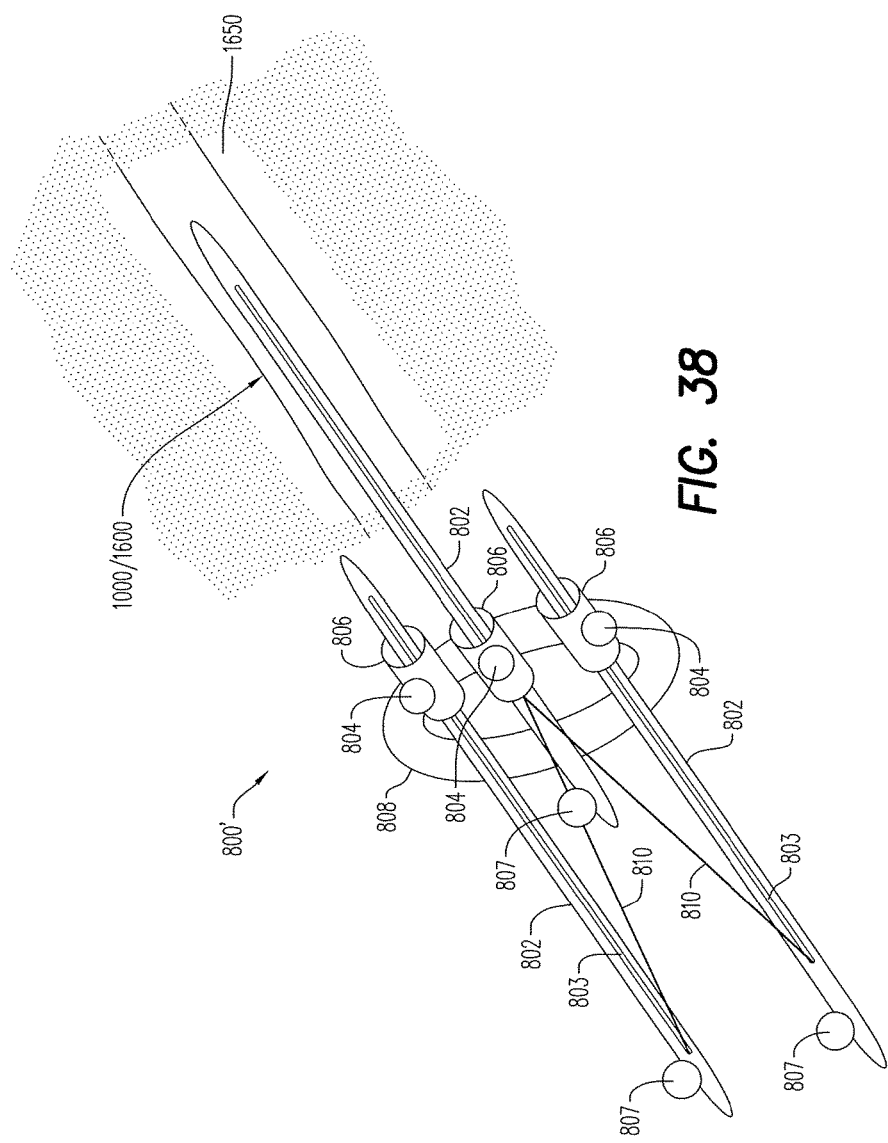
FIGS. 38-41 depict a dissecting device according to an additional embodiment and a manner of using such dissecting device.

One manner of use of the dissecting device 800' illustrated in FIGS. 38-41, is described below. First, as illustrated in FIG. 38, the central rod 802 is used as a mechanism for positioning the dissecting device 800' at the appropriate location. This is accomplished by positioning the central rod 802 distally beyond the other two rods 802 as illustrated in FIG. 38. This can be achieved by providing an adjustment mechanism between the rod 802 and the holder 806. A set screw or the like can be used in this regard to allow the rod 802 to move relative to the holder 806. This same adjustment mechanism can be provided for all of the holders 806 relative to the respective rods 802.

Figure 39:
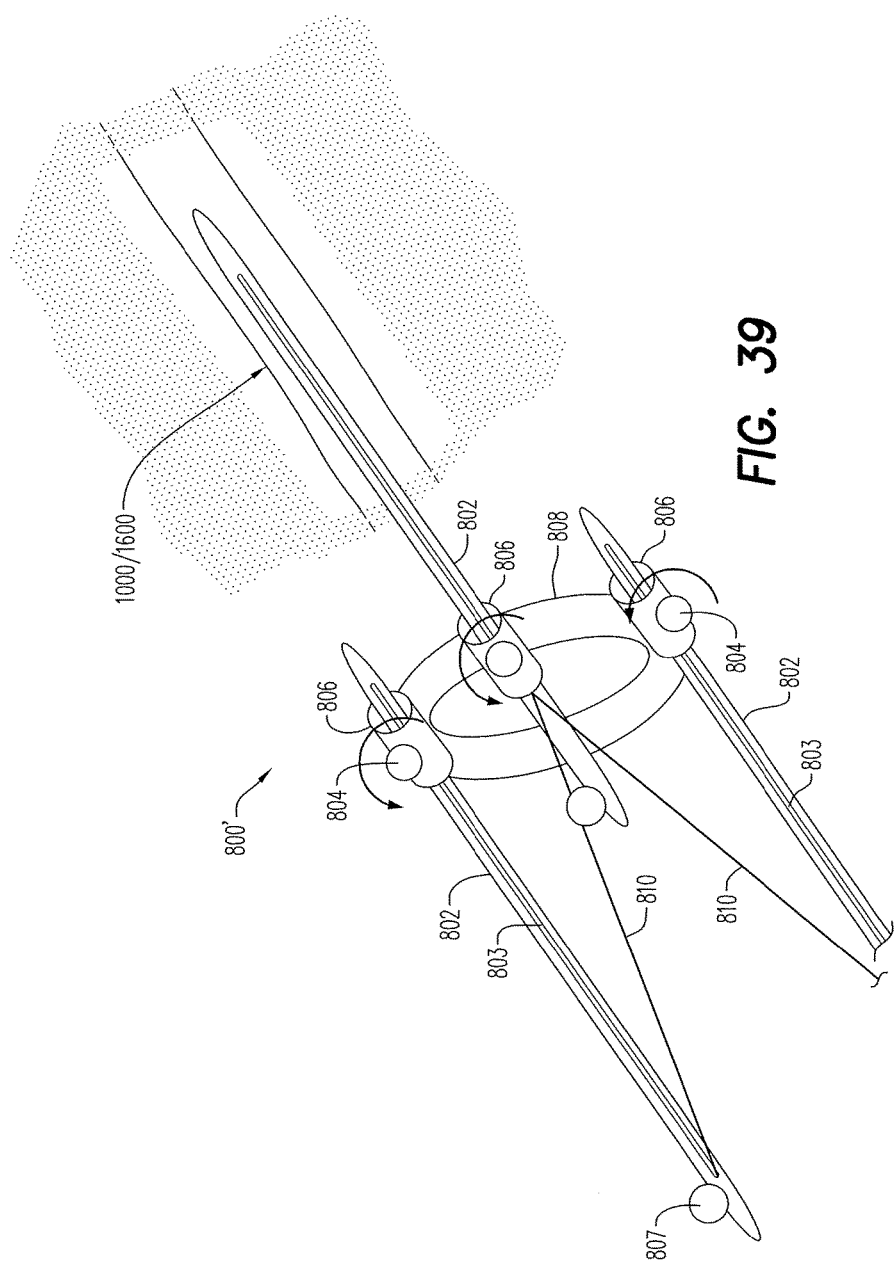
Figure 40:
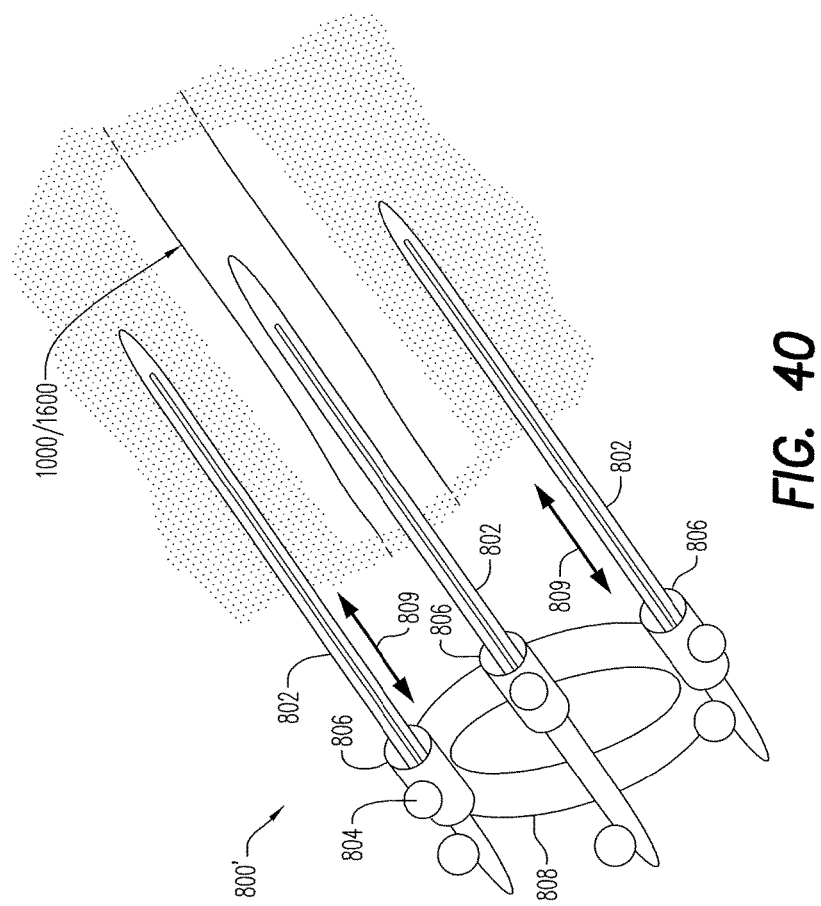

Next, as illustrated in FIG. 39, the dial (lever) 804 associated with each of the rods 802 is loosened to adjust the position of the respective holder 806 along the guide 808. The adjustment is carried out to position the rods 802 at the desired position for dissecting the desired tissue. The two outer rods 802 are preferably spaced apart from one another by a distance greater than the width of the saphenous vein 1000 and saphenous fascia 1600. Next, as illustrated in FIG. 40, the two outermost rods 802 are moved relative to their respective holders 806 and are inserted into tissue in the limb of the living body. This forward of distal movement of the outermost rods 802 is indicated by the arrows 809 in FIG. 40.

Figure 41:
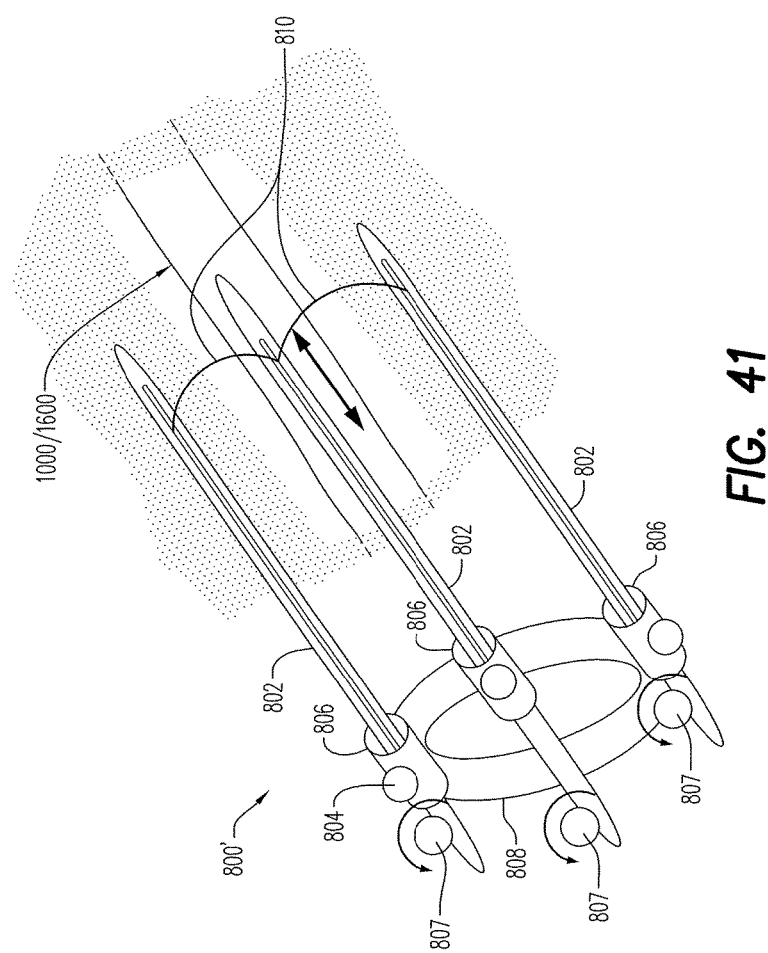

Next, as illustrated in FIG. 41, the wire 810 is advanced in the forward or distal direction. This movement is accomplished by loosening each of the adjustment devices 807 to allow the inner tube to be moved relative to the outer tube of each respective rod 802. Loosening the adjustment mechanism 807 associated with each rod 802 allows the inner tube to be moved or advanced in the forward direction which also moves the wire 810 in the forward direction so that dissection of the tissue occurs. The dissection will take place depending upon the location of the outermost rods 802. Thus, positioning the rods 802 at the saphenous fascia and fat interface will result in dissection of the fat 1200 from the saphenous fascia 1600. The inner tube of each respective rod 802 can be moved in the forward direction relative to the outer tube to carry out the desired extent of movement of the wire and the desired extent of dissection. After the dissection is complete, the dissecting device 800' is removed from the limb of the living body. It is also possible to use the dissecting device once again in the manner described above but along a different side or region of the saphenous vein 1000/saphenous fascia 1600.

FIGS. 42A-42C illustrate additional embodiments of the dissecting device that are variations on the dissecting device shown in FIGS. 38-41 and that represent other examples of the dissecting device disclosed here. FIG. 42A illustrates the wire 810 being used to dissect one tissue from another, for example the saphenous fascia from the fat. This straight configuration of the wire 810 is a configuration the wire would possess using the arrangement of the dissecting device shown in FIGS. 34-37. FIG. 42B illustrates a different wire configuration, namely a V-shaped wire configuration. This configuration of the wire 810' can be produced by positioning the rods 802 at, for example, rod positions so as to be in a state in which the wire 810' is straight in FIG. 42B. This wire configuration could be produced using the embodiment of the dissecting device shown in FIGS. 37-41.

FIG. 42C illustrates another variation in which the wire 810" possesses an arcuate, curved or partial circular-shaped wire configuration. This could be accomplished by utilizing more than three rods, and by arranging the rods so that they are generally positioned along a circular arc like that represented by the wire 810" in FIG. 42C. This configuration of the wire 810" could be produced with the embodiment of the dissecting device shown in FIGS. 37-41.

FIGS. 43A-43C, 44A-44C, 45A, 45B and 46 illustrate another embodiment of a dissecting device representing another example of the dissecting device disclosed here. As shown in FIG. 46, this embodiment of the dissecting device 820 includes a rod holder guide 822, a pair of rod holders 824, and three rods 826, 826, 828. FIGS. 43A-43C illustrate the rod holder guide 822 in more detail. The rod holder guide 822 is an elongated rectangular-shaped member 821 on which the rod holders 824 are mounted. The rod holder guide 822 is provided with a plurality of threaded screw through holes 823, each adapted to receive, for example, a threaded set-screw to permit and prevent sliding movement of the rod holders 824 on the guide 822. The guide 82 also includes a C-shaped holder portion 833 positioned at the center portion of the guide 822. The holder portion 833 is configured to receive the rod 828 illustrated in FIG. 45B. As seen in FIG. 43C, opposite sides of the elongated member 821 each include a V-shaped groove 821'.

Both of the rod holders 824 is comprised of a block-shaped member 836 provided with a centrally located C-shaped holder portion 835. The holder portion 835 of one of the rod holders 824 receives one of the rods 826 shown in FIG. 45A while the holder portion 835 of the other rod holder 824 receives the other rod 826 illustrated in FIG. 45A. The lower surface of the holder portion 824 is recessed, and the inner walls of the recess include inwardly directed V-shaped projections 836' that are received in the V-shaped recesses 821' in the guide 822.

FIG. 45B illustrates the rod 828 which is configured to be positioned in the holder portion 833 of the guide 822 (the center-positioned holder). This rod 828 includes an outer tube 831 and an inner tube 833. The outer tube includes a slit or slot 831', and the inner tube 833 is slidably movable relative to the outer tube 831.

FIG. 45A illustrates the rods 826 which are positioned in the holder portions 835 of the respective rod holder 824. Each of these rods 826 includes an inner tube 825 slidably positioned in an outer tube 827. The outer tube 827 of each of the rods 826 includes a slit or slot 827', and the inner tube 825 of each of the rods 826 is provided with a through-hole 825'. A wire 810 extends between the two rods 826, passing through respective through-holes 825'. One end of the wire 810 is preferably fixed to the inner tube of one of the rods 826, and preferably is loosely received in the interior of the inner tube of the other rod 826 so that the spacing or distance between the two rods 826 can be adjusted.

To use the dissecting device 820, the rod holders 824 are mounted on the guide 822 so that the rod holders 824 are positioned on opposite sides of the holder portion 833. The rod holders 824 are mounted on the guide 822 so that the V-shaped projections on the recesses at the underside of the holder portions 824 engage or are received in the V-shaped recesses along the opposite edges or sides of the elongated member 821 forming the guide 822. To facilitate the sliding movement of the holders 824 on the guide 822, the under surface of the holders 824 can be provided with roller bearings that engage the sides of the guide 822 during sliding movements. Next, the rod 828 is mounted on the holder portion 833 of the guide 821, one of the rods 826 is positioned in the holder portion 835 of one of the rod holders 824, and the other rod 826 is positioned in the holder portion of the other rod holder 824.

The dissecting device 820 illustrated in FIG. 46 is used or operated in a manner similar to that described above with respect to the dissecting device 800 illustrated in FIGS. 38-41. First, the centrally located rod 828 is positioned forwardly of the rods 826 on either side. This can be accomplished by moving the rod 828 (the outer tube 831) relative to the holder portion 833. It is possible to provide a suitable mechanism to fix the rod 828 in position relative to the holder portion 833 after the rod 828 has been positioned at the desired location relative to the holder portion 833. This mechanism can be, for example, a set screw as described above.

The rod or elongated member 828 is then inserted onto the saphenous vein 1000 or the saphenous fascia 1600 as described above. Next, the distance between the two outer rods or elongated members 826 is adjusted to position the rods 826 at the desired position to achieve the desired dissection with the wire 810. The distance between the rods 826 can be adjusted by moving one or both of the rod holders 824 relative to the guide 822. When the desired spacing is achieved, the rod holders 824 are fixed in place. This fixation of the rod holders 824 can be achieved by tightening set screws positioned in the through-holes 823 so that they press against the holders 824 in a way that fixes the holders 824 in place. The two rods or elongated members 826 can then be moved in the forward direction relative to the holder portions 835 of the respective holder 824 to position the rods 826 in the tissue adjacent the saphenous vein 1000 or saphenous fascia 1600. Finally, the inner tube 825 of each of the rods 826 is moved in the forward direction relative to the outer tubes 827 to move the wire 810 in the living body to thereby perform the desired dissection. The wire can thus cut tissue (fat, adipose tissue and muscle tissue in legs) and stop bleeding.

In the embodiments described above and illustrated in FIGS. 34-46, it is possible during use to apply a pressing force to the rods or elongated members 826, 828 (the outer tubes) at the proximal portion and from outside the body to press the rods against the veins and hold the vein in place as described previously in connection with other embodiments.

The embodiments of the dissecting device described above that utilize a wire for dissection can be modified in a variety of ways. For example, the wire can be configured so that it is loosely received in the inner tubes of the rods or elongated members so that the wire can be moved back and forth during dissection. Such modification may be helpful in the case of dissecting relatively hard tissue. It is also possible to configure the wire so that it spins around its central axis during dissection to help facilitate the dissection operation. Also, the wire can possess a somewhat wavy shape to help dissect relatively hard tissue. The wire can be a straight wire, a twisted or braided wire providing greater frictional engagement with the tissue, or a barbed wire. Each length of wire can also be comprised of more than a single wire length. For example, the wire length 810 in FIGS. 34-37 can be comprised of several wire lengths, and the wire lengths can be wound around one another. It is also possible to utilize wire that is an electrode of RF (mono and multi) for progress anteriorly with the rod.

The various embodiments of the dissecting device described above that utilize a wire can also include modifications or enhancements pertaining to the rods or elongated members. For example, the rods can be configured to permit insertion of an endoscope into the rods to facilitate viewing during the operational procedure. The tip of the rod is preferably transparent in this regard to permit viewing through operation of the endoscope. During use, the tip of the rod can exfoliate fat from the saphenous fascia or the surrounding tissue from the saphenous vein in the leg while certainly or reliably following the saphenous vein.

Another aspect of the disclosure here involves facilitating dissection of the vein by implementing various operations involving pulling the side branches of the vein. FIGS. 47A-47F illustrates one possibility. Pulling the side branches represents a procedure performed in addition to the dissecting procedures described above.

Figure 47A:
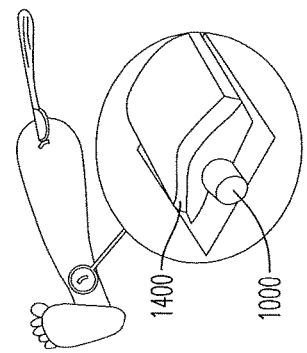
FIGS. 47A-47F illustrate aspects of another dissecting procedure.
Figure 47B:
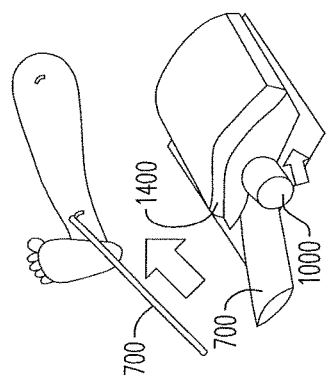
Figure 47C:
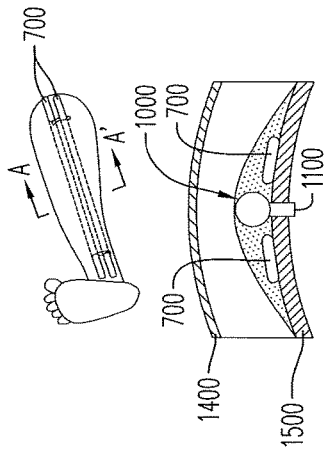

FIG. 47A illustrates that the procedure begins by making an incision at opposite ends of the limb (leg) of the living body (patient) to provide an entry incision and an exit incision. It is thus possible to expose the vein (saphenous vein) while securing an opening for a flat elongated dissecting device like the flat elongated dissecting device 700 shown in FIGS. 22A and 22B. FIG. 47B illustrates that after the incisions are made, the distal end of the flat elongated dissecting device 700 is inserted into the living body by way of the entry incision. And the flat elongated dissecting device 700 may be inserted on the muscular fascia or into the fat between the muscular fascia and the saphenous vein. As illustrated in FIG. 47C, the flat elongated dissecting device is moved inside the living body, along the vein 1000, so that the distal end of the flat elongated device 700 is exposed to the exterior of the body by way of the exit incision. Thus, both the distal and proximal ends of the flat elongated device 700 are exposed outside the body, while the intermediate portion of the flat elongated dissecting device between the distal and proximal ends is located inside the living body. The distal end of a second flat elongated dissecting device is also inserted into the entry incision and moved along the living body and along the vein 1000 until the distal end of the second flat elongated dissecting device is once again exposed outside the living body. The two flat elongated devices are positioned on opposite sides of the vein 1000. The two flat elongated devices are positioned on opposite sides of the vein 1000, but the two flat elongated devices may also be positioned out of alignment between the muscular fascia and the saphenous vein.

Figure 47D:
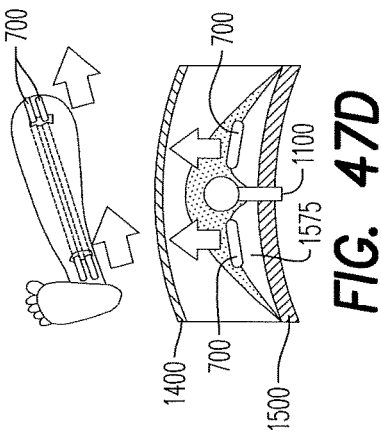
Figure 47E:
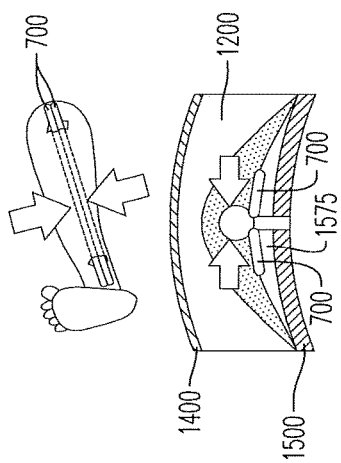
Figure 47F:
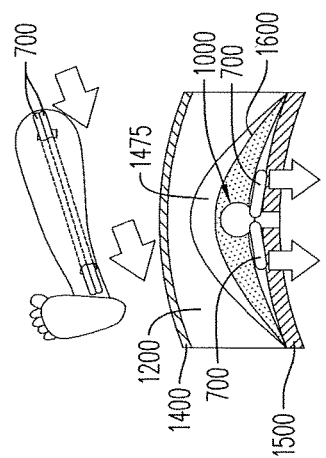

Next, as illustrated in FIG. 47D, the distal and proximal ends of both flat elongated dissecting devices exposed outside the living body are pulled upwardly in the direction of the arrows away from the muscular fascia 1500. A space 1575 is thus created under the flat elongated dissecting devices 700 (i.e., between the muscular fascia 1500 and the surface of the flat elongated dissecting device 700 facing the muscular fascia 1500). Next, as illustrated in FIG. 47E, the flat elongated dissecting devices 700 are moved towards one another to apply a pressing force to the side branch 1100 of the vein 1000, thereby holding the vein 1000. The flat elongated dissecting devices 700 may be moved towards one another to apply the pressing force to a bifurcation area of the vein of a vein side of the side branch 1100. According to this disclosed example, the flat elongated dissecting devices 700 are moved towards one another into contact with the side branch 1100 of the vein 1000. Finally, the method concludes as shown in FIG. 47F by pulling the side branch 1100 downwardly towards the muscular fascia 1500 and then the vein 1000 and the surrounding tissue are pulled towards the muscular fascia 1500 to thus separate the saphenous fascia 1600 from the adjacent tissue (fat tissue 1200) as indicated by the space 1475 between the saphenous fascia 1600 and the fat 1200 in FIG. 47F. This thus presents an alternative way of effecting dissection of one tissue such as the tissue bound to a vein (e.g., saphenous fascia bound to the saphenous vein) from other adjacent or adjoining tissue (e.g., fat). Before or after the flat elongated dissecting devices 700 are inserted near to the side branch, an imaging device may be inserted between the saphenous fascia and the fat. The flat elongated dissecting devices 700 can be reliably positioned close to the side branch. Before or after the flat elongated dissecting devices 700 are inserted near to the side branch, the flat elongated dissecting devices 200 may be inserted between the saphenous fascia and the skin. The flat elongated dissecting devices 200 can create or make a space 1475 between the tissue bound to the vein 1000 and the adjacent tissue (fat tissue) or between the vein 1000 and the surrounding tissue.

To help enhance the effectiveness of the dissecting operation, the flat elongated dissecting device 700 can be configured to enhance the ability of the flat elongated dissecting device 700 to grip the side branch of the vein. FIG. 48 illustrates the flat elongated dissecting devices 700, and FIGS. 49A-49H illustrate different possible cross-sectional shapes for the flat elongated dissecting devices to facilitate this gripping effort. In FIG. 49A, the flat elongated dissecting devices 700a possess a crescent-shaped cross-section so that the inwardly facing side edges of the devices 700a exhibit a sharp edge for grabbing and holding the side branch.

FIG. 49B illustrates flat elongated dissecting devices 700b that have inner edges or inner sides facing one another. These inner side edges are pointed (i.e., include a projection) to enhance the gripping ability of the flat elongated dissecting devices. FIG. 49C shows that the flat elongated dissecting devices can possess an oval-shaped cross-section so that the inwardly facing sides or edges narrow in a manner enhancing the gripping ability.

As shown in FIG. 49D, the inwardly facing sides or edges of the flat elongated dissecting devices 700d can be serrated or saw-tooth shaped in a way that enhances the ability of the devices 700 to grip the side branch of the vein. FIGS. 49E and 49F illustrate flat elongated dissecting devices in which the inwardly facing edges or sides interfit with one another in an interleaving or overlapping manner. FIG. 49G illustrates a further cross-section for the flat elongated dissecting devices 700g in which the inwardly facing edge or side of one dissecting device includes a projection that fits into a recess or groove in the inwardly facing side or edge of the other dissecting device. Finally, FIG. 49H illustrates a further alternative in which anti-slip material 700h' is applied to the inwardly facing side or edges of both of the devices. Examples of the anti-slip material include rubber, spongy-plastics, textured-metal, felt, fabric.

The configuration shown in FIG. 49D is an anti-slip design that effects secure holding, while the alternatives in FIGS. 49E-49G represent interfitting edge types that help maintain or keep the holding position in addition to the anti-slip function.

FIGS. 50A-50D illustrate a another embodiment of the dissection procedure representing a further example of the method or operational procedure disclosed here. In this embodiment, the two flat elongated dissecting devices 700 are inserted into the limb of the living body (patient) by way of the entry incision or access site in the manner described above, and are positioned on opposite sides of the vein (saphenous vein 1000) so as to be positioned on opposite sides of the side branch 1100. Then, as shown in FIG. 50B, the flat elongated dissecting devices 700 are rotated upwardly so that the inwardly facing sides or edges of the dissecting devices 700 are raised and moved away from the muscular fascia 1500 to create the space 1575 between the lower surface of the elongated dissecting device 700 and the muscular fascia 1500. The two flat elongated dissecting devices 700 are then moved toward one another as illustrated in FIG. 50C so that the inner sides or edges of the dissecting devices 700 come into contact with the side branch 1100 of the vein 1000. Finally, as illustrated in FIG. 50D, the inner sides or edges of the dissecting devices 700 are shifted or rotated downwardly while the outer sides or edges of the dissecting devices 700 are shifted or rotated upwardly, thus pulling the side branch 1100 of the vein, together with the vein itself, downwardly. As a result, tissue bound to the vein 1000 (saphenous fascia 1600) is dissected or separated from the adjacent tissue (e.g., fat 1200). This dissection operation results in a space 1475 between the tissue bound to the vein 1000 and the adjacent tissue (fat tissue).

FIGS. 59A-59E illustrate additional details about the dissecting device for carrying out the operational procedure shown in FIG. 50A-50D. In this embodiment, the opposite end of each of the flat elongated dissecting devices 700 is provided with a pin 792. The pins can be fixed relative to the dissecting devices 700 or can be removable/detachable. FIG. 59B shows that the pins are not coaxial with the central axis of the respective dissecting device 700. The pins at each end of the dissecting devices 700 are mounted in a common mounting block 796 that is comprised of a holder 793 and a stopper 794. As illustrated in FIGS. 59C-59E, the holder 793 includes a tapering through hole 793' that tapers in size from a larger dimension closer to the dissecting devices 700 to a smaller dimension closer to the stopper 794. This allows the pins 792 on the ends of the dissecting devices 700 to move toward one another as the pins are inserted further into the holders 796 is shown in FIGS. 59D and 59E. Thus, when the pins 792 are positioned relative to the holder 796 in the manner illustrated in FIG. 5D, the dissecting devices 700 are positioned farther away from one another compared to the pins 792 being positioned relative to the holder 796 as shown in FIG. 59E. After the pins 792 are inserted into the holder 796, the stopper 794 is placed around the ends of the pins as shown in FIG. 50A to thus fix the position of the pins 792. The stopper 794 can be made of a rubber material, and the opening in the stopper 794 can be dimensioned so that the stopper 794 tends to grip the pins and thus fix the position of the pins and the dissecting devices 700.

In use, the distal ends of the dissecting devices 700 are inserted into the limb of the living body by way of a previously made entry incision, and are moved in the living body along the vein (side branch of the vein) until the distal ends of the dissecting devices 700 exit outside the living body at the exit incision. To engage and hold the side branch of the vein, the pins 792 at each end of the dissecting devices 700 are positioned in one of the holder's 793 to move the dissecting devices 700 towards one another and into contact with the side branch to hold the side branch. Thereafter, one of the stoppers 794 is mounted on the pins 792 at each end of the dissecting devices 700 to fix the position of the pins 792 and thus the dissecting devices 700 so that the holding force applied to the side branch of the vein is maintained.

Figure 60B:
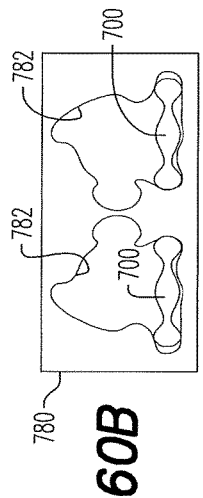
FIGS. 60A-60F illustrate features of another dissecting device useful in the operational procedure shown in FIGS. 50A-50D.
Figure 60C:
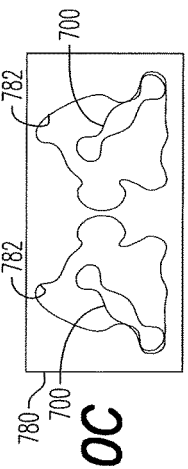
Figure 60D:
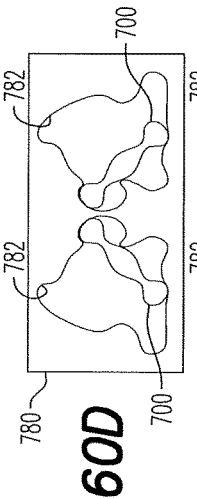
Figure 60E:
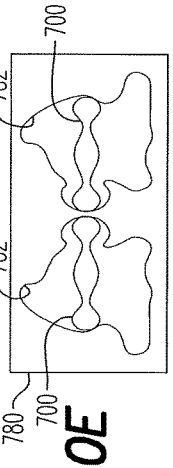
Figure 60F:
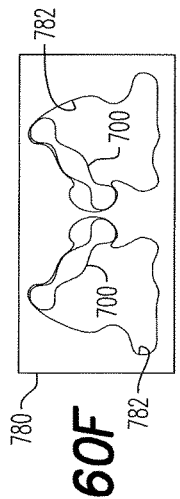
Figure 60A:
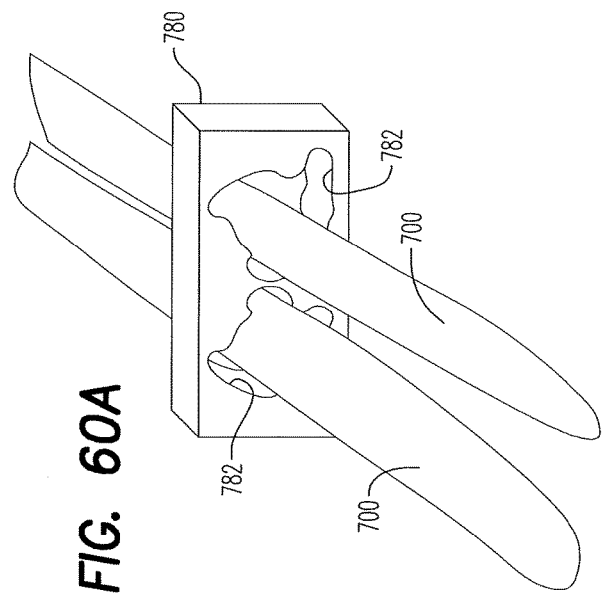

FIG. 60A-60F illustrate additional details about another dissecting device for carrying out the operational procedure shown in FIG. 50A-50D. Referring to FIG. 60A, the dissecting devices 700 are mounted in respective holes in a holder 780. The dissecting devices 700 are illustrated as being positioned in a single holder provided with two separated through holes 780, but it is to be understood that it is possible to mount each dissecting device 700 in respective holder 780 each provided with a through hole so that the end of one dissecting device is held by one holder and the other end of the dissecting device is held by another holder.

The two holes 782 in the holder 780 possess the same shape, but are mirror images of each other as can be seen from a comparison of the two holes illustrated in FIGS. 60B-60F. The hole is particularly configured to allow the dissecting devices 700 to be positioned in the different positions shown in FIGS. 50A-50D associated with holding the side branch.

The two holes 782 are configured so that the dissecting devices 700 are initially positionable in the manner shown in FIG. 60B. This position of the dissecting devices is similar to the positioning of the dissecting 700 in FIG. 50A in which the dissecting devices 700 are located on a side of the muscular fascia and both side of the side branch.

The holes 782 in the holder 780 are also configured so that the dissecting devices 700 can move from the position shown in FIG. 60B to the position shown in FIG. 60C. The position shown in FIG. 60C is similar to the position of the dissecting devices shown in FIG. 50B in which the dissecting devices 700 are rotated to lift the tissue bound to the vein (the saphenous fascia 1600) and space such tissue from the adjacent tissue (muscular fascia 1500).

The holes 782 are further configured to allow the dissecting devices 700 to shift from the position shown in FIG. 60C to the position shown in FIG. 60D in which the dissecting devices are moved toward one another to pinch, hold or grip the side branch. This positioning of the dissecting devices 700 is similar to the positioning of the dissecting devices shown in FIG. 50C.

The holes 782 are also configured to allow the dissecting devices 700 to move from the position shown in FIG. 60 to the position shown in FIG. 60E and then ultimately to the position shown in FIG. 60F. Changing the position of the dissecting devices 700 from the position shown in FIG. 60D to the position shown in FIG. 60E and ultimately to the position depicted in FIG. 60F results in the side branch being pull downwardly, similar to the operation depicted in FIG. 50D, to carry out the dissection previously discussed.

In use, the distal ends of the dissecting devices 700 are introduced into the limb of the living body by way of a previously made entry incision, and are advanced in the living body while moving along the vein (side branch of the vein) until the distal ends of the dissecting devices 700 exit outside the living body at the exit incision. Thus, both ends of both dissecting devices are positioned outside the living body. The distal ends of the dissecting devices 700 are positioned in the through holes 782 of one of the holders (or a pair of holders), and the proximal ends of the dissecting devices 700 are positioned in the through holes 782 of another holder (or another pair of holders). Thereafter, the dissecting devices 700 are moved in the manner shown in FIGS. 60B-60F and described above to perform the dissection.

FIGS. 51A-51D illustrate another dissecting procedure or method. This version of the dissecting operation involves the use of a pair of flat elongated dissecting devices 7001 which are positioned in a living body on a side of the muscular fascia and both sides of the side branch in the manner described previously. These dissecting devices 7001 are each comprised of two segments or sections 7001', 7001" connected together at a hinge. After the dissecting devices 7001 are inserted into the living body, the two elongated dissecting devices 7001 are lifted upwardly to create the space 1575 between the lower surface of the dissecting devices 7001 and the muscular fascia 1500 as illustrated in FIG. 51B. The next step in the operation involves, as illustrated in FIG. 51C, moving the two dissecting devices 7001 towards one another so that the inner sides or inner edges of the dissecting devices 7001 contact the opposite outer sides of the side branch 1100 to apply a holding force to the side branch. Finally, as illustrated in FIG. 51D, the outer segment 7001' of each dissecting device 7001 is rotated upwardly to pull the vein and the side branch downwardly, thus carrying out the dissection depicted in FIG. 51D.

FIGS. 61A-61G illustrate additional details about the dissecting device for carrying out the operational procedure shown in FIG. 51A-51D. In this embodiment, the dissecting devices 7001 are comprised of two sections 7001', 7001" hinged to one another and mounted in respective holders 770. An adjustment mechanism is operatively connected to the respective dissecting device 7001. In the illustrated embodiment representing one example of the disclosure here, the adjustment mechanism is a rotatable adjustment mechanism (dial) 772 operatively connected to the respective dissecting device 7001. Rotating the adjustment mechanism (dial) 772 rotates one of the sections 7001' of the dissecting device relative to the other section 7001" of the dissecting device as illustrated in FIG. 61F. It is thus possible to change the dissecting device from the configuration shown in FIG. 61D to the position shown in FIG. 61E.

A further aspect of this embodiment is shown in FIG. 61G in which each of the dissecting devices 7001 can be configured to be removably mounted to and detachably disconnected from the holder 770 and adjustment mechanism 772.

FIG. 52-55 illustrates further modifications to the already described dissecting operations involving holding and pulling the vein side branch. FIG. 52 shows that it is possible to position an expandable body 700 between each of the dissecting devices 700 and the muscular fascia 1500. Thus, after the dissecting devices 700 are inserted into the living body on opposite sides of the side branch 1100, the expandable member 850 is inserted, in the non-expanded or uninflated condition, between the muscular fascia 1500 and the dissecting devices 700. Thereafter, the expandable members 850 are expanded outwardly through inflation of the expandable members 850 to lift the dissecting devices 700 as shown in FIG. 52. Of course, the expandable members 850 can be inserted into the living body on opposite sides of the side branch before inserting the dissecting devices 700 or at the same time as insertion of the dissecting devices 700. The dissecting device 700 and the expandable member 850 may be integrally formed.

FIGS. 53A and 53B illustrate another embodiment that utilizes a slide and lift device. This slide and lift device 860 is positioned exterior of the body, but is used to lift the dissecting devices 700 as shown in FIG. 53A. That is, after the flat elongated dissecting devices 700 are inserted into the living body and moved along the vein 1000 to position the dissecting devices 700 on opposite sides of the side branch 1100 with the distal and proximal ends of the dissecting devices 700 exposed outside the living body by way of the entry and exit incisions, one of the slide and lift devices 860 is positioned under the proximal end portion of the dissecting device 700, and another of the slide and lift devices 860 is positioned under the distal end portion of the dissecting device 700. The dissecting devices 700 are then moved towards one another and towards the side branch 1100. During this movement, the dissecting devices 700 slide along the slide and lift devices 860 and are lifted by virtue of the configuration of the slide and lift devices 860.

FIG. 54 illustrates an alternative embodiment in which a stack of (plural number of) dissecting devices 700 is positioned on opposite sides of the side branch 1100. The stacks of dissecting devices 700 can be inserted together as a unit on opposite sides of the side branch, or can be inserted one on top of another in sequence.

FIGS. 55A and 55B illustrate another embodiment of the dissecting devices that once again includes two segments connected together by an intermediately located hinge. These dissecting devices are similar to the dissecting devices associated with the dissecting operation shown in FIGS. 51A-51D. But in the embodiment illustrated in FIGS. 55A and 55B, after the dissecting devices 7001 are inserted into the living body on opposite sides of the side branch 1100, the inner-most of the two segments of each dissecting device 7001 is rotated upwardly to lift the tissue that is bound to the vein 1000 (e.g., saphenous fascia 1600).

In each of the embodiments shown in FIGS. 52-55, the dissecting devices are moved into contact with the side branch of the vein as discussed previously, and the vein 1000 (side branch 1100) is pulled downwardly to carry out the dissection as described previously. The embodiments shown in FIGS. 52-55 disclose examples of ways to make a space to pull the side branch.

The dissecting operations illustrated in FIGS. 47-55 involve moving the dissecting devices towards one another to apply a force to the side branch that holds the side branch (e.g., moving the dissecting devices so that the inner sides or inner edges of the dissecting devices contact the side branch of the vein), and then pulling the side branch to carry out the dissection. It is desirable as a part of this operation to retain the engaged condition between the dissecting devices and the side branch. That is, it is preferable if the dissecting devices are able to maintain a strong hold on the side branch. FIGS. 56A-56C and FIGS. 57A-57C illustrate examples for achieving this result.

FIGS. 56A-56C illustrate a retention device 860 for retaining the dissecting devices 700 in a generally coplanar relation with each other and in close engagement with one another. The retention device includes a pair of clamps, with one clamp 872 located near one end of the pair of dissecting devices 700 and the other clamp 872 positioned near the opposite end of the pair of dissecting devices 700. FIG. 56B illustrates that each of the clamps 872 includes a pair of plates 874, the distance between which is controlled by suitable connectors like screws of the like that are adjustable to permit the distance between the two plates 874 to be varied. In this way, the two dissecting devices 700 can be positioned between the two plates 874 as shown in FIG. 56A, and then the connectors 876 can be tightened to maintain the two dissecting devices 700 in generally coplanar relation to one another.

The retention device 872 also includes a pair of loop members (endless members) made of an elastic material so that the loop members 878 are rubber band like in nature. One of the loop members 878 is positioned at one end portion of the pair of dissecting devices 700 and the other loop member 878 is positioned at the opposite end portion of the pair of dissecting devices 700. The elastic loop members 878 urge the inner sides or edges of the dissecting devices 700 towards one another and maintain the inner sides or edges of the dissecting devices 700 in contact with the side branch.

FIG. 57A-57C illustrates another embodiment of the retention device 890 that includes a pair of engaging members 892 that engage the dissecting devices 700. The engaging members 892 are generally C-shaped members that are freely slidably received on one or more shafts 894. In the illustrated embodiment the engaging members 892 are slidably mounted on a pair of shafts 894. A spring 896 bears against a block at the end of each shaft 894 and applies a biasing force to the engaging members 892 that urges the engaging members 892 towards one another.

In use, the dissecting devices 700 are positioned in the C-shaped engaging members 892 as shown in FIG. 57C. The C-shaped nature of the engaging members 892 retains the dissecting devices 700 in a generally coplanar relationship. The springs 896 bias the engaging members 892 toward one another to thus urge the two dissecting devices towards one another. In this way, the inner edges or sides of the dissecting devices 700 are retained in contacting engagement with the side branch of the vein.

FIGS. 58A-58F illustrates an alternative configuration for the dissecting devices 7002. In this embodiment, the end portions of the dissecting devices 7002 possess the generally flattened shape, somewhat oval in shape, whereas the intermediate portions or middle portion of the dissecting devices 7002 possess a different shape. The intermediate or middle portion of the dissecting devices possesses the cross-sectional shape shown in FIG. 58C. This cross-sectional shape is enlarged at three axially spaced locations so that the dissecting devices possess enlarged and rounded ends, and an enlarged middle portion. Between the enlarged ends and the enlarged middle is a necked down or narrowed region. In the illustrated embodiment, the transition from the larger size portion of the dissecting devices 7002 to the smaller size portions of the dissecting devices 7002 is a gradual taper.

FIG. 58E illustrates the dissecting devices 7002 positioned relative to one another to engage the side branch of the vein, while FIG. 58F illustrates the dissecting devices during the dissecting operation. The pivot point of each of the dissecting devices 7002 is the center of curvature of the surfaces that contact the side branch of the vein. The shape of the dissecting device in FIG. 58C (700, 7002) fits the hole 782 of the holder 780 of FIG. 60B. Therefore, when a user uses the dissecting device 700, 7002 and the holder 780, movement of the dissecting device 700, 7002 is restricted and supplemented by the shape of the hole 782 of the holder 780 to be the same movement of FIGS. 50A-50D. The dissecting device of FIG. 58B and FIG. 58D is flat. Therefore, the dissecting device is easily inserted into the living body. The operational sequence in FIGS. 58E and 58F is similar to that shown in FIGS. 50A-50D. A contact portion of the dissecting device 7002 has a curve that is bigger than a curve of a contact portion of the dissecting device 700. When the dissecting device 7002 pinches the side branch of the vein together with the other dissecting device, the bigger curve of the dissecting devices 7002 that pinch the side branch are harder to shift than the smaller curve of the dissecting device 700.

The various features and aspects illustrated in FIGS. 47A-47F involve ways of tearing out dissection by holding the vein (side branch of the vein) and pulling the vein (side branch of the vein) in a direction away from the tissue to be separated. In each of these aspects, the method generally involves making an incision in a limb to expose the vein and provide an access opening for inserting the dissecting device. It is possible to confirm the location of the tissue bound to the vein (saphenous fascia) and the adjacent tissue from which the tissue bound to the vein is to be separated from (muscular fascia). This can be accomplished visually. An incision is also made for allowing exiting of the distal end of the dissecting devices during the placement of the dissecting devices. This exit incision can be made at the same time as the entry incision or after moving the dissecting device along the vein. The distal ends of the dissecting devices are then inserted into the living body and moved along the vein. The presence and location of the side branch can be confirmed, either under visualization or through use of an imaging device. The dissecting devices are advanced or moved along the vein until the distal ends of the dissecting devices pass through the exit incision and are located exterior of the body. The two dissecting bodies (elongated flat body) are then lifted or rotated to produce a space between the saphenous fascia bound to the vein and the muscular fascia. The two dissecting devices are next moved toward one another to contact a hold the side branch. With the side branch held by the dissecting devices, the dissecting devices are then moved or pulled in a direction to carry out the dissection. The vein or the tissue bound to the vein is thus separated from other tissue (fat) by pulling the side branch of the vein and twisting the side branch of the vein. Twisting the side branch of the veins slides the tissue relative to other tissue in a circumferential direction and an area of a fitting part of the tissue and other tissue decrease. Therefore, twisting the side branch of the vein and pulling the side branch of the vein at the same time can effect more easy separation.

As a way of enhancing the dissection that occurs by holding and pulling the side branch of the vein away from the tissue to be separated (fat), it is possible to implement another holding aspect involving holding a portion of the limb (leg) to maintain the space created during the pulling-up of the side branch. FIGS. 62A-62C illustrate one example of a procedure that reliably creates a space. The embodiment shown in FIG. 62A illustrates the side branch being pulled away from the fat 1200 to dissect the saphenous fascia 1600 from the fat 1200, thus creating the space 1475 between the fat 1200 and the saphenous fascia 1600. To maintain this space, it is possible to, manually pinch the skin of the patient from outside the body, in the region of the dissection, and pull upwardly as indicated by the upwardly directed arrows in FIGS. 62A and 62B. An alternative is illustrated in 62C. Here, hooks 771 are used to engage (hook) portions of the limb on the skin side of the vein, in the region of the dissection, and to then apply an upwardly directed pulling force using the hooks. This once again maintains the space 1475.

FIGS. 63A-63C illustrate another embodiment in which pressure is applied from opposite sides of the limb in the region of the dissection to help maintain the space 1475. One embodiment illustrated in FIG. 63B involves applying manual pressure on opposite sides of the rim as indicated by the direction of the arrows in FIGS. 63A and 63B to hold the space 1475.

Another possibility shown in FIG. 63C involves using a pair of plates 773 (flat plates) to apply pressure on opposite sides of the limb as indicated by the arrows to thereby help maintain the space 1475 resulting from the dissection.

Figure 64A:
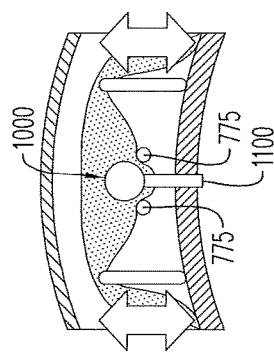
FIGS. 64A and 64B depict aspects of other operational procedures for holding parts of the limb.
Figure 64B:
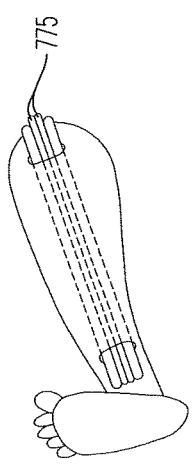

Another alternative shown in FIGS. 64A and 64B involves inserting a pair of elongated rods 775 at a position adjacent the vein 1000 and the side branch 1100 as shown in FIG. 61B. A pair of dissecting devices 700 and the pair of elongated rods 775 are inserted between the saphenous fascia and the muscular fascia. The pair of dissecting devices 700 makes a space and the pair of elongated rods 775 holds the side branch 1100 and pulls the side branch.

Figure 65B:
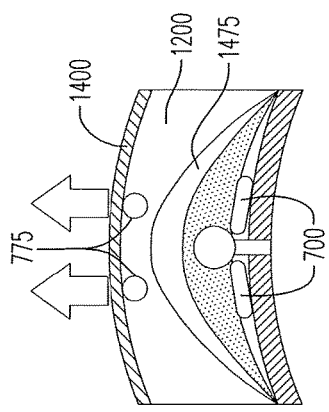
FIGS. 65A-65C show aspects of further operational procedures for holding parts of the limb.
Figure 65C:
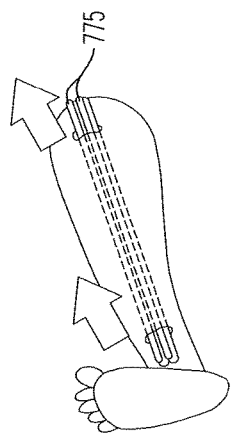
Figure 65A:
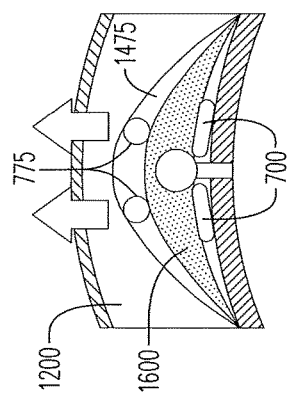

FIGS. 65A-65C illustrate another variation. Here, the rods 775 are inserted either between the saphenous fascia and the fat 1200, or between the fat 1200 and the skin 1400. In both cases shown in FIGS. 65B and 65C, the elongated rod 775, when positioned in the manner illustrated, are pulled upwardly in the direction indicated by the arrows to apply a pulling force that helps maintain or hold the space 1475 created by the dissection.

FIGS. 66A-66D depict another embodiment of a dissecting device. FIG. 66A illustrates that the dissecting device 900 includes a first dissecting device 902 and a second dissecting device 904. The first dissecting device 902 is a flat elongated member that includes a rail 903. The second dissecting device 904 is specifically configured to be mounted in the rail and then slid or moved along the rail. The second dissecting device 904 can thus move along, and relative to, the first dissecting device 902. As illustrated in the top view of FIG. 66C, the second dissecting device 904 includes three dissecting portions 905, each of which is in the form of a pointed projection. The second dissecting device 904 also includes curved portions 906 between the dissecting portions 905 (projections).

A dissecting operation involving use of the dissecting apparatus 900 shown in FIGS. 66A-66D is as follows. In FIG. 66B, the lower side represents the calf side and the top side represents in the body and the thin side. First, an incision is made in the limb (leg) of the living body (patient). The distal end of the first dissecting device 902 is then inserted into the living body by way of the entry incision so that the first dissecting device is located under the vein (saphenous vein 1000) such as shown in FIG. 66B. The first dissecting device is thus located between the fascia and the vein, or between fascia and fat. After the second dissecting device is inserted into the living body, the first dissecting device is slidably mounted on the first dissecting device, or was previously mounted on the first dissecting device and then introduced into the living body by way of the entry incision. This second dissecting device 904, slidably mounted on the first dissecting device 902, is then pushed from outside the living body so that the second dissecting device 904 is moved along the vein. As a result, the vein is dissected from other tissue (e.g., fat) in the thickness direction of the dissecting device. In FIG. 66B, the lower side represents the calf side and the top side represents in the body and the thin side.

FIGS. 66B and 66D show that the second dissecting device 904 can be configured as a generally upside-down U-shaped dissecting device. Thus, when the second dissecting device 904 is mounted on the rail 903 of the first dissecting device 902 and is advanced along the vein 1000 by the pushing force applied to the second dissecting device from outside the body, the first and second dissecting devices together surround or enclose the vein 1000 so that moving the second dissecting device 904 along the first dissecting device 902 results in the vein and/or tissue bound to the vein being dissected from the surrounding tissue such as fat. It is thus not necessary to insert and remove the dissecting device multiple times, or insert multiple detecting devices.

FIGS. 67A-67D illustrate another embodiment of the dissecting apparatus. This embodiment of a dissecting apparatus 910 includes a flat elongated first dissecting device 912 and a second dissecting device 914. As is apparent from FIGS. 67B-67D, the first dissecting device 912 includes two spaced apart legs 913 connected at their front or distal ends. Each leg 913 of the first dissecting device 912 includes a groove 917, and the first dissecting device 914 includes a plurality of rollers 919 positioned in each of the grooves of the legs 913 to facilitate movement of the second dissecting device 914 along the first dissecting device 912. The first dissecting device 912 is otherwise similar to the first dissecting device described above in that it possesses an upside-down U-shaped configuration as illustrated in FIGS. 67B and 67D. In addition, the first dissecting device 914 includes a plurality of projecting dissecting portions 916, with a curve between adjacent dissecting portions.

The operation of this embodiment is similar to that described above with respect to the dissecting apparatus 900. But in this embodiment shown in FIGS. 67A-67D, the curves of the second dissecting device catch the side branch of the vein 1000 and cut the side branch. The second dissecting device 914 includes an energy device 915 on its forwardly facing surface, and this energy device allows the side branch to be cut and to stop bleeding. The energy device can be located on the curved portions 918 of the first dissecting device. The energy device can be RF, laser and others.

The embodiment shown in FIGS. 68A-68D is very similar to the embodiment shown in FIGS. 66A-66D, except that the second dissecting device possesses an upstanding pusher 920. This upstanding pusher 920 makes it easier to push the second dissecting device from outside the body and move the second dissecting device relative to the first dissecting device in the living body along the vein. Preferably, the skin is convex by the pusher to rather easily push.

It is possible with the embodiments shown in FIGS. 66-68 to configure the curved upper portion 906, 918 of the second dissecting device from an elastic material. The second dissecting device can also be made of mesh material. In the illustrated embodiment, the second dissecting device includes three dissecting portions (projections), but it is to be understood that a different number of dissecting portions can be utilized. Each of these three dissecting portions is preferably an acute angle (i.e., the projection). Each of the curves of the second dissecting device also acts as a cutting device. The cutting device may be the energy device and a blade. The energy device associated with the embodiment shown in FIGS. 67A-67D can be mono-polar/bi-polar.

The harvesting of a bypass vessel for use in vascular bypass grafting has been described above in the aforementioned embodiments, but the use of the harvested blood vessel is not limited to the bypass vessel.

The detailed description above describes embodiments of a blood vessel dissecting device and blood vessel dissecting method representing examples of the invention disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for harvesting a vein in a living body comprising:
   providing an access site permitting access to a vein located inside a living body from outside the living body;
   exposing at the access site a tissue layer surrounding the vein;
   inserting a distal end of a flat elongated dissecting device into the living body by way of the access site, the flat elongated dissecting device possessing a thickness;
   moving the flat elongated dissecting device so that a surface of the flat elongated dissecting device contacts the tissue layer surrounding the vein, and continuing to move the flat elongated dissecting device while maintaining the surface of the flat elongated dissecting device in contact with the tissue layer to dissect the tissue layer surrounding the vein from adjacent tissue in a direction of the thickness of the flat elongated dissecting device, the adjacent tissue being materially different from the tissue layer surrounding the vein; and
   removing from the living body the vein that has been dissected from the adjacent tissue together with the tissue layer surrounding the vein.

2. The method according to claim 1, wherein the access site is provided by making an incision in skin of the living body.

3. The method according to claim 1, wherein the flat elongated dissecting device is inserted between skin of the living body and the vein.

4. The method according to claim 1, wherein the adjacent tissue is fat tissue, and the tissue layer surrounding the vein is Saphenous fascia.

5. The method according to claim 1, wherein the flat elongated dissecting device is a first flat elongated dissecting device, the method further comprising inserting a distal end of a second flat elongated dissecting device into the living body by way of the access site, and moving the second flat elongated dissecting device so that a surface of the second flat elongated dissecting device contacts the tissue layer, and continuing to move the second flat elongated dissecting device while maintaining the surface of the second flat elongated dissecting device in contact with the tissue layer to dissect the tissue layer from adjacent tissue in a direction of the thickness of the second flat elongated dissecting device.

6. The method according to claim 5, wherein the first flat elongated dissecting device and the second flat elongated dissecting device are moved along the vein on opposite sides of the vein.

7. The method according to claim 5, wherein the second flat elongated dissecting device is configured to move past a side branch of the vein, the method further comprising inserting a cutting device into the living body, and moving the cutting device relative to the second flat elongated dissecting device and along the second flat elongated dissecting device toward the distal end of the second flat elongated dissecting device, and cutting the side branch with the cutting device.

8. The method according to claim 5, wherein the flat elongated dissecting device is located between skin of the living body and the vein during dissection of the tissue layer from other tissue.

9. The method according to claim 5, connecting a cutting device to at least one of the first flat elongated dissecting device and the second flat elongated dissecting device so that the cutting device is in a connected state, and moving the cutting device in the connected state toward the distal end of the first flat elongated dissecting device while using the cutting device to cut tissue in the living body as well as first side branches branching from the vein.

10. The method according to claim 9, wherein the cutting device is a first cutting device, the method further comprising connecting a second cutting device to at least one of the first flat elongated dissecting device and the second flat elongated dissecting device so that the second cutting device is in a connected state, and moving the second cutting device in the connected state toward the distal end of the first flat elongated dissecting device while using the second cutting device to cut tissue in the living body as well as second side branches branching from the vein.

11. The method according to claim 10, wherein the removing of the vein from the living body occurs after the first and second flat elongated dissecting devices have dissected the tissue layer from the adjacent tissue and after the first and second cutting devices have cut the tissue in the living body as well as the first and second side branches so that the vein is separated from surrounding tissue.

12. The method according to claim 5, connecting a cutting device to both the first flat elongated dissecting device and the second flat elongated dissecting device, and moving the cutting device toward the distal end of the first flat elongated dissecting device while using the cutting device connected to the first and second flat elongated dissecting devices to cut side branches branching from the vein.

13. The method according to claim 1, wherein the vein is a Saphenous vein and the tissue layer surrounding the vein is a layer of Saphenous fascia bound to the Saphenous vein.

14. A method for dissecting tissue bound to a vein in a living body from other tissue adjacent the tissue that is bound to the vein, the method comprising:
   creating an access site permitting access, from outside the living body, to the tissue bound to the vein located inside the living body;
   exposing by way of the access site the tissue that is bound to the vein;
   inserting a distal end of a flat elongated dissecting device into the living body by way of the access site, the flat elongated dissecting device possessing a thickness;
   moving the flat elongated dissecting device so that a surface of the flat elongated dissecting device contacts the tissue that is bound to the vein; and
   continuing to move the flat elongated dissecting device while maintaining the surface of the flat elongated dissecting device in contact with the tissue that is bound to the vein to dissect the tissue that is bound to the vein from the other tissue in a direction of the thickness of the flat elongated dissecting device, the tissue bound to the vein being different from the other tissue,
   wherein the tissue that is bound to the vein is tissue bound to the Saphenous vein, and the other tissue is fat, and further comprising solidifying the fat or the tissue bound to the Saphenous vein before inserting the flat elongated dissecting device into the living body, the solidifying of the fat or the tissue bound to the Saphenous vein comprising cooling a portion of the living body in which is located the fat and the tissue bound to the Saphenous vein.

15. The method according to claim 14, wherein the continued movement of the flat elongated dissecting device dissects the tissue that is bound to the vein from the fat.

16. The method according to claim 14, wherein the moving of the flat elongated dissecting device includes moving the flat elongated dissecting device to straighten the tissue that is bound to the vein.

17. The method according to claim 14, further comprising inserting an endoscope into the flat elongated dissecting device to visualize movement of the flat elongated dissecting device in the living body.

18. The method according to claim 14, wherein the flat elongated dissecting device is a first elongated dissecting device, the method further comprising inserting a distal end of a second elongated dissecting device into the living body by way of the access site and connecting the second elongated dissecting device to the first elongated dissecting device so that the first elongated dissecting device and the second elongated dissecting device enclose a space in which is positioned the vein.

19. The method according to claim 18, further comprising moving the second elongated dissecting device along the vein and cutting side branches of the vein into the living body by way of the access site and connecting the second elongated dissecting device.

20. A method for harvesting a vein in a living body comprising:
   providing an access site permitting access to the vein located inside a living body from outside the living body, the vein being a Saphenous vein inside the living body;
   exposing at the access site a tissue layer surrounding the Saphenous vein that is a layer of Saphenous fascia bound to the Saphenous vein;
   inserting a distal end of an elongated dissecting device into the living body by way of the access site;
   moving the elongated dissecting device between the layer of Saphenous fascia and an adjacent tissue to dissect the layer of Saphenous fascia from the adjacent tissue; and
   removing from the living body the Saphenous vein that has been dissected from the adjacent tissue, the removing of the Saphenous vein from the living body including removing the Saphenous vein from the living body together with the layer of Saphenous fascia, wherein the adjacent tissue is materially different from the layer of Saphenous fascia.

21. The method according to claim 20 wherein the adjacent tissue is a fat.

* * * * *